United States Patent
Carter-Su et al.

(10) Patent No.: US 6,312,941 B1
(45) Date of Patent: *Nov. 6, 2001

(54) COMPOSITIONS AND METHODS FOR IDENTIFYING SIGNALING PATHWAY AGONISTS AND ANTAGONISTS

(75) Inventors: Christin Carter-Su; Liang-you Rui, both of Ann Arbor; David S. Karow, Northville, all of MI (US)

(73) Assignee: The Regents of the University of Michigan, Ann Arbor, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/980,080

(22) Filed: Nov. 26, 1997

(51) Int. Cl.⁷ .............................. C07H 21/02; C12N 1/20

(52) U.S. Cl. .................................... 435/254.2; 435/240.2; 435/252.3; 435/320.1; 536/23.1; 530/350

(58) Field of Search .......................... 530/350; 436/22.1, 436/23.1, 23.4–23.6; 536/23.1; 435/240.2, 252.3, 254.2, 320.1

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,434,064 | 7/1995 | Schlessinger et al. | 435/172.3 |
| 5,439,819 | 8/1995 | Littmann et al. | 435/240.2 |
| 5,447,860 | 9/1995 | Ziegler | 435/240.1 |
| 5,487,979 | 1/1996 | DiFiore et al. | 435/240.2 |
| 5,571,713 | 11/1996 | Lyle et al. | 435/240.2 |
| 5,580,979 | 12/1996 | Bachovchin | 540/509 |
| 5,587,459 | 12/1996 | Uckun | 530/391.1 |
| 5,607,833 | 3/1997 | Gilman et al. | 435/6 |
| 5,618,693 | 4/1997 | McKnight et al. | 435/69.1 |
| 5,627,158 | 5/1997 | Cho-Chung | 514/44 |
| 5,635,177 | 6/1997 | Bennett et al. | 424/143.1 |
| 5,637,463 * | 6/1997 | Dalton et al. | 435/6 |
| 5,652,096 | 7/1997 | Cimino | 435/6 |
| 5,658,791 | 8/1997 | Wilks et al. | 435/331 |
| 5,679,683 | 10/1997 | Bridges et al. | 514/267 |
| 5,681,747 | 10/1997 | Boggs et al. | 435/375 |

FOREIGN PATENT DOCUMENTS

WO 91/02749 * 3/1991 (WO).

OTHER PUBLICATIONS

Results of a GENBANK sequence search and referencfes therein.*
Rui et al., Molecular and Cellular Biology, V.17, No. 11, 6633–6644, 1997.*
Osborne et al., Biotechnology, v.13, 1474–1478, 1995.*
Yokouchi et al., Oncogene, V.15, 7–15, 7/1997.*
Huang et al., PNAS USA, v.92, 11618–11622, 1995.*

Argetsinger et al. (1993) "Identification of JAK2 as a Growth Hormone Receptor–Associated Tyrosine Kinase," Cell 74:237–244.

Marmur and Lane (1960) "Strand Separation and Specific Recombination in Deoxyribonucleic Acids: Biological Studies," Proc. Natl. Acad. Sci. USA 46:453.

Doty et al. (1960) "Strand Separation and Specific Recombination in Deoxyribonucleic Acids: Physcal Chemical Studies," Proc. Natl. Acad. Sci. USA 46:461–476.

Wallace et al. (1985) "Application of synethetic oligonucleotides to the diagnosis of human genetic diseases," Biochimie 67:755–762.

Studencki and Wallace (1984) "Allele–Specific Hybridization Using Oligonucleotide Probes of Very High Specific Activity: Discrimination of the Human $\beta^A$– and $\beta^S$–Globin Genes," DNA 3:7–15.

Studencki et al. (1985) "Discrimination Among the Human, $\beta^A$, $\beta^S$, and $\beta^C$–Globin Genes Using Allele–Specific Oligonucleotide Hybridization Probes," Human Genetics 37:42–51.

Smith and Waterman (1981) "Comparison of Bioseqences," Adv. Appl. Math. 2: 482–489.

Needleman and Wunsch (1970) "A General Method Applicable to the Search for Similarities in the Amino Acid Sequence of Two Proteins," J. Mol. Biol. 48: 443–453.

Pearson and Lipman (1988) "Improved Tools for biological sequence comparison," Proc. Natl. Acad. Sci. USA 85: 2444–2448.

Ihle (1995) "The *Janus* Protein Tyrosine Kinase Family and Its Role in Cytokine Signaling," Adv. Immunol. 60:1–35.

Feng et al. (1997) "Activation of Jak2 Catalytic Activity Requires Phosphorylation of $Y^{1007}$ in the Kinase Activation Loop," Mol. Cell Biol. 17:2497–2501.

Argetsinger and Carter–Su (1996) "Mechanism of Signaling by Growth Hormone Receptor," Physiol. Rev. 76:4: 1089–1107.

Smit et al., "Molecular events in growth hormone—receptor interaction and signaling," in *Handbook of Physiology*, (Section 7) 5, pp. 445–480, Publ. Oxford Univ. Press.

Yokouchi et al. (1997) "Cloning and characterization of APS, an adaptor molecule containing PH and SH2 domains that is tyrosine phosphorylated upon β–cell receptor stimulation," Oncogene 15:7–15.

(List continued on next page.)

Primary Examiner—Bennett Celsa
(74) Attorney, Agent, or Firm—Medlen & Carroll, LLP

(57) ABSTRACT

The invention generally relates to compositions and methods for identifying cytokine, hormone and growth factor signaling pathway agonists and antagonists, and more particularly, methods and compositions for screening compounds and identifying compounds that will modulate the interactions of cytokine, hormone and growth factor receptors with their intracellular ligands, as well as between their intracellular ligands and other members of the signaling pathway.

5 Claims, 40 Drawing Sheets

OTHER PUBLICATIONS

Craparo et al. (1995) "Non–SH2 Domains within Insulin Receptor Substrate–1 and SHC Mediate Their Phosphotyrosine–dependent Interaction with the NPEY Motif of the Insulin–like Growth Factor I Receptor," J. Biol. Chem. 270:15639–15643.

O'Neill et al. (1994) "Characterization of an Interaction between Insulin Receptor Substrate 1 and the Insulin Receptor by Using the Two–Hybrid System," Mol. Cell. Biol. 14:6433–6442.

Zervos et al. (1994) "Mxi1, a Protein That Specifically Interacts with Max to Bind Myc–Max Recognition Sites," Cell 72:223–232.

Guan and Dixon (1991) "Eukaryotic Proteins Expressed in *Escherichia coli:* An Improved Thrombin Clevage and Purification Procedure of Fusion Proteins with Glutathione S–Transferase," Anal. Biochem. 192, 262–267.

Ausubel (1996) in *Current protocols in Molecular Biology,* pp. 9.1.4–11.

GenBank sequence accession No. U57391, Jun. 05, 1996.

Frederick M. Ausubel, *Current protocols in molecular biology,* 1996: 14.3.11, and 5.1.9.

Fakler et al., (1994) "Short Antisense Oligonucleotide–mediated Inhibition Is Strongly Dependent on Oligo Length and Concentration but Almost Independent of Location of the Target Sequence," J. Biol. Chem. 269:16187–16194.

Lane and Harlow Antibody Laboratory Manual, 5:72–76, Cold Spring Harbor (1988), p. 76.

Boehringer Mannheim, Triton® X–100, 1998 Cat. No. 1332 481.

Argetsinger et al. (1993) "Identification of JAK1 as the Growth Hormone Receptor–Associated Tyrosine Kinase," 75th Annual Meeting of The Endocrine Society, Program and Abstracts, Las Vegas, NV, Abstract 34B, pg 59.

Carter–Su (1993) "Molecular Basis of Growth Hormone Action," Clinical Courier 11:14–15.

Chandler et al. (1991) "Identification and Characterization of Rat Intestinal Keratins," J. Biol. Chem. 266:11932–11938.

Endo et al. (1997) "A new protein containing an SH2 domain that inhibits JAK kinases," Nature 387:921–924.

Guo et al. (1995) "Transient Transfection of $GGH_3$–1' Cells [GH3 Cells Stably Tranfected with the Gonadotropin–Releasing Hormone (GnRH) Receptor Complementary Deoxyribonucleic Acid] with the Carboxyl–Terminal of β–Adrenergic Receptor Kinase 1 Blocks Prolactin Release: Evidence for a Role of the G Protein βγ–Subunit Complex in GnRH Signal Transduction," Endocrinology 136:3031–3036.

Ihle (1995) "Cytokine receptor signalling," Nature 377:591–594.

Matsumoto et al. (1997) "CIS, a Cytokine Inducible SH2 Protein, Is a Target of the JAK–STAT5 Pathway and Modulates STAT5 Activation," Blood 89:3148–3154.

Montgomery et al. (1996) "Herpes Simplex Virus–1 Entry into Cells Mediated by a Novel Member of the TNF/NGF Receptor Family," Cell 87:427–436.

Müller et al. (1993) "The protein tyrosine kinase JAK1 complements defects in interferon–α/β and –γ signal trandduction," Nature 366:129–135.

Naka et al. (1997) "Structure and function of a new STAT–induced STAT inhbitor," Nature 387:924–927.

Osborne et al. (1995) "The Yeast Tribrid System—Genetic Detection of trans–phosphorylated ITAM–SH2–Interactions," Biotech. 13:1474–1478.

Riedel et al. (1997) "PSM, an Insulin–Dependent, Pro–Rich, PH, SH2 Domain Containing Partner of the Insulin Receptor," J. Biochem. 122:111–119.

Rui et al. (1997) "Identification of SH2–Bβ as a substrate of the tyrosine kinase JAK2 involved in growth hormone signaling," Mol. Cell. Biol. 17(11):6633–44.

Starr et al. (1997) "A family of cytokine–inducible inhibitors of signalling," Nature 387:917–921.

Wang et al. (1993) Evidence for Involvement of Growth Hormone Receptor Tyrosyl Residues 333 and/or 338 in Actions of Growth Hormone, 75th Annual Meeting of The Endocrine Society, Program and Abstracts, Las Vegas, NV, Abstract 33B.

* cited by examiner

| prey | bait | reporter LacZ | reporter Leu |
|---|---|---|---|
| SH2-Bβc | LexA-JAK2 | + | + |
| | LexA-JAK2(K882E) | - | - |
| | LexA-ΔJAK2 | + | + |
| | LexA-ΔJAK2(K882E) | - | - |

FIG. 1C

ATGAATGGTG CCCCTTCCCC AGAGGATGGG GTTTTCCCTT CTCCACCAGC

GCTGCCACCA CCCCCTCCCC CAAGTTGGCA AGAGTTCTGT GAGTCCCATG

CGAGGGCTGC TGCCCTGGAT CTTGCTCGCC GTTTTCGCCT CTATCTGGCC

TCCCACCCAC AATATGCAGA GCCGGGAGCA GAGGCTGCCTTTTCTGGCCG

TTTTGCTGAG CTCTTCCTGC AGCACTTCGA AGCTGAGGTG GCTCGGGCCT

CGGGCTCACT CTCCCCACCT GTCTTGGCTC CATTGAGCCC TGGTGTGGAA

ATCCCACCAT CACATGACCT GTCCCTTGAG AGCTGCAGGGTGGGTGGGCC

CCTGGCAGTG TTGGGCCCTT CTCGATCTTC TGAGGACCTG GCTGGCCCCC

TTCCTTCCTC AGTCTCTTCC TCTACAACGT CCTCAAAGCC GAAGCTCAAG

AAACGCTTCT CCCTCCGCTC GGTGGGTCGT TCAGTCAGAG GTTCTGTCCG

AGGCATCCTG CAGTGGCGGG GGGCTGTTGA ATCTCCCTCCCAAGCTGGGC

CTCTGGAGAC CACATCAGGT CCTCCAGTTC TAGGTGGAAACAGCAACTCC

AACTCCTCTG GTGGTGCTGG GACAGTTGGTAAGGCATTGGCCAACGATGG

CACATCCCCT GGGGAGAGAT GGACTCATCGCTTTGAGAGGCTAAGGCTAA

GTCGTGGAGG GGGAACCTTG AGAGACGGAG CAGGAGTGATACAGAGAGAA

GAGCTGCTGA GTTTCATGGG GGCTGAAGAG GCTGCCCCTG ACCCAGCAGG

AGTAGGTCGT GGAGGAGGGG CAGCTGGGCT GACCTCGGGA GGAGGAGGGC

AGCCTCAGTG GCAGAAATGT CGATTACTGC TCCGGAGTGA AGGAGAAGGA

GGAGGAGGAA GTCGCTTGGA GTTCTTTGTA CCACCCAAGG CATCCCGGCC

CCGTCTTAGC ATTCCCTGTT CTACTATTAC TGATGTCCGC ACAGCCACAG

CCCTGGAGAT GCCTGACAGG GAGAACACGT TTGTGGTTAAGGTAGAAGGC

CCTTCAGAGT ACATCCTGGA GACAACTGAT GCACTTCATG TGAAGGCCTG

GGTGTCTGAC ATCCAAGAGT GCCTAAGCCC AGGACCCTGC CCTGCTATCA

GCCCCCGTCC CATGACCCTT CCCCTGGCCC CTGGGACCTC CTTCCTCACA

Figure 2A

AAGGATAACA CAGAGAGCCT GGAGTTGCCC TGCCTGAATC ATTCAGAGAG

TCTGCCTAGC CAGGATCTTC TTCTGGGACC CAGCGAGAGT AACGACCGCC

TGTCGCAGGG AGCTTATGGA GGCCTCTCAG ACCGGCCGTC AGCGTCCTTC

TCCCCTAGTT CTGCCTCCAT TGCTGCTTCC CATTTTGACT CAATGGAACT

GCTTCCTCCA GAGTTGCCCC CTCGGATTCC CATTGAGGAG GGGCCTCCAG

CAGGGACAGT TCATCCCCTC TCTACCCCGT ACCCTCCCCT GGATACTCCT

GAAGCAGCCA CAGGGTCATT CCTCTTTCAA GGGGAGGCAG AGGGGGGTGA

GGGGGACCAG CCCCTCTCAG GCTACCCTTG GTTCCACGGC ATGCTCTCTC

GGCTCAAAGC TGCCCAGTTA GTGTTAGAAG GAGGTACCAG CTCCCATGGT

GTCTTCTTGG TACGCCAGAG TGAGACAAGA CGTGGTGAAT ATGTCCTCAC

TTTCAACTTC CAGGGCAAGG CTAAGCACCT GCGTTTGTCA CTAAATGAGG

AGGGTCAGTG CCGGGTCCAA CATCTGTGGT TCCAGTCCAT TTTCGATATG

CTTGAGCACT TCCGGGTGCA CCCCATCCCT CTGGAGTCTG GAGGCTCCAG

TGATGTTGTC CTTGTCAGCT ATGTGCCCTC CCAGCGGCAG CAGGGCCGGG

AGCAGGCTGG GAGCCATGCA GGGGTGTGCG AGGGCGACCG ATGCTACCCC

GATGCTTCTT CCACCTTCCT GCCCTTCGGA GCGAGTGACT GTGTAACGGA

GCACTTCCCG TGATCCAACC CAGCCTTCTG AACCCCCTCC ATGGACAGAT

CCCCCACATC CTGGGGCAGA AGAGGCGTCG GGGGCGCCAG AAGTGGCGGC

AGCCACAGCC GCAGCAGCCA AAGAGAGGCA AGAGAAGGAG AAAGCGGGCG

GCGGAGGGGT CCAGGAAGAG CTGGTCCCCA TGGCTGAGCT GGTCCCCATG

GCTGAATTGG AAGAGGCCAT AGCACCAGGC ACTGAGGCTC AGGGTGGTGC

TGGCTCTAGT GGGGACTTGG AGGTGTCCCT AATGGTTCAG CTCCAGCAGT

TACCACTAGG GGGCAACGGA GAAGAAGGGG GTCACCCCCG AGCCATTAAT

AACCAGTACT CATTTGTCTG AGA

Figure 2A

MNGAPSPEDG VFPSPPALPP PPPPSWQEFC ESHARAAALD LARRFRLYLA

SHPQYAEPGA EAAFSGRFAE LFLQHFEAEV ARASGSLSPP VLAPLSPGVE

IPPSHDLSLE SCRVGGPLAV LGPSRSSEDL AGPLPSSVSS STTSSKPKLK

KRFSLRSVGR SVRGSVRGIL QWRGAVESPS QAGPLETTSG PPVLGGNSNS

NSSGGAGTVG KALANDGTSP GERWTHRFER LRLSRGGGTL RDGAGVIQRE

ELLSFMGAEE AAPDPAGVGR GGGAAGLTSG GGGQPQWQKCRLLLRSEGEG

GGGSRLEFFV PPKASRPRLS IPCSTITDVR TATALEMPDR ENTFVVKVEG

PSEYILETTD ALHVKAWVSD IQECLSPGPC PAISPRPMTL PLAPGTSFLT

KDNTESLELP CLNHSESLPS QDLLLGPSES NDRLSQGAYG GLSDRPSASF

SPSSASIAAS HFDSMELLPP ELPPRIPIEE GPPAGTVHPL STPYPPLDTP

EAATGSFLFQ GEAEGGEGDQ PLSGYPWFHG MLSRLKAAQL VLEGGTSSHG

VFLVRQSETR RGEYVLTFNF QGKAKHLRLS LNEEGQCRVQ HLWFQSIFDM

LEHFRVHPIP LESGGSSDVV LVSYVPSQRQ QGREQAGSHA GVCEGDRCYP

DASSTFLPFG ASDCVTEHFP

Figure 2B

```
CTG CTT GAT GAC TTT GTC ATG TCT TAC CTT TCC CCT CAG TGG CGG
Leu Leu Asp Asp Phe Val Met Ser Tyr Leu Ser Pro Gln Trp Arg
 1           5                   10                  15

CAT GAT TTT GTT CAC GGA TGG ATA AAA GTA CCT GTG ACT CAT GAA
His Asp Phe Val His Gly Trp Ile Lys Val Pro Val Thr His Glu
             20                  25                  30

ACT CAG GAA GAG TGT CTT GGG ATG GCG GTG TTA GAC ATG ATG AGA
Thr Gln Glu Glu Cys Leu Gly Met Ala Val Leu Asp Met Met Arg
             35                  40                  45

ATA GCT AAG GAG AAA GAC CAG ACT CCA CTG GCT GTC TAT AAC TCT
Ile Ala Lys Glu Lys Asp Gln Thr Pro Leu Ala Val Tyr Asn Ser
             50                  55                  60

GTC AGC TAC AAG ACA TTC TTA CCA AAG TGC GTT CGA GCG AAG ATC
Val Ser Tyr Lys Thr Phe Leu Pro Lys Cys Val Arg Ala Lys Ile
             65                  70                  75

CAA GAC TAT CAC ATT TTA ACC CGG AAG CGA ATC AGG TAC AGA TTT
Gln Asp Tyr His Ile Leu Thr Arg Lys Arg Ile Arg Tyr Arg Phe
             80                  85                  90

CGC AGA TTC ATT CAG CAA TTC AGT CAA TGT AAA GCC ACT GCC AGG
Arg Arg Phe Ile Gln Gln Phe Ser Gln Cys Lys Ala Thr Ala Arg
             95                  100                 105

AAC CTA AAA CTT AAG TAT CTT ATA AAC CTG GAA ACC CTG CAG TCT
Asn Leu Lys Leu Lys Tyr Leu Ile Asn Leu Glu Thr Leu Gln Ser
             110                 115                 120

GCC TTC TAC ACA GAA CAG TTT GAA GTA AAA GAA TCT GCA AGA GGT
Ala Phe Tyr Thr Glu Gln Phe Glu Val Lys Glu Ser Ala Arg Gly
             125                 130                 135

CCT TCA GGT GAG GAG ATT TTT GCA ACC ATT ATA ATA ACT GGA AAC
Pro Ser Gly Glu Glu Ile Phe Ala Thr Ile Ile Ile Thr Gly Asn
             140                 145                 150

GGT GGA ATT CAG TGG TCA AGA GGG AAA CAT AAG GAA AGT GAG ACA
Gly Gly Ile Gln Trp Ser Arg Gly Lys His Lys Glu Ser Glu Thr
             155                 160                 165
```

Figure 3A

```
CTG ACA GAA CAG GAC GTA CAG TTA TAT TGT GAT TTC CCT GAT ATT
Leu Thr Glu Gln Asp Val Gln Leu Tyr Cys Asp Phe Pro Asp Ile
            170             175             180

ATT GAT GTC AGT ATT AAG CAA GCA AAT CAG GAA TGC TCA ACT GAA
Ile Asp Val Ser Ile Lys Gln Ala Asn Gln Glu Cys Ser Thr Glu
            185             190             195

AGT AGA GTT GTG ACC GTC CAC AAG CAG GAC GGG AAG GTC TTG GAA
Ser Arg Val Val Thr Val His Lys Gln Asp Gly Lys Val Leu Glu
            200             205             210

ATA GAA CTT AGC TCA TTA AAA GAA GCC TTG TCA TTC GTG TCA TTA
Ile Glu Leu Ser Ser Leu Lys Glu Ala Leu Ser Phe Val Ser Leu
            215             220             225

ATT GAC GGG TAT TAC AGA CTA ACT GCG GAT GCA CAC CAT TAC CTC
Ile Asp Gly Tyr Tyr Arg Leu Thr Ala Asp Ala His His Tyr Leu
            230             235             240

TGC AAA GAG GTG GCT CCC CCA GCT GTG TTC GAG AAC ATA CAC AGC
Cys Lys Glu Val Ala Pro Pro Ala Val Phe Glu Asn Ile His Ser
            245             250             255

AAC TGC CAC GGC CCA ATT TCA ATG GAT TTT GCC ATC AGC AAA CTA
Asn Cys His Gly Pro Ile Ser Met Asp Phe Ala Ile Ser Lys Leu
            260             265             270

AAG AAG GCA GGA AAC CAG ACT GGA CTG TAT GTA CTT CGA TGT AGC
Lys Lys Ala Gly Asn Gln Thr Gly Leu Tyr Val Leu Arg Cys Ser
            275             280             285

CCT AAG GAC TTC AAC AAA TAC TTC CTG ACC TTT GCC GTT GAG CGA
Pro Lys Asp Phe Asn Lys Tyr Phe Leu Thr Phe Ala Val Glu Arg
            290             295             300

GAA AAT GTT ATT GAA TAT AAA CAC TGT TTG ATT ACA AAG AAT GAG
Glu Asn Val Ile Glu Tyr Lys His Cys Leu Ile Thr Lys Asn Glu
            305             310             315
```

Figure 3A

```
AAT GGA GAG TAC AAC CTC AGT GGG ACT AAG AGG AAC TTC AGT AGT
Asn Gly Glu Tyr Asn Leu Ser Gly Thr Lys Arg Asn Phe Ser Ser
                320                 325                 330

CTT AAG GAC CTT TTG AAT TGC TAC CAG ATG GAA ACT GTG CGC TCA
Leu Lys Asp Leu Leu Asn Cys Tyr Gln Met Glu Thr Val Arg Ser
                335                 340                 345

GAC AGT ATC ATC TTC CAG TTC ACC AAA TGC TGT CCT CCA AAG CCG
Asp Ser Ile Ile Phe Gln Phe Thr Lys Cys Cys Pro Pro Lys Pro
                350                 355                 360

AAA GAT AAA TCA AAC CTT CTT GTC TTC AGA ACA AAT GGT GTT TCT
Lys Asp Lys Ser Asn Leu Leu Val Phe Arg Thr Asn Gly Val Ser
                365                 370                 375

GAT GTT CAG CTC TCA CCA ACA TTA CAG AGG CAT AAT AAT GTG AAT
Asp Val Gln Leu Ser Pro Thr Leu Gln Arg His Asn Asn Val Asn
                380                 385                 390

CAA ATG GTG TTT CAC AAA ATC AGG AAT GAA GAT TTG ATA TTT AAT
Gln Met Val Phe His Lys Ile Arg Asn Glu Asp Leu Ile Phe Asn
                395                 400                 405
         Iₐ
GAA AGC CTT GGC CAA GGC ACT TTT ACA AAA ATA TTT AAA GGT GTA
Glu Ser Leu Gly Gln Gly Thr Phe Thr Lys Ile Phe Lys Gly Val
                410                 415                 420

AGA AGA GAA GTT GGA GAT TAT GGT CAG CTG CAC GAA ACC GAA GTT
Arg Arg Glu Val Gly Asp Tyr Gly Gln Leu His Glu Thr Glu Val
                425                 430                 435
   IIₐ
CTT TTG AAA GTC CTA GAT AAA GCA CAT AGA AAC TAT TCA GAG TCT
Leu Leu Lys Val Leu Asp Lys Ala His Arg Asn Tyr Ser Glu Ser
                440                 445                 450
   IIIₐ
TTC TTT GAA GCA GCA AGC ATG ATG AGT CAG CTT TCT CAC AAG CAT
Phe Phe Glu Ala Ala Ser Met Met Ser Gln Leu Ser His Lys His
                455                 460                 465
```

Figure 3A

IV_a
TTG GTT TTG AAT TAT GGA GTA TGT GTC TGT GGA GAG GAG AAC ATT
Leu Val Leu Asn Tyr Gly Val Cys Val Cys Gly Glu Glu Asn Ile
            470             475             480

TTG GTT CAA GAG TTT GTA AAA TTT GGA TCA CTG GAT ACA TAC CTG
Leu Val Gln Glu Phe Val Lys Phe Gly Ser Leu Asp Thr Tyr Leu
            485             490             495

AAG AAG AAC AAA AAT TCT ATA AAT ATA TTA TGG AAA CTT GGA GTG
Lys Lys Asn Lys Asn Ser Ile Asn Ile Leu Trp Lys Leu Gly Val
            500             505             510

GCG AAG CAG TTG GCA TGG GCC ATG CAC TTC CTC GAA GAA AAA TCC
Ala Lys Gln Leu Ala Trp Ala Met His Phe Leu Glu Glu Lys Ser
            515             520             525
                VI_a
CTT ATT CAT GGG AAT GTG TGT GCT AAA AAT ATC CTG CTT ATC AGA
Leu Ile His Gly Asn Val Cys Ala Lys Asn Ile Leu Leu Ile Arg
            530             535             540

GAA GAA GAC AGG AGA ACG GGG AAC CCA CCT TTC ATC AAA CTT AGT
Glu Glu Asp Arg Arg Thr Gly Asn Pro Pro Phe Ile Lys Leu Ser
            545             550             555
VII_a
GAT CCT GGC ATT AGC ATT ACA GTT CTA CCG AAG GAC ATT TCT TCC
Asp Pro Gly Ile Ser Ile Thr Val Leu Pro Lys Asp Ile Ser Ser
            560             565             570
                                            VIII_a
TGT TGT TTC CAA GTT CTT CAG GAG AGA ATA CCA TGG GTA CCA CCT
Cys Cys Phe Gln Val Leu Gln Glu Arg Ile Pro Trp Val Pro Pro
            575             580             585

GAG TGC ATT GAG AAT CCT AAA AAT CTA ACT CTG GCA ACA GAC AAG
Glu Cys Ile Glu Asn Pro Lys Asn Leu Thr Leu Ala Thr Asp Lys
            590             595             600
        IX_a
TGG AGC TTC GGG ACC ACT CTG TGG GAG ATC TGC AGT GGA GGA GAT
Trp Ser Phe Gly Thr Thr Leu Trp Glu Ile Cys Ser Gly Gly Asp
            605             610             615

Figure 3A

```
AAG CCC CTG AGT GCT CTG GAT TCT CAA AGA AAG CTG CAG TTC TAT
Lys Pro Leu Ser Ala Leu Asp Ser Gln Arg Lys Leu Gln Phe Tyr
            620                 625                 630
                Xa
GAA GAT AAG CAT CAG CTT CCT GCA CCC AAG TGG ACA GAG TTG GCA
Glu Asp Lys His Gln Leu Pro Ala Pro Lys Trp Thr Glu Leu Ala
            635                 640                 645
                                    XIa
AAC CTT ATA AAT AAT TGC ATG GAC TAT GAG CCA GAT TTC AGG CCT
Asn Leu Ile Asn Asn Cys Met Asp Tyr Glu Pro Asp Phe Arg Pro
            650                 655                 660

GCT TTC AGA GCT GTC ATC CGT GAT CTT AAC AGC CTG TTT ACT CCA
Ala Phe Arg Ala Val Ile Arg Asp Leu Asn Ser Leu Phe Thr Pro
            665                 670                 675

GAT TAT GAA CTA CTA ACA GAA AAT GAC ATG CTA CCA AAC ATG AGA
Asp Tyr Glu Leu Leu Thr Glu Asn Asp Met Leu Pro Asn Met Arg
            680                 685                 690

ATA GGT GCC CTA GGG TTT TCT GGT GCT TTT GAA GAC AGG GAC CCT
Ile Gly Ala Leu Gly Phe Ser Gly Ala Phe Glu Asp Arg Asp Pro
            695                 700                 705

ACA CAG TTT GAA GAG AGA CAC TTG AAG TTT CTA CAG CAG CTT GGC
Thr Gln Phe Glu Glu Arg His Leu Lys Phe Leu Gln Gln Leu Gly
            710                 715                 720
 I
AAA GGT AAC TTC GGG AGT GTG GAG ATG TGC CGC TAT GAC CCG CTG
Lys Gly Asn Phe Gly Ser Val Glu Met Cys Arg Tyr Asp Pro Leu
            725                 730                 735
                                            II
CAG GAC AAC ACT GGC GAG GTG GTC GCT GTG AAG AAA CTC CAG CAC
Gln Asp Asn Thr Gly Glu Val Val Ala Val Lys Lys Leu Gln His
            740                 745                 750
                                        III
AGC ACT GAA GAG CAC CTC CGA GAC TTT GAG AGG GAG ATC GAG ATC
Ser Thr Glu Glu His Leu Arg Asp Phe Glu Arg Glu Ile Glu Ile
            755                 760                 765
                    IV
CTG AAA TCC TTG CAG CAT GAC AAC ATC GTC AAG TAC AAG GGA GTG
Leu Lys Ser Leu Gln His Asp Asn Ile Val Lys Tyr Lys Gly Val
            770                 775                 780
```

Figure 3A

```
TGC TAC AGT GCG GGT CGG CGC AAC CTA AGA TTA ATT ATG GAA TAT
Cys Tyr Ser Ala Gly Arg Arg Asn Leu Arg Leu Ile Met Glu Tyr
            785                 790                 795
        V
TTA CCA TAT GGA AGT TTA CGA GAC TAT CTC CAA AAA CAT AAA GAA
Leu Pro Tyr Gly Ser Leu Arg Asp Tyr Leu Gln Lys His Lys Glu
            800                 805                 810

CGG ATA GAT CAC AAA AAA CTT CTT CAA TAC ACA TCT CAG ATA TGC
Arg Ile Asp His Lys Lys Leu Leu Gln Tyr Thr Ser Gln Ile Cys
            815                 820                 825

AAG GGC ATG GAA TAT CTT GGT ACA AAA AGG TAT ATC CAC AGG GAC
Lys Gly Met Glu Tyr Leu Gly Thr Lys Arg Tyr Ile His Arg Asp
            830                 835                 840
VI
CTG GCA ACA AGG AAC ATA TTG GTG GAA AAT GAG AAC AGG GTT AAA
Leu Ala Thr Arg Asn Ile Leu Val Glu Asn Glu Asn Arg Val Lys
            845                 850                 855
        VII
ATA GGA GAC TTC GGA TTA ACC AAA GTC TTG CCG CAG GAC AAA GAA
Ile Gly Asp Phe Gly Leu Thr Lys Val Leu Pro Gln Asp Lys Glu
            860                 865                 870

TAC TAC AAA GTA AAG GAG CCA GGG GAA AGC CCC ATA TTC TGG TAC
Tyr Tyr Lys Val Lys Glu Pro Gly Glu Ser Pro Ile Phe Trp Tyr
            875                 880                 885
VIII
GCA CCT GAA TCC TTG ACG GAG AGC AAG TTT TCT GTG GCC TCA GAT
Ala Pro Glu Ser Leu Thr Glu Ser Lys Phe Ser Val Ala Ser Asp
            890                 895                 900
        IX
GTG TGG AGC TTT GGA GTG GTT CTA TAC GAA CTT TTC ACA TAC ATC
Val Trp Ser Phe Gly Val Val Leu Tyr Glu Leu Phe Thr Tyr Ile
            905                 910                 915

GAG AAG AGT AAA AGT CCA CCC GTG GAA TTT ATG CGA ATG ATT GGC
Glu Lys Ser Lys Ser Pro Pro Val Glu Phe Met Arg Met Ile Gly
            920                 925                 930

AAT GAT AAA CAA GGG CAA ATG ATT GTG TTC CAT TTG ATA GAG CTA
Asn Asp Lys Gln Gly Gln Met Ile Val Phe His Leu Ile Glu Leu
            935                 940                 945
```

Figure 3A

```
                                  X
CTG AAG AGC AAC GGA AGA TTG CCA AGG CCA GAA GGA TGC CCA GAT
Leu Lys Ser Asn Gly Arg Leu Pro Arg Pro Glu Gly Cys Pro Asp
                950                 955                 960

GAG ATT TAT GTG ATC ATG ACA GAG TGC TGG AAC AAC AAT GTG AGC
Glu Ile Tyr Val Ile Met Thr Glu Cys Trp Asn Asn Asn Val Ser
                965                 970                 975
         XI
CAG CGT CCC TCC TTC AGG GAC CTT TCC TTC GGG TGG ATC AAA TCC
Gln Arg Pro Ser Phe Arg Asp Leu Ser Phe Gly Trp Ile Lys Ser
                980                 985                 990

GGG ACA GTA TAGCTGCGTG AAAGAGATGG CCTTACTCAG AGACCAAGCA
Gly Thr Val
```

GACTTCCAGA ACCAGAACAA AGCTCTGTAG CCTTGTGTCT ACACATCCTT

ATCATGACGC TAGCTAGGCA GAAAGAAAAC TGTGACGCCG TCTGCTCAAA

AGCTTTGGAA AACGCCGTGC AGGTTTGTTT CATCACCATC TGTAAAAACC

ACTGCTCAAG TCTGGCAGCA TGCTTGTGGG CTGATGCATG GAGCTCACCA

CAGAGTCTCT GCATCTCCTC TGACAGAAGA AGAAAAATAG ACAATTTTCA

ACTCACTTTT TTGAGAAATG GAAAAAAATT ATAATGTAAA TTTTTCAGTG

TAGGAAATAC ACAGAACATA CATGTACAGT TTTTACCACG TGGAGTGTAT

AATACTTTGG CCTCTTGTGT GATTTACATG AGGGCTGATG TTTGTTAATG

TTTTCTAATT TTTCCATAGG TGATCTATAA TAACTTCATG ATACAAATTA

AAATGCTCAG AAAATTAAAA AAAAAA

Figure 3A

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 2373 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO: 1:

ATGAATGGTG CCCCTTCCCC AGAGGATGGG GTTTTCCCTT CTCCACCAGC GCTGCCACCA    60

```
CCCCCTCCCC CAAGTTGGCA AGAGTTCTGT GAGTCCCATG CGAGGGCTGC TGCCCTGGAT    120
CTTGCTCGCC GTTTTCGCCT CTATCTGGCC TCCCACCCAC AATATGCAGA GCCGGGAGCA    180
GAGGCTGCCT TTTCTGGCCG TTTTGCTGAG CTCTTCCTGC AGCACTTCGA AGCTGAGGTG    240
GCTCGGGCCT CGGGCTCACT CTCCCCACCT GTCTTGGCTC CATTGAGCCC TGGTGTGGAA    300
ATCCCACCAT CACATGACCT GTCCCTTGAG AGCTGCAGGG TGGGTGGGCC CCTGGCAGTG    360
TTGGGCCCTT CTCGATCTTC TGAGGACCTG GCTGGCCCCC TTCCTTCCTC AGTCTCTTCC    420
TCTACAACGT CCTCAAAGCC GAAGCTCAAG AAACGCTTCT CCCTCCGCTC GGTGGGTCGT    480
TCAGTCAGAG GTTCTGTCCG AGGCATCCTG CAGTGGCGGG GGGCTGTTGA ATCTCCCTCC    540
CAAGCTGGGC CTCTGGAGAC CACATCAGGT CCTCCAGTTC TAGGTGGAAA CAGCAACTCC    600
AACTCCTCTG GTGGTGCTGG GACAGTTGGT AAGGCATTGG CCAACGATGG CACATCCCCT    660
GGGGAGAGAT GGACTCATCG CTTTGAGAGG CTAAGGCTAA GTCGTGGAGG GGGAACCTTG    720
AGAGACGGAG CAGGAGTGAT ACAGAGAGAA GAGCTGCTGA GTTTCATGGG GGCTGAAGAG    780
GCTGCCCCTG ACCCAGCAGG AGTAGGTCGT GGAGGAGGGG CAGCTGGGCT GACCTCGGGA    840
GGAGGAGGGC AGCCTCAGTG GCAGAAATGT CGATTACTGC TCCGGAGTGA AGGAGAAGGA    900
GGAGGAGGAA GTCGCTTGGA GTTCTTTGTA CCACCCAAGG CATCCCGGCC CGTCTTAGC    960
ATTCCCTGTT CTACTATTAC TGATGTCCGC ACAGCCACAG CCCTGGAGAT GCCTGACAGG   1020
GAGAACACGT TTGTGGTTAA GGTAGAAGGC CCTTCAGAGT ACATCCTGGA CAACTGAT    1080
GCACTTCATG TGAAGGCCTG GGTGTCTGAC ATCCAAGAGT GCCTAAGCCC AGGACCCTGC   1140
CCTGCTATCA GCCCCCGTCC CATGACCCTT CCCCTGGCCC CTGGGACCTC CTTCCTCACA   1200
AAGGATAACA CAGAGAGCCT GGAGTTGCCC TGCCTGAATC ATTCAGAGAG TCTGCCTAGC   1260
CAGGATCTTC TTCTGGGACC CAGCGAGAGT AACGACCGCC TGTCGCAGGG AGCTTATGGA   1320
GGCCTCTCAG ACCGGCCGTC AGCGTCCTTC TCCCCTAGTT CTGCCTCCAT TGCTGCTTCC   1380
CATTTTGACT CAATGGAACT GCTTCCTCCA GAGTTGCCCC CTCGGATTCC CATTGAGGAG   1440
GGGCCTCCAG CAGGGACAGT TCATCCCCTC TCTACCCCGT ACCCTCCCCT GGATACTCCT   1500
GAAGCAGCCA CAGGGTCATT CCTCTTTCAA GGGGAGGCAG AGGGGGGTGA GGGGGACCAG   1560
CCCCTCTCAG GCTACCCTTG GTTCCACGGC ATGCTCTCTC GGCTCAAAGC TGCCCAGTTA   1620
GTGTTAGAAG GAGGTACCAG CTCCCATGGT GTCTTCTTGG TACGCCAGAG TGAGACAAGA   1680
CGTGGTGAAT ATGTCCTCAC TTTCAACTTC CAGGGCAAGG CTAAGCACCT GCGTTTGTCA   1740
CTAAATGAGG AGGGTCAGTG CCGGGTCCAA CATCTGTGGT CCAGTCCAT TTTCGATATG    1800
CTTGAGCACT TCCGGGTGCA CCCCATCCCT CTGGAGTCTG GAGGCTCCAG TGATGTTGTC   1860
CTTGTCAGCT ATGTGCCCTC CCAGCGGCAG CAGGGCCGGG AGCAGGCTGG GAGCCATGCA   1920
GGGGTGTGCG AGGGCGACCG ATGCTACCCC GATGCTTCTT CCACCTTCCT GCCCTTCGGA   1980
GCGAGTGACT GTGTAACGGA GCACTTCCCG TGATCCAACC CAGCCTTCTG AACCCCCTCC   2040
ATGGACAGAT CCCCCACATC CTGGGGCAGA AGAGGCGTCG GGGGCGCCAG AAGTGGCGGC   2100
AGCCACAGCC GCAGCAGCCA AAGAGAGGCA AGAGAAGGAG AAAGCGGGCG GCGGAGGGGT   2160
CCAGGAAGAG CTGGTCCCCA TGGCTGAGCT GGTCCCCATG GCTGAATTGG AAGAGGCCAT   2220
AGCACCAGGC ACTGAGGCTC AGGGTGGTGC TGGCTCTAGT GGGGACTTGG AGGTGTCCCT   2280
AATGGTTCAG CTCCAGCAGT TACCACTAGG GGGCAACGGA GAAGAAGGGG GTCACCCCCG   2340
AGCCATTAAT AACCAGTACT CATTTGTCTG AGA                                2373
```

-continued (2) INFORMATION FOR SEQ ID NO: 2:

(i) SEQUENCE CHARACTERISTICS:
        (A) LENGTH: 670 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO: 2:

```
Met Asn Gly Ala Pro Ser Pro Glu Asp Gly Val Phe Pro Ser Pro
1               5                  10                 15

Ala Leu Pro Pro Pro Pro Ser Trp Gln Glu Phe Cys Glu Ser
            20                 25                 30

His Ala Arg Ala Ala Ala Leu Asp Leu Ala Arg Arg Phe Arg Leu Tyr
        35                 40                 45

Leu Ala Ser His Pro Gln Tyr Ala Glu Pro Gly Ala Glu Ala Ala Phe
50                 55                 60

Ser Gly Arg Phe Ala Glu Leu Phe Leu Gln His Phe Glu Ala Glu Val
65                 70                 75                 80

Ala Arg Ala Ser Gly Ser Leu Ser Pro Pro Val Leu Ala Pro Leu Ser
                85                 90                 95

Pro Gly Val Glu Ile Pro Pro Ser His Asp Leu Ser Leu Glu Ser Cys
                100                105                110

Arg Val Gly Gly Pro Leu Ala Val Leu Gly Pro Ser Arg Ser Ser Glu
            115                120                125

Asp Leu Ala Gly Pro Leu Pro Ser Ser Val Ser Ser Thr Thr Ser
        130                135                140

Ser Lys Pro Lys Leu Lys Lys Arg Phe Ser Leu Arg Ser Val Gly Arg
145                150                155                160

Ser Val Arg Gly Ser Val Arg Gly Ile Leu Gln Trp Arg Gly Ala Val
                165                170                175

Glu Ser Pro Ser Gln Ala Gly Pro Leu Glu Thr Thr Ser Gly Pro Pro
            180                185                190

Val Leu Gly Gly Asn Ser Asn Ser Asn Ser Ser Gly Gly Ala Gly Thr
        195                200                205

Val Gly Lys Ala Leu Ala Asn Asp Gly Thr Ser Pro Gly Glu Arg Trp
210                215                220

Thr His Arg Phe Glu Arg Leu Arg Leu Ser Arg Gly Gly Gly Thr Leu
225                230                235                240

Arg Asp Gly Ala Gly Val Ile Gln Arg Glu Glu Leu Leu Ser Phe Met
                245                250                255

Gly Ala Glu Glu Ala Ala Pro Asp Pro Ala Gly Val Gly Arg Gly Gly
            260                265                270

Gly Ala Ala Gly Leu Thr Ser Gly Gly Gly Gln Pro Gln Trp Gln
        275                280                285

Lys Cys Arg Leu Leu Leu Arg Ser Glu Gly Glu Gly Gly Gly Ser
        290                295                300

Arg Leu Glu Phe Phe Val Pro Pro Lys Ala Ser Arg Pro Arg Leu Ser
305                310                315                320

Ile Pro Cys Ser Thr Ile Thr Asp Val Arg Thr Ala Thr Ala Leu Glu
                325                330                335

Met Pro Asp Arg Glu Asn Thr Phe Val Val Lys Val Glu Gly Pro Ser
            340                345                350

Glu Tyr Ile Leu Glu Thr Thr Asp Ala Leu His Val Lys Ala Trp Val
```

-continued

```
              355                 360                 365
Ser Asp Ile Gln Glu Cys Leu Ser Pro Gly Pro Cys Pro Ala Ile Ser
    370                 375                 380

Pro Arg Pro Met Thr Leu Pro Leu Ala Pro Gly Thr Ser Phe Leu Thr
385                 390                 395                 400

Lys Asp Asn Thr Glu Ser Leu Glu Leu Pro Cys Leu Asn His Ser Glu
                405                 410                 415

Ser Leu Pro Ser Gln Asp Leu Leu Gly Pro Ser Glu Ser Asn Asp
                420                 425                 430

Arg Leu Ser Gln Gly Ala Tyr Gly Gly Leu Ser Asp Arg Pro Ser Ala
        435                 440                 445

Ser Phe Ser Pro Ser Ser Ala Ser Ile Ala Ala Ser His Phe Asp Ser
    450                 455                 460

Met Glu Leu Leu Pro Pro Glu Leu Pro Pro Arg Ile Pro Ile Glu Glu
465                 470                 475                 480

Gly Pro Pro Ala Gly Thr Val His Pro Leu Ser Thr Pro Tyr Pro Pro
                485                 490                 495

Leu Asp Thr Pro Glu Ala Ala Thr Gly Ser Phe Leu Phe Gln Gly Glu
                500                 505                 510

Ala Glu Gly Gly Glu Gly Asp Gln Pro Leu Ser Gly Tyr Pro Trp Phe
        515                 520                 525

His Gly Met Leu Ser Arg Leu Lys Ala Ala Gln Leu Val Leu Glu Gly
    530                 535                 540

Gly Thr Ser Ser His Gly Val Phe Leu Val Arg Gln Ser Glu Thr Arg
545                 550                 555                 560

Arg Gly Glu Tyr Val Leu Thr Phe Asn Phe Gln Gly Lys Ala Lys His
                565                 570                 575

Leu Arg Leu Ser Leu Asn Glu Glu Gly Gln Cys Arg Val Gln His Leu
                580                 585                 590

Trp Phe Gln Ser Ile Phe Asp Met Leu Glu His Phe Arg Val His Pro
        595                 600                 605

Ile Pro Leu Glu Ser Gly Gly Ser Ser Asp Val Val Leu Val Ser Tyr
    610                 615                 620

Val Pro Ser Gln Arg Gln Gln Gly Arg Glu Gln Ala Gly Ser His Ala
625                 630                 635                 640

Gly Val Cys Glu Gly Asp Arg Cys Tyr Pro Asp Ala Ser Ser Thr Phe
                645                 650                 655

Leu Pro Phe Gly Ala Ser Asp Cys Val Thr Glu His Phe Pro
                660                 665                 670
```

(2) INFORMATION FOR SEQ ID NO: 3:

(i) SEQUENCE CHARACTERISTICS:
        (A) LENGTH: 3495 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..2979

(xi) SEQUENCE DESCRIPTION: SEQ ID NO: 3:

```
CTG CTT GAT GAC TTT GTC ATG TCT TAC CTT TCC CCT CAG TGG CGG CAT      48
Leu Leu Asp Asp Phe Val Met Ser Tyr Leu Ser Pro Gln Trp Arg His
  1               5                  10                  15
```

-continued

```
GAT TTT GTT CAC GGA TGG ATA AAA GTA CCT GTG ACT CAT GAA ACT CAG        96
Asp Phe Val His Gly Trp Ile Lys Val Pro Val Thr His Glu Thr Gln
         20                  25                  30

GAA GAG TGT CTT GGG ATG GCG GTG TTA GAC ATG ATG AGA ATA GCT AAG       144
Glu Glu Cys Leu Gly Met Ala Val Leu Asp Met Met Arg Ile Ala Lys
             35                  40                  45

GAG AAA GAC CAG ACT CCA CTG GCT GTC TAT AAC TCT GTC AGC TAC AAG       192
Glu Lys Asp Gln Thr Pro Leu Ala Val Tyr Asn Ser Val Ser Tyr Lys
     50                  55                  60

ACA TTC TTA CCA AAG TGC GTT CGA GCG AAG ATC CAA GAC TAT CAC ATT       240
Thr Phe Leu Pro Lys Cys Val Arg Ala Lys Ile Gln Asp Tyr His Ile
 65                  70                  75                  80

TTA ACC CGG AAG CGA ATC AGG TAC AGA TTT CGC AGA TTC ATT CAG CAA       288
Leu Thr Arg Lys Arg Ile Arg Tyr Arg Phe Arg Arg Phe Ile Gln Gln
                 85                  90                  95

TTC AGT CAA TGT AAA GCC ACT GCC AGG AAC CTA AAA CTT AAG TAT CTT       336
Phe Ser Gln Cys Lys Ala Thr Ala Arg Asn Leu Lys Leu Lys Tyr Leu
            100                 105                 110

ATA AAC CTG GAA ACC CTG CAG TCT GCC TTC TAC ACA GAA CAG TTT GAA       384
Ile Asn Leu Glu Thr Leu Gln Ser Ala Phe Tyr Thr Glu Gln Phe Glu
        115                 120                 125

GTA AAA GAA TCT GCA AGA GGT CCT TCA GGT GAG GAG ATT TTT GCA ACC       432
Val Lys Glu Ser Ala Arg Gly Pro Ser Gly Glu Glu Ile Phe Ala Thr
    130                 135                 140

ATT ATA ATA ACT GGA AAC GGT GGA ATT CAG TGG TCA AGA GGG AAA CAT       480
Ile Ile Ile Thr Gly Asn Gly Gly Ile Gln Trp Ser Arg Gly Lys His
145                 150                 155                 160

AAG GAA AGT GAG ACA CTG ACA GAA CAG GAC GTA CAG TTA TAT TGT GAT       528
Lys Glu Ser Glu Thr Leu Thr Glu Gln Asp Val Gln Leu Tyr Cys Asp
                165                 170                 175

TTC CCT GAT ATT ATT GAT GTC AGT ATT AAG CAA GCA AAT CAG GAA TGC       576
Phe Pro Asp Ile Ile Asp Val Ser Ile Lys Gln Ala Asn Gln Glu Cys
            180                 185                 190

TCA ACT GAA AGT AGA GTT GTG ACC GTC CAC AAG CAG GAC GGG AAG GTC       624
Ser Thr Glu Ser Arg Val Val Thr Val His Lys Gln Asp Gly Lys Val
        195                 200                 205

TTG GAA ATA GAA CTT AGC TCA TTA AAA GAA GCC TTG TCA TTC GTG TCA       672
Leu Glu Ile Glu Leu Ser Ser Leu Lys Glu Ala Leu Ser Phe Val Ser
    210                 215                 220

TTA ATT GAC GGG TAT TAC AGA CTA ACT GCG GAT GCA CAC CAT TAC CTC       720
Leu Ile Asp Gly Tyr Tyr Arg Leu Thr Ala Asp Ala His His Tyr Leu
225                 230                 235                 240

TGC AAA GAG GTG GCT CCC CCA GCT GTG TTC GAG AAC ATA CAC AGC AAC       768
Cys Lys Glu Val Ala Pro Pro Ala Val Phe Glu Asn Ile His Ser Asn
                245                 250                 255

TGC CAC GGC CCA ATT TCA ATG GAT TTT GCC ATC AGC AAA CTA AAG AAG       816
Cys His Gly Pro Ile Ser Met Asp Phe Ala Ile Ser Lys Leu Lys Lys
            260                 265                 270

GCA GGA AAC CAG ACT GGA CTG TAT GTA CTT CGA TGT AGC CCT AAG GAC       864
Ala Gly Asn Gln Thr Gly Leu Tyr Val Leu Arg Cys Ser Pro Lys Asp
        275                 280                 285

TTC AAC AAA TAC TTC CTG ACC TTT GCC GTT GAG CGA GAA AAT GTT ATT       912
Phe Asn Lys Tyr Phe Leu Thr Phe Ala Val Glu Arg Glu Asn Val Ile
    290                 295                 300

GAA TAT AAA CAC TGT TTG ATT ACA AAG AAT GAG AAT GGA GAG TAC AAC       960
Glu Tyr Lys His Cys Leu Ile Thr Lys Asn Glu Asn Gly Glu Tyr Asn
305                 310                 315                 320

CTC AGT GGG ACT AAG AGG AAC TTC AGT AGT CTT AAG GAC CTT TTG AAT      1008
Leu Ser Gly Thr Lys Arg Asn Phe Ser Ser Leu Lys Asp Leu Leu Asn
```

```
                        325                 330                 335
TGC TAC CAG ATG GAA ACT GTG CGC TCA GAC AGT ATC ATC TTC CAG TTC    1056
Cys Tyr Gln Met Glu Thr Val Arg Ser Asp Ser Ile Ile Phe Gln Phe
            340                 345                 350

ACC AAA TGC TGT CCT CCA AAG CCG AAA GAT AAA TCA AAC CTT CTT GTC    1104
Thr Lys Cys Cys Pro Pro Lys Pro Lys Asp Lys Ser Asn Leu Leu Val
            355                 360                 365

TTC AGA ACA AAT GGT GTT TCT GAT GTT CAG CTC TCA CCA ACA TTA CAG    1152
Phe Arg Thr Asn Gly Val Ser Asp Val Gln Leu Ser Pro Thr Leu Gln
    370                 375                 380

AGG CAT AAT AAT GTG AAT CAA ATG GTG TTT CAC AAA ATC AGG AAT GAA    1200
Arg His Asn Asn Val Asn Gln Met Val Phe His Lys Ile Arg Asn Glu
385                 390                 395                 400

GAT TTG ATA TTT AAT GAA AGC CTT GGC CAA GGC ACT TTT ACA AAA ATA    1248
Asp Leu Ile Phe Asn Glu Ser Leu Gly Gln Gly Thr Phe Thr Lys Ile
                405                 410                 415

TTT AAA GGT GTA AGA AGA GAA GTT GGA GAT TAT GGT CAG CTG CAC GAA    1296
Phe Lys Gly Val Arg Arg Glu Val Gly Asp Tyr Gly Gln Leu His Glu
            420                 425                 430

ACC GAA GTT CTT TTG AAA GTC CTA GAT AAA GCA CAT AGA AAC TAT TCA    1344
Thr Glu Val Leu Leu Lys Val Leu Asp Lys Ala His Arg Asn Tyr Ser
            435                 440                 445

GAG TCT TTC TTT GAA GCA GCA AGC ATG ATG AGT CAG CTT TCT CAC AAG    1392
Glu Ser Phe Phe Glu Ala Ala Ser Met Met Ser Gln Leu Ser His Lys
    450                 455                 460

CAT TTG GTT TTG AAT TAT GGA GTA TGT GTC TGT GGA GAG GAG AAC ATT    1440
His Leu Val Leu Asn Tyr Gly Val Cys Val Cys Gly Glu Glu Asn Ile
465                 470                 475                 480

TTG GTT CAA GAG TTT GTA AAA TTT GGA TCA CTG GAT ACA TAC CTG AAG    1488
Leu Val Gln Glu Phe Val Lys Phe Gly Ser Leu Asp Thr Tyr Leu Lys
                485                 490                 495

AAG AAC AAA AAT TCT ATA AAT ATA TTA TGG AAA CTT GGA GTG GCG AAG    1536
Lys Asn Lys Asn Ser Ile Asn Ile Leu Trp Lys Leu Gly Val Ala Lys
            500                 505                 510

CAG TTG GCA TGG GCC ATG CAC TTC CTC GAA GAA AAA TCC CTT ATT CAT    1584
Gln Leu Ala Trp Ala Met His Phe Leu Glu Glu Lys Ser Leu Ile His
            515                 520                 525

GGG AAT GTG TGT GCT AAA AAT ATC CTG CTT ATC AGA GAA GAA GAC AGG    1632
Gly Asn Val Cys Ala Lys Asn Ile Leu Leu Ile Arg Glu Glu Asp Arg
    530                 535                 540

AGA ACG GGG AAC CCA CCT TTC ATC AAA CTT AGT GAT CCT GGC ATT AGC    1680
Arg Thr Gly Asn Pro Pro Phe Ile Lys Leu Ser Asp Pro Gly Ile Ser
545                 550                 555                 560

ATT ACA GTT CTA CCG AAG GAC ATT TCT TCC TGT TGT TTC CAA GTT CTT    1728
Ile Thr Val Leu Pro Lys Asp Ile Ser Ser Cys Cys Phe Gln Val Leu
                565                 570                 575

CAG GAG AGA ATA CCA TGG GTA CCA CCT GAG TGC ATT GAG AAT CCT AAA    1776
Gln Glu Arg Ile Pro Trp Val Pro Pro Glu Cys Ile Glu Asn Pro Lys
            580                 585                 590

AAT CTA ACT CTG GCA ACA GAC AAG TGG AGC TTC GGG ACC ACT CTG TGG    1824
Asn Leu Thr Leu Ala Thr Asp Lys Trp Ser Phe Gly Thr Thr Leu Trp
            595                 600                 605

GAG ATC TGC AGT GGA GGA GAT AAG CCC CTG AGT GCT CTG GAT TCT CAA    1872
Glu Ile Cys Ser Gly Gly Asp Lys Pro Leu Ser Ala Leu Asp Ser Gln
    610                 615                 620

AGA AAG CTG CAG TTC TAT GAA GAT AAG CAT CAG CTT CCT GCA CCC AAG    1920
Arg Lys Leu Gln Phe Tyr Glu Asp Lys His Gln Leu Pro Ala Pro Lys
625                 630                 635                 640

TGG ACA GAG TTG GCA AAC CTT ATA AAT AAT GCA TGG ACT ATG AGC CCA    1968
```

```
Trp Thr Glu Leu Ala Asn Leu Ile Asn Asn Cys Met Asp Tyr Glu Pro
            645                 650                 655

GAT TTC AGG CCT GCT TTC AGA GCT GTC ATC CGT GAT CTT AAC AGC CTG      2016
Asp Phe Arg Pro Ala Phe Arg Ala Val Ile Arg Asp Leu Asn Ser Leu
            660                 665                 670

TTT ACT CCA GAT TAT GAA CTA CTA ACA GAA AAT GAC ATG CTA CCA AAC      2064
Phe Thr Pro Asp Tyr Glu Leu Leu Thr Glu Asn Asp Met Leu Pro Asn
            675                 680                 685

ATG AGA ATA GGT GCC CTA GGG TTT TCT GGT GCT TTT GAA GAC AGG GAC      2112
Met Arg Ile Gly Ala Leu Gly Phe Ser Gly Ala Phe Glu Asp Arg Asp
            690                 695                 700

CCT ACA CAG TTT GAA GAG AGA CAC TTG AAG TTT CTA CAG CAG CTT GGC      2160
Pro Thr Gln Phe Glu Glu Arg His Leu Lys Phe Leu Gln Gln Leu Gly
705                 710                 715                 720

AAA GGT AAC TTC GGG AGT GTG GAG ATG TGC CGC TAT GAC CCG CTG CAG      2208
Lys Gly Asn Phe Gly Ser Val Glu Met Cys Arg Tyr Asp Pro Leu Gln
                725                 730                 735

GAC AAC ACT GGC GAG GTG GTC GCT GTG AAG AAA CTC CAG CAC AGC ACT      2256
Asp Asn Thr Gly Glu Val Val Ala Val Lys Lys Leu Gln His Ser Thr
            740                 745                 750

GAA GAG CAC CTC CGA GAC TTT GAG AGG GAG ATC GAG ATC CTG AAA TCC      2304
Glu Glu His Leu Arg Asp Phe Glu Arg Glu Ile Glu Ile Leu Lys Ser
            755                 760                 765

TTG CAG CAT GAC AAC ATC GTC AAG TAC AAG GGA GTG TGC TAC AGT GCG      2352
Leu Gln His Asp Asn Ile Val Lys Tyr Lys Gly Val Cys Tyr Ser Ala
            770                 775                 780

GGT CGG CGC AAC CTA AGA TTA ATT ATG GAA TAT TTA CCA TAT GGA AGT      2400
Gly Arg Arg Asn Leu Arg Leu Ile Met Glu Tyr Leu Pro Tyr Gly Ser
785                 790                 795                 800

TTA CGA GAC TAT CTC CAA AAA CAT AAA GAA CGG ATA GAT CAC AAA AAA      2448
Leu Arg Asp Tyr Leu Gln Lys His Lys Glu Arg Ile Asp His Lys Lys
                805                 810                 815

CTT CTT CAA TAC ACA TCT CAG ATA TGC AAG GGC ATG GAA TAT CTT GGT      2496
Leu Leu Gln Tyr Thr Ser Gln Ile Cys Lys Gly Met Glu Tyr Leu Gly
            820                 825                 830

ACA AAA AGG TAT ATC CAC AGG GAC CTG GCA ACA AGG AAC ATA TTG GTG      2544
Thr Lys Arg Tyr Ile His Arg Asp Leu Ala Thr Arg Asn Ile Leu Val
            835                 840                 845

GAA AAT GAG AAC AGG GTT AAA ATA GGA GAC TTC GGA TTA ACC AAA GTC      2592
Glu Asn Glu Asn Arg Val Lys Ile Gly Asp Phe Gly Leu Thr Lys Val
850                 855                 860

TTG CCG CAG GAC AAA GAA TAC TAC AAA GTA AAG GAG CCA GGG GAA AGC      2640
Leu Pro Gln Asp Lys Glu Tyr Tyr Lys Val Lys Glu Pro Gly Glu Ser
865                 870                 875                 880

CCC ATA TTC TGG TAC GCA CCT GAA TCC TTG ACG GAG AGC AAG TTT TCT      2688
Pro Ile Phe Trp Tyr Ala Pro Glu Ser Leu Thr Glu Ser Lys Phe Ser
                885                 890                 895

GTG GCC TCA GAT GTG TGG AGC TTT GGA GTG GTT CTA TAC GAA CTT TTC      2736
Val Ala Ser Asp Val Trp Ser Phe Gly Val Val Leu Tyr Glu Leu Phe
            900                 905                 910

ACA TAC ATC GAG AAG AGT AAA AGT CCA CCC GTG GAA TTT ATG CGA ATG      2784
Thr Tyr Ile Glu Lys Ser Lys Ser Pro Pro Val Glu Phe Met Arg Met
            915                 920                 925

ATT GGC AAT GAT AAA CAA GGG CAA ATG ATT GTG TTC CAT TTG ATA GAG      2832
Ile Gly Asn Asp Lys Gln Gly Gln Met Ile Val Phe His Leu Ile Glu
            930                 935                 940

CTA CTG AAG AGC AAC GGA AGA TTG CCA AGG CCA GAA GGA TGC CCA GAT      2880
Leu Leu Lys Ser Asn Gly Arg Leu Pro Arg Pro Glu Gly Cys Pro Asp
945                 950                 955                 960
```

-continued

```
GAG ATT TAT GTG ATC ATG ACA GAG TGC TGG AAC AAC AAT GTG AGC CAG     2928
Glu Ile Tyr Val Ile Met Thr Glu Cys Trp Asn Asn Asn Val Ser Gln
                965                 970                 975

CGT CCC TCC TTC AGG GAC CTT TCC TTC GGG TGG ATC AAA TCC GGG ACA     2976
Arg Pro Ser Phe Arg Asp Leu Ser Phe Gly Trp Ile Lys Ser Gly Thr
            980                 985                 990

GTA TAGCTGCGTG AAAGAGATGG CCTTACTCAG AGACCAAGCA GACTTCCAGA          3029
Val

ACCAGAACAA AGCTCTGTAG CCTTGTGTCT ACACATCCTT ATCATGACGC TAGCTAGGCA   3089

GAAAGAAAAC TGTGACGCCG TCTGCTCAAA AGCTTTGGAA AACGCCGTGC AGGTTTGTTT   3149

CATCACCATC TGTAAAAACC ACTGCTCAAG TCTGGCAGCA TGCTTGTGGG CTGATGCATG   3209

GAGCTCACCA CAGAGTCTCT GCATCTCCTC TGACAGAAGA AGAAAAATAG ACAATTTTCA   3269

ACTCACTTTT TTGAGAAATG GAAAAAAATT ATAATGTAAA TTTTTCAGTG TAGGAAATAC   3329

ACAGAACATA CATGTACAGT TTTTACCACG TGGAGTGTAT AATACTTTGG CCTCTTGTGT   3389

GATTTACATG AGGGCTGATG TTTGTTAATG TTTTCTAATT TTTCCATAGG TGATCTATAA   3449

TAACTTCATG ATACAAATTA AAATGCTCAG AAAATTAAAA AAAAA                  3495
```

(2) INFORMATION FOR SEQ ID NO: 4:

(i) SEQUENCE CHARACTERISTICS:
        (A) LENGTH: 993 amino acids
        (B) TYPE: amino acid
        (D) TOPOLOGY: linear (ii) MOLECULE TYPE: protein (xi) SEQUENCE DESCRIPTION: SEQ ID NO: 4:

```
Leu Leu Asp Asp Phe Val Met Ser Tyr Leu Ser Pro Gln Trp Arg His
  1               5                  10                  15

Asp Phe Val His Gly Trp Ile Lys Val Pro Val Thr His Glu Thr Gln
             20                  25                  30

Glu Glu Cys Leu Gly Met Ala Val Leu Asp Met Met Arg Ile Ala Lys
         35                  40                  45

Glu Lys Asp Gln Thr Pro Leu Ala Val Tyr Asn Ser Val Ser Tyr Lys
     50                  55                  60

Thr Phe Leu Pro Lys Cys Val Arg Ala Lys Ile Gln Asp Tyr His Ile
 65                  70                  75                  80

Leu Thr Arg Lys Arg Ile Arg Tyr Arg Phe Arg Arg Phe Ile Gln Gln
                 85                  90                  95

Phe Ser Gln Cys Lys Ala Thr Ala Arg Asn Leu Lys Leu Lys Tyr Leu
            100                 105                 110

Ile Asn Leu Glu Thr Leu Gln Ser Ala Phe Tyr Thr Glu Gln Phe Glu
        115                 120                 125

Val Lys Glu Ser Ala Arg Gly Pro Ser Gly Glu Glu Ile Phe Ala Thr
    130                 135                 140

Ile Ile Thr Gly Asn Gly Ile Gln Trp Ser Arg Gly Lys His
145                 150                 155                 160

Lys Glu Ser Glu Thr Leu Thr Glu Gln Asp Val Gln Leu Tyr Cys Asp
                165                 170                 175

Phe Pro Asp Ile Ile Asp Val Ser Ile Lys Gln Ala Asn Gln Glu Cys
            180                 185                 190

Ser Thr Glu Ser Arg Val Val Thr Val His Lys Gln Asp Gly Lys Val
        195                 200                 205

Leu Glu Ile Glu Leu Ser Ser Leu Lys Glu Ala Leu Ser Phe Val Ser
```

-continued

```
              210                 215                 220
Leu Ile Asp Gly Tyr Tyr Arg Leu Thr Ala Asp Ala His His Tyr Leu
225                 230                 235                 240

Cys Lys Glu Val Ala Pro Ala Val Phe Glu Asn Ile His Ser Asn
                245                 250                 255

Cys His Gly Pro Ile Ser Met Asp Phe Ala Ile Ser Lys Leu Lys Lys
                260                 265                 270

Ala Gly Asn Gln Thr Gly Leu Tyr Val Leu Arg Cys Ser Pro Lys Asp
                275                 280                 285

Phe Asn Lys Tyr Phe Leu Thr Phe Ala Val Glu Arg Glu Asn Val Ile
290                 295                 300

Glu Tyr Lys His Cys Leu Ile Thr Lys Asn Glu Asn Gly Glu Tyr Asn
305                 310                 315                 320

Leu Ser Gly Thr Lys Arg Asn Phe Ser Ser Leu Lys Asp Leu Leu Asn
                325                 330                 335

Cys Tyr Gln Met Glu Thr Val Arg Ser Asp Ser Ile Ile Phe Gln Phe
                340                 345                 350

Thr Lys Cys Cys Pro Pro Lys Pro Lys Asp Lys Ser Asn Leu Leu Val
                355                 360                 365

Phe Arg Thr Asn Gly Val Ser Asp Val Gln Leu Ser Pro Thr Leu Gln
370                 375                 380

Arg His Asn Asn Val Asn Gln Met Val Phe His Lys Ile Arg Asn Glu
385                 390                 395                 400

Asp Leu Ile Phe Asn Glu Ser Leu Gly Gln Gly Thr Phe Thr Lys Ile
                405                 410                 415

Phe Lys Gly Val Arg Arg Glu Val Gly Asp Tyr Gly Gln Leu His Glu
                420                 425                 430

Thr Glu Val Leu Leu Lys Val Leu Asp Lys Ala His Arg Asn Tyr Ser
                435                 440                 445

Glu Ser Phe Phe Glu Ala Ala Ser Met Met Ser Gln Leu Ser His Lys
                450                 455                 460

His Leu Val Leu Asn Tyr Gly Val Cys Val Cys Gly Glu Glu Asn Ile
465                 470                 475                 480

Leu Val Gln Glu Phe Val Lys Phe Gly Ser Leu Asp Thr Tyr Leu Lys
                485                 490                 495

Lys Asn Lys Asn Ser Ile Asn Ile Leu Trp Lys Leu Gly Val Ala Lys
                500                 505                 510

Gln Leu Ala Trp Ala Met His Phe Leu Glu Glu Lys Ser Leu Ile His
                515                 520                 525

Gly Asn Val Cys Ala Lys Asn Ile Leu Leu Ile Arg Glu Glu Asp Arg
530                 535                 540

Arg Thr Gly Asn Pro Pro Phe Ile Lys Leu Ser Asp Pro Gly Ile Ser
545                 550                 555                 560

Ile Thr Val Leu Pro Lys Asp Ile Ser Ser Cys Cys Phe Gln Val Leu
                565                 570                 575

Gln Glu Arg Ile Pro Trp Val Pro Glu Cys Ile Glu Asn Pro Lys
                580                 585                 590

Asn Leu Thr Leu Ala Thr Asp Lys Trp Ser Phe Gly Thr Thr Leu Trp
                595                 600                 605

Glu Ile Cys Ser Gly Gly Asp Lys Pro Leu Ser Ala Leu Asp Ser Gln
                610                 615                 620

Arg Lys Leu Gln Phe Tyr Glu Asp Lys His Gln Leu Pro Ala Pro Lys
625                 630                 635                 640
```

-continued

```
Trp Thr Glu Leu Ala Asn Leu Ile Asn Asn Cys Met Asp Tyr Glu Pro
                645                 650                 655
Asp Phe Arg Pro Ala Phe Arg Ala Val Ile Arg Asp Leu Asn Ser Leu
            660                 665                 670
Phe Thr Pro Asp Tyr Glu Leu Leu Thr Glu Asn Asp Met Leu Pro Asn
        675                 680                 685
Met Arg Ile Gly Ala Leu Gly Phe Ser Gly Ala Phe Glu Asp Arg Asp
    690                 695                 700
Pro Thr Gln Phe Glu Arg His Leu Lys Phe Leu Gln Gln Leu Gly
705                 710                 715                 720
Lys Gly Asn Phe Gly Ser Val Glu Met Cys Arg Tyr Asp Pro Leu Gln
                725                 730                 735
Asp Asn Thr Gly Glu Val Val Ala Val Lys Lys Leu Gln His Ser Thr
            740                 745                 750
Glu Glu His Leu Arg Asp Phe Glu Arg Glu Ile Glu Ile Leu Lys Ser
        755                 760                 765
Leu Gln His Asp Asn Ile Val Lys Tyr Lys Gly Val Cys Tyr Ser Ala
    770                 775                 780
Gly Arg Arg Asn Leu Arg Leu Ile Met Glu Tyr Leu Pro Tyr Gly Ser
785                 790                 795                 800
Leu Arg Asp Tyr Leu Gln Lys His Lys Glu Arg Ile Asp His Lys Lys
                805                 810                 815
Leu Leu Gln Tyr Thr Ser Gln Ile Cys Lys Gly Met Glu Tyr Leu Gly
            820                 825                 830
Thr Lys Arg Tyr Ile His Arg Asp Leu Ala Thr Arg Asn Ile Leu Val
        835                 840                 845
Glu Asn Glu Asn Arg Val Lys Ile Gly Asp Phe Gly Leu Thr Lys Val
    850                 855                 860
Leu Pro Gln Asp Lys Glu Tyr Tyr Lys Val Lys Glu Pro Gly Glu Ser
865                 870                 875                 880
Pro Ile Phe Trp Tyr Ala Pro Glu Ser Leu Thr Glu Ser Lys Phe Ser
                885                 890                 895
Val Ala Ser Asp Val Trp Ser Phe Gly Val Val Leu Tyr Glu Leu Phe
            900                 905                 910
Thr Tyr Ile Glu Lys Ser Lys Ser Pro Pro Val Glu Phe Met Arg Met
        915                 920                 925
Ile Gly Asn Asp Lys Gln Gly Gln Met Ile Val Phe His Leu Ile Glu
    930                 935                 940
Leu Leu Lys Ser Asn Gly Arg Leu Pro Arg Pro Glu Gly Cys Pro Asp
945                 950                 955                 960
Glu Ile Tyr Val Ile Met Thr Glu Cys Trp Asn Asn Asn Val Ser Gln
                965                 970                 975
Arg Pro Ser Phe Arg Asp Leu Ser Phe Gly Trp Ile Lys Ser Gly Thr
            980                 985                 990
Val
```

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid

```
            (A) DESCRIPTION: /desc = "DNA"

(xi) SEQUENCE DESCRIPTION: SEQ ID NO: 5:

GTGGATCCAT GAATGGTGCC CCTTCCCCAG AGGATG                                    36

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO: 6:

CGGAATTCTC AGACAAATGA GTACTGGTTA TTA                                       33
```

COMPOSITIONS AND METHODS FOR IDENTIFYING SIGNALING PATHWAY AGONISTS AND ANTAGONISTS

This invention was made with government support under grant NIH R01-DK34171. The government has certain rights in the invention.

FIELD OF THE INVENTION

The invention generally relates to compositions and methods for identifying cytokine, hormone and growth factor signaling pathway agonists and antagonists.

BACKGROUND OF INVENTION

Growth hormone (GH) is well recognized as an important regulator of body growth and metabolism. It is currently used to treat children of short stature, growth hormone deficient adults, surgical patients (to prevent muscle wasting), and burn patients (increase growth rate of skin), to name a few of its therapeutic uses. Other cytokines, hormones and growth factors that act by a similar mechanism regulate a whole host of important body functions, including milk production, the immune system, nerve growth and regeneration, appetite and body fat composition.

As the therapeutic potential of GH (and GH suppression) becomes apparent, a more mechanistic understanding of GH action at the cellular and molecular levels is needed. The initial steps in the pathway following the binding of GH to its receptor have recently been established. It is now known that growth hormone receptor (GHR) forms a complex with a tyrosine kinase. See Argetsinger et al., "Identification of JAK2 as a Growth Hormone Receptor-Associated Tyrosine Kinase," *Cell* 74:237 (1993). The kinase, termed JAK2, is a member of the Janus family of tyrosine kinases. In addition to having a kinase domain, these proteins are characterized by the presence of a second kinase-like domain and the absence of Src homology 2 (SH2), SH3, and membrane-spanning domains. Ligand binding to the cytokine receptor appears to activate the kinase, causing tyrosyl phosphorylation of both JAK2 and the receptor involved, such as GHR for GH mediated signaling. The steps beyond this point are largely unclear, although it has been presumed that other intracellular proteins are recruited to JAK2-receptor complexes.

It is important that the other members of the pathway be identified, given that direct use of some growth factors, such as GH is associated with undesirable side-effects. A better understanding of the signaling pathway and elucidation of the cellular mechanisms by which these agents act is required, in order to define the origin of diseases caused by their malfunction as well as design specific therapeutics.

SUMMARY OF THE INVENTION

The invention generally relates to compositions and methods for identifying cytokine, hormone and growth factor signaling pathway agonists and antagonists, and more particularly, methods and compositions for screening compounds and identifying compounds that will modulate the interactions of cytokine receptors with their intracellular ligands, as well as between their intracellular ligands and other members of the signaling pathway. It is not intended that the present invention be limited to particular cytokines or particular signaling pathways. The present invention contemplates that the methods and compositions described herein will be useful with a variety of cytokines, hormones and growth factors, including but not limited to GH, interferon-gamma (IFN-γ), platelet-derived growth factor (PDGF) epidermal growth factor (EGF), and nerve growth factor (NGF) to identify compounds that will modulate the interactions of receptors that bind these extracellular ligands, as well as between their intracellular ligands and other members of the signaling pathway.

In one embodiment, the present invention contemplates screening compounds and identifying compounds that modulate the interactions of receptors with tyrosine kinases, and in particular JAK2. Furthermore, the present invention contemplates identifying JAK2 substrates and JAK2-binding ligands, and compounds that will modulate the interaction of JAK2 kinase with JAK2 substrates and JAK2 binding ligands.

In one embodiment, the present invention contemplates identifying compounds that modulate the interaction of SH2-Bβ, which binds to activated, Tyr phosphorylated JAK2. In other embodiments, the present invention contemplates identifying compounds that modulate the interaction of SH2-Bβ, which binds to unphosphorylated JAK2.

In preferred embodiments, SH2-Bβ (and in particular, fragments of SH2-Bβ) are useful in drug screening assays designed to identify drugs that interfere with the specific binding of JAK2 kinases with their substrate as well as JAK2 kinase activity, and thereby block the activation of downstream signaling molecules. In other embodiments, the present invention contemplates identifying compounds that modulate the interaction of SH2-Bβ, which may bind to kinases other than JAK2.

Moreover, the present invention contemplates identifying ERK½ substrates and ERK½-binding ligands, and compounds that will modulate the interaction of MAP kinase with ERK½ substrates and ERK½ binding ligands.

In other embodiments, the invention provides an isolated SH2-Bβ polypeptide, or a fragment thereof, having JAK2 kinase-specific binding affinity. The invention provides nucleic acids encoding the SH2-Bβ polypeptide and SH2-Bβ fragments as part of expression vectors for introduction into cells. The invention provides methods of identifying intracellular molecules which interact with SH2-Bβ or SH2-Bβ fragments, as well as exogenous agents (i.e. drugs) which disrupt the binding of SH2-Bβ and/or fragments thereof to such intracellular targets.

The claimed polypeptide SH2-Bβ and SH2-Bβ fragments find particular use in screening assays for agents or lead compounds for agents useful in the diagnosis, prognosis or treatment of disease, particularly disease associated with undesirable cell growth, cell movement, apoptosis, differentiation and/or cytokine/growth factor signal responsiveness. One such assay involves forming mixtures of 1) SH2-Bβ (or fragments thereof) and 2) an intracellular SH2-Bβ-binding ligand, in the presence or absence of 3) a prospective drug candidate. The mixtures are made under conditions that permit the binding of the intracellular SH2-Bβ-binding ligand to SH2-Bβ (or fragments thereof) and the mixtures are then analyzed for the presence of such binding. A difference in such binding in the presence of such a drug candidate indicates that the agent is capable of modulating the binding of SH2-Bβ (or fragments thereof) to an intracellular SH2-Bβ-binding ligand.

It is not intended that the present invention be limited by the species (human, murine, rat, etc.) of the binding ligands described above. The polypeptide SH2-Bβ and SH2-Bβ fragments are shown below to bind across species. Moreover, the nucleic acid sequences described herein allow for the identification of homologues in other species by various methods, including but not limited to amplification (e.g. PCR) using primers designed from the nucleic acid sequence of one species (e.g. rat) on the nucleic acid template of another species (e.g. human).

In one embodiment, the present invention contemplates an isolated nucleic acid encoding at least a fragment of a protein having the amino acid sequence set forth in SEQ ID NO:2. It is not intended that the present invention be limited by the size or nature of the fragment (although it is preferred that such fragments are capable of binding kinases). In one embodiment, said nucleic acid encodes full-length SH2-Bβ as set forth in (SEQ ID NO:2) and said nucleic acid comprises SEQ ID NO:1. In another embodiment, said nucleic acid encodes a fragment comprising either residues 527–670, residues 1–555, or residues 1–631 of the amino acid sequence set forth in SEQ ID NO:2. In yet another embodiment, said nucleic acid encodes a fusion protein.

It is not intended that the present invention be limited as to the specific nature of the nucleic acid encoding the peptides described above. In one embodiment, said nucleic acid is contained in a vector. In another embodiment, said vector is in a host cell.

The present invention also contemplates complexes of ligands. In one embodiment, the present invention contemplates a composition, comprising a SH2-Bβ—kinase complex comprising a purified peptide having at least a portion of the amino acid sequence set forth in SEQ ID NO:2 specifically bound to JAK2 (or other kinase). Again, the peptides bound specifically to JAK2 may be full-length SH2-Bβ or a fragment defined by a portion of the amino acid sequence as set forth in SEQ ID NO:2. The peptide may be part of a fusion protein. The complex can also contain other ligands, such as hormone receptors and cytokine receptors. The complexes can be used to identify other ligands (as described below).

As noted above, the present invention contemplates compound screening assays. In one embodiment, the present invention contemplates a method for compound screening, comprising: a) providing: i) a peptide comprising at least a portion of the amino acid sequence set forth in SEQ ID NO:2, wherein said portion is capable of binding to JAK2 kinase, ii) JAK2 kinase, and iii) one or more compounds for screening; b) mixing, in any order, said peptide, said JAK2 kinase and said one or more compound; and c) measuring the extent of binding of said peptide to said JAK2 kinase. Again, the peptides may be full-length SH2-Bβ or a fragment defined by a portion of the amino acid sequence as set forth in SEQ ID NO:2. The peptide may also be part of a fusion protein. The present invention also contemplates embodiments where either the peptide or kinase is bound to other ligands, such as hormone receptors and cytokine receptors. These complexes can be used in the compound screening assay described above.

DESCRIPTION OF THE FIGURES

FIG. 1(C) is a table which indicates the results of the interaction of SH2-Bβc with JAK2 in the yeast two-hybrid system. The indicated LexA DNA binding domain hybrids and the B42 activation domain hybrids were introduced into yeast with the LacZ reporter gene. The interaction of a LexA hybrid with an activation domain hybrid was assessed by examining the activation of reporter LacZ and Leu using filter lift color assay or by growing the transformants in selective media lacking Leu, respectively.

FIG. 2A shows the nucleotide sequence (SEQ ID NO: 1) of SH2-Bβ.

FIG. 2B shows the amino acid sequence (SEQ ID NO:2) of SH2-Bβ.

FIG. 3A shows both the nucleotide sequence (SEQ ID NO:3) and amino acid sequence (SEQ ID NO:4) of the murine JAK2 tyrosine kinase.

DEFINITIONS

Figure 1A:
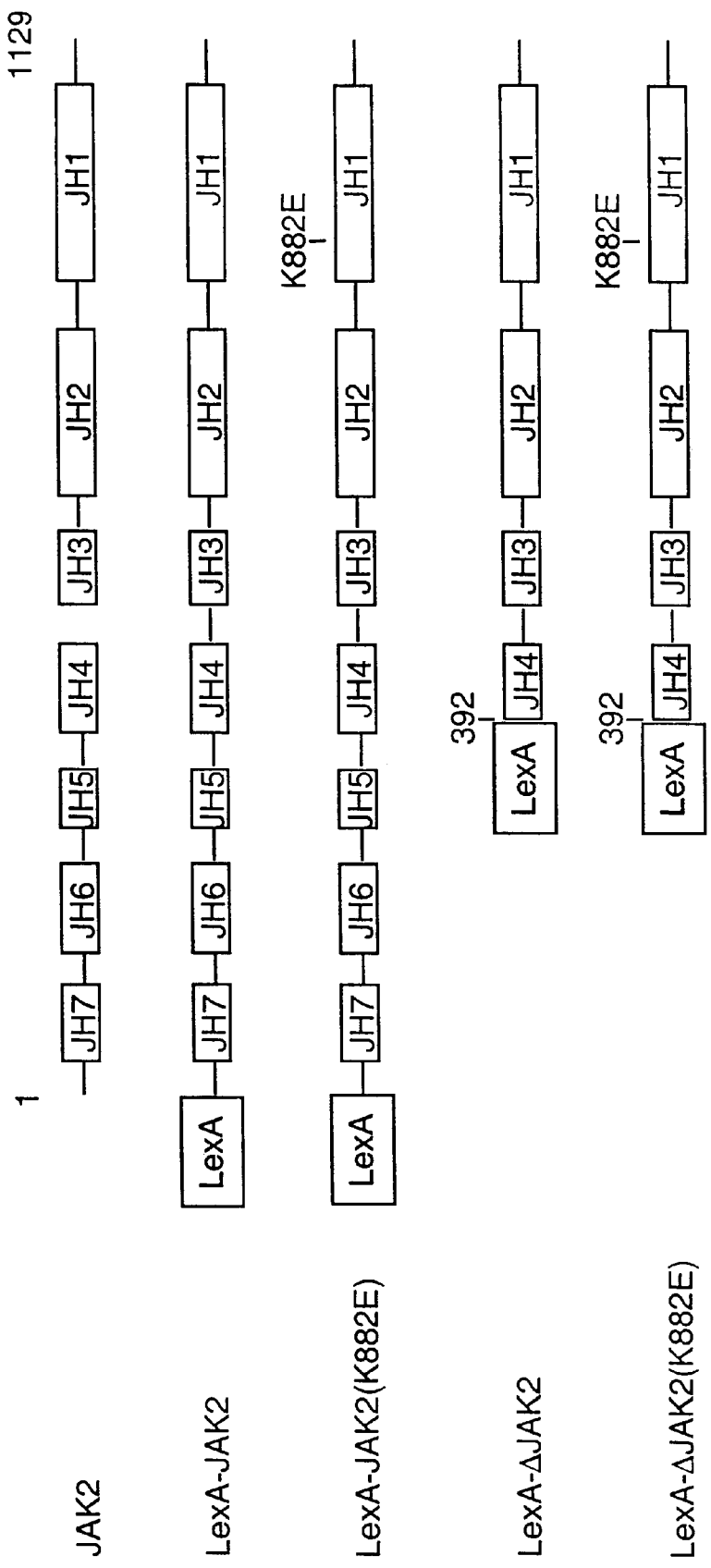
FIG. 1(A) is a representation of hybrids of JAK2 and JAK2 mutants fused to the LexA DNA binding domain used in the yeast two-hybrid system. The positions of the deletions and point mutations are shown by numbers. The boxes represent subdomains of JAK2.

To facilitate understanding of the invention, a number of terms are defined below.

The abbreviations used herein are: JAK, Janus family of cytoplasmic protein tyrosine kinases, PDGF, platelet-derived growth factor; GH, growth hormone; EGF, epidermal growth factor; IFNγ, Interferon-gamma; PP2A, protein phosphatase 2A; GST, glutathione S-transferase; GHR, growth hormone receptor; PDGFR, platelet-derived growth factor receptor; PAGE, polyacrylamide gel electrophoresis; SDS, sodium dodecylsulfate; Ins, Insulin; IRS, Insulin receptor substrate; NGF, nerve growth factor; αSH2-B, anti-SH2-B; GFP, Green Fluorescent Protein.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et al., *Biochimie* 67:755 (1985). In the case of radioactive oligonucleotide probes, only extremely high specific activities are found to show satisfactory results. See Studencki and Wallace, *DNA* 3:1 (1984) and Studencki et al., *Human Genetics* 37:42 (1985).

K. B. Mullis et al., U.S. Pat. Nos. 4,683,195 and 4,683,202, hereby incorporated by reference, describe a method for increasing the concentration of a segment of a target sequence in a mixture of genomic DNA without cloning or purification. This process for amplifying the target sequence (which can be used in conjunction with the present invention to make target molecules) consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. There can be numerous "cycles" to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified".

Figure 2C:
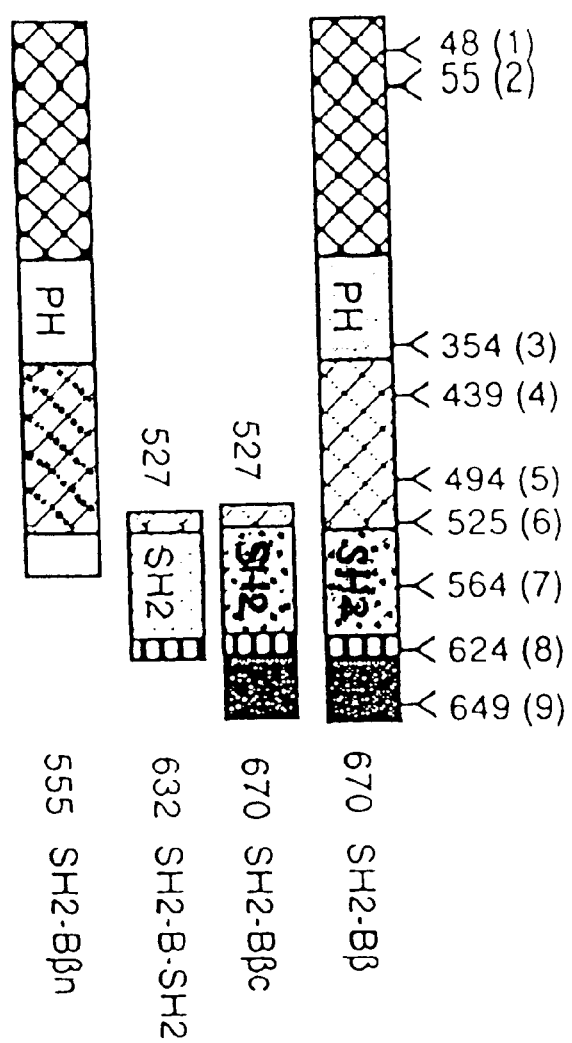
FIG. 2C is a representation of full-length and truncated SH2-Bβ.

The present invention specifically contemplates using primers having a portion of the nucleic acid sequence set forth in FIG. 2A (SEQ ID NO:1) in a PCR reaction to identify homologues of SH2-Bβ, as well as the SH2-Bβ gene in other species. Such primers are preferably less than fifty nucleotides in length (although longer primers can be used if desired).

The present invention also contemplates using probes having a portion of the nucleic acid sequence set forth in FIG. 2A (SEQ ID NO:1). The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g. Green Fluorescent Protein (GFP).

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It should be noted that, while the invention does not require that a comparison be made between one or more forms of a gene to detect sequence variations, such comparisons are possible using particular hybridization conditions as described in U.S. Pat. No. 5,652,096, hereby incorporated by reference.

The term "$K_m$" as used herein refers to the Michaelis-Menton constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. As used herein the term "nucleotide analog" when used in reference to substrates present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRS, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length SH-2B cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length SH2-Bβ sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence (e.g., various fragments of SH-2B protein). Fragments typically are at least 4 amino acids long, preferably at least 20 amino acids long, usually at least 50 amino acids long or longer, and span the portion of the polypeptide required for intermolecular binding of SH2-Bβ.

The term "analog" as used herein refers to polypeptides which are comprised of a segment of at least 25 amino acids that has substantial identity to a portion of the deduced amino acid sequence of SH-2B. The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as antagonists or agonists of SH2-Bβ by inclusion in screening assays described herein below.

GENERAL DESCRIPTION OF THE INVENTION

The invention generally relates to compositions and methods for identifying cytokine, hormone and growth factor signaling pathway agonists and antagonists, and more particularly, methods and compositions for screening compounds and identifying compounds that will modulate the interactions of cytokine receptors with their intracellular ligands, as well as between their intracellular ligands and other members of the signaling pathway.

In one embodiment, the invention contemplates compositions and methods for identifying and testing tyrosine kinase JAK2 substrates and JAK2 kinase signaling pathway agonists and antagonists, and in particular, compositions comprising SH2-B which bind to activated, Tyr phosphorylated JAK2.

The description of the invention involves A) Signaling by the JAK family of tyrosine kinases generally, B) Signaling molecules that bind to GHR-JAK2 complexes, C) Identification of SH2-Bβ as a JAK2 binding protein regulated by GH and other cytokines, hormones and growth factors.
A. Signaling by the JAK Family of Tyrosine Kinases One or more of the JAK kinases (JAK1, JAK2, JAK3 and tyk2) are activated upon ligand binding to members of the cytokine receptor superfamily. Multiple cellular proteins are subsequently phosphorylated, including the associated cytokine receptors and the JAKs themselves (reviewed in Ihle JN, *Adv. Immunol.*, 60:1–35, 1995). The phosphorylated tyrosines are potential docking sites for proteins containing specific phosphotyrosine binding domains [e.g. Src homology (SH)2 and phosphotyrosine binding (PTB) domains]. Specific signaling proteins are thereby recruited into the cytokine signaling networks. While substantial evidence exists to suggest that some signaling molecules bind to pTyr within the receptor itself, little is known about the signaling molecules that bind to pTyr within JAKs, despite the presence of multiple tyrosines. Furthermore, there are functions of GH and other cytokines that cannot yet be explained by the currently understood actions of known signaling molecules. Thus, identification of signaling molecules which specifically interact with tyrosyl phosphorylated JAKs are likely to provide insight into signaling by the cytokines that activate those JAKs.

Of the 25 or so ligands known to activate JAKs, more than two thirds activate JAK2. These include growth hormone (GH), prolactin, erythropoietin, granulocyte-colony stimulating factor, interleukin (IL)-3, IL-5, granulocyte macrophage-colony stimulating factor, leptin, thrombopoietin, IL-12, interferon (IFN)-γ, and ligands whose receptor includes gp130 [IL-6, oncostatin M, leukemia inhibitory factor (LIF), IL-11, cardiotropin, ciliary neurotrophic factor]. Some of these ligands show a marked preference for JAK2, whereas others appear to be less discriminating (Ihle JN, *Adv. Immunol.*, 60:1–35, 1995). The fact that many receptors appear to share JAK2 as a signaling molecule makes it likely that some signaling pathways are shared by these various receptors and also some of the actions of these cytokines are shared [Argetsinger et al., *Cell*, 74:237–244 (1993)].

Murine JAK2 has 49 potential tyrosyl phosphorylation sites. Little is known about which tyrosines are phosphorylated in JAK2 in response to ligand binding or even whether the same tyrosines are phosphorylated in response to all ligands. However, tryptic digestion of autophosphorylated JAK2 expressed in Sf9 cells suggests that 15 or more tyrosines are phosphorylated, with at least two of the phosphorylated tyrosines being present in the kinase domain (Feng et al., *Mol. Cell. Biol.* 17:2497–2501, 1997). This suggests that activated JAK2 contains multiple phosphorylated tyrosines, each with the potential to bind signaling molecules.

JAK2 is a crucial signaling molecule for GH: The JAK kinases have a kinase-like domain (JH2), in addition to a kinase domain (JH1), but no Src homology (SH) 2, SH3, and membrane-spanning domains. Members of the JAK family were considered as good candidates for the GHR-kinase, because of their size (Mr~130,000), their presence in GH-responsive tissues, and the ability of Tyk2 to serve as a signaling molecule for the IFN-α/β receptor, which is distantly related to GHR.

GHR is a member of the cytokine/hematopoietin receptor family which also includes the receptors for prolactin (PRL), erythropoietin (EPO), interleukins (ILs) 2–7, 9, 11–13, 15, granulocyte colony-stimulating factor, granulocyte-macrophage colony-stimulating factor, ciliary neurotrophic factor, LIF, oncostatin M, thrombopoietin, cardiotropin, and leptin (reviewed in Argetsinger L. S. and Carter-Su C. *Physiol Rev.* 76, 4: 1089–1107; L. S. Smit et al., *Handbook of Physiology*, (Section 7) 5, Publ. Oxford Univ. Press). Family members contain a single membrane spanning domain, limited homology in the extracellular domain and no homology to known Tyr kinases. The membrane proximal region of the cytoplasmic domains contain at least one 8 amino acid proline-rich motif (box 1), also found in the related class II cytokine receptors (IFN α/β and γ, IL-10). The fact that GH activates JAK2 suggested that other cytokine receptors might also activate JAK kinases. It was shown that PRL receptor also utilizes JAK2, and that IL-3 and erythropoeitin activate JAK2 (Ihle JN, *Adv. Immunol.*, 60:1–35, 1995). All other members of the cytokine receptor family tested have since been shown to activate one or more JAK family members, with more than ⅔ of them activating JAK2. Since JAK2 physically associates with its activating receptors (via the proline-rich region) and is activated within seconds after receptor engagement, it appears that JAK2 activation is an early, perhaps initiating step in signal transduction by GHR and other cytokine receptors. In support of such a role, a number of signaling molecules that appear to be activated by recruitment to JAK2-GHR complexes were identified (See Schematic A). These proteins include: 1) Shc proteins, which lie upstream of Ras and the mitogen-activated protein (MAP) kinases ERKs 1 and 2, which are implicated in the regulation of cellular growth and/or differentiation. 2) the insulin receptor substrates (IRS) 1 and 2, which may mediate some of the metabolic effects of GH; and 3) the signal transducers and activators of transcription (STAT) 1, 3, 5a, and 5b, which have been implicated as regulators of transcription of a variety of genes. Mutant GHR that fail to bind JAK2 (deleted or mutated box1) also fail to elicit GH-dependent Tyr phosphorylation of SHC proteins, ERKs 1 and 2, and of IRS-1 and IRS-2. They also fail to induce spi 2.1 gene promoter constructs in Chinese hamster ovary (CHO) cells, GH-dependent insulin synthesis in rat insulinoma (RIN)-5AH cells, and mitogenesis when expressed in FDC-P1 cells and Ba/F3 cells. In fact, GH-dependent calcium transport is the only GH
action reported to be JAK2-independent. JAK2 is hypothesized to elicit these responses in large part by providing pTyr containing motifs in both GHR and JAK2, which recruit signaling molecules into GHR-JAK2 complexes.

B. Signaling Molecules that Bind to GHR-JAK2 Complexes

All of the known signaling molecules recruited to GHR-JAK2 complexes contain pTyr binding domains (either SH2, PTyr binding (PTB), or both) and are hypothesized to be recruited to pTyr within either GHR or JAK2 or both. These signaling molecules are themselves phosphorylated on Tyr in response to GH, presumably by binding GHR-JAK2 complexes, and their Tyr phosphorylation is required for signaling. Some of these proteins (e.g. Stat5a or b) clearly are recruited to multiple Tyr within GHR. For others (e.g. IRS1, IRS2, Stat1, Stat3, Shc) the mechanism of activation is unclear; some evidence suggests that Tyr within GHR contribute to a maximal response while other evidence suggests that Tyr within GHR are not required for activation and that therefore Tyr within JAK2 must play a role. The likelihood of the latter is strengthened by the fact that while GHR has only 10 Tyr, murine JAK2 has 49 Tyr which, if phosphorylated, could serve as docking sites for SH2- or PTB domain containing signaling molecules. Proteolytic digestion of autophosphorylated JAK2 expressed in Sf9 cells suggests that 15 or more Tyr are phosphorylated Until recently, no protein had been identified that was known to be activated in response to cytokines as a consequence of binding to pTyr within JAK2. Two such proteins have recently been identified: the SOCs family of proteins and SH2-Bβ, a composition of the present invention. Based upon their amino acid sequence, SOCs and SH2-Bβ are not related. SOCs are induced in response to cytokines and appear to bind to JAK2 and inhibit its activity, and thus Stat function. They have not yet been shown to play a role in GH signaling. The present invention identifies SH2-Bβ in GH signaling. Since GH is a particularly robust activator of JAK2, identification and characterization of JAK2-interacting signaling molecules such as SH2-Bβ (and fragments thereof) and the cellular responses they initiate, further contributes to the understanding of GH action. Proteins like SH2-Bβ (and peptide fragments thereof) can serve as signaling molecules for multiple cytokines that activate JAK2. Thus, the findings of the present invention have broad implications for the treatment of multiple diseases (e.g. multiple sclerosis, obesity, some cancers, diseases of the immune system) for which ligands that activate JAK kinases are current or potential therapeutics.

C. SH2-Bβ, a JAK2 Binding Protein Regulated by GH and Other Cytokines and Growth Factors Identification of SH2-Bβ as a JAK2 binding protein: The following strategy was used to identify new GH signaling proteins that are recruited into GHR-JAK2 complexes by binding to JAK2. An N-terminal truncated JAK2 (ΔJAK2) fused to the DNA binding domain of Lex A was used as bait in a yeast two-hybrid screen of a rat adipocyte cDNA library. This approach was successful in identifying a splice variant of the SH2-domain containing protein SH2-B, designated SH2-Bβ, as a JAK2 interacting protein. The carboxyl-terminus of SH2-Bβ (SH2-Bβc), which contains the SH2 domain, specifically interacted with kinase-active, Tyr phosphorylated JAK2 but not the kinase-inactive, unphosphorylated JAK2 in the yeast two-hybrid system. Multiple approaches were used to verify that SH2-Bβ binds preferentially to Tyr phosphorylated JAK2. In support of SH2-Bβ serving as a GH signaling molecule, GH stimulated binding of SH2-Bβ to JAK2 as well as Tyr phosphorylation of SH2-Bβ in 3T3-F442A cells. Consistent with SH2-Bβ being a JAK2 substrate, SH2-Bβ was Tyr phosphorylated when co-expressed in COS cells with wild-type JAK2. These findings indicate that GH-induced activation and phosphorylation of JAK2 recruits SH2-Bβ and its associated signaling molecules to the GHR-JAK2 complex. Subsequent Tyr phosphorylation of SH2-Bβ allows it to recruit additional molecules (e.g. SH2- and PTB domain containing proteins) to GHR-JAK2 complexes. Thus, SH2-Bβ serves as an adapter molecule in GH signaling between GHR-JAK2 complexes and downstream signaling molecules (For details, See experimental section).

SH2-Bβ is a signaling molecule for multiple growth factors and cytokines: Other cytokines and growth factors also use SH2-Bβ as a signaling molecule. PDGF stimulates the association of SH2-Bβ with Tyr phosphorylated PDGF receptor (PDGFR) and the Tyr phosphorylation of SH2-Bβ. PDGF also stimulates the serine (Ser) and/or threonine (Thr) phosphorylation of SH2-Bβ. Studies, also implicate SH2-Bβ as a signaling molecule for IFNγ, LIF, insulin, NGF and EGF based on its ability to bind to receptor components (insulin, LIF), to be Tyr phosphorylated in response to ligand (IFNγ, LIF), and/or to be Ser/Thr phosphorylated in response to ligand (LIF, EGF, insulin, NGF). Ser/Thr phosphorylation appears to be mediated, at least in part, by MEK kinase or a kinase downstream of MEK (e.g., ERK½). Thus, SH2-Bβ appears to be a signaling molecule for multiple growth factors, cytokines and hormones and therefore plays a fundamental role in cell function.

D. Uses Of The Invention

The invention provides compositions and methods for identifying and testing tyrosine kinase JAK2 substrates and JAK2 kinase signaling pathway agonists and antagonists, and in particular, compositions comprising SH2-Bβ (and fragments thereof) which bind to activated, Tyr phosphorylated JAK2. A cDNA encoding SH2-Bβ and its translated amino acid product are shown in SEQ ID NOS: 1 and 2, respectively.

The polypeptide SH2-Bβ and fragments thereof, may have one or more SH2-Bβ-specific binding affinities which distinguish other SH2-B and SH2-B-related proteins such as APS, Lnk (See Yokouchi et al., *Oncogene* 15(1) :7–15, 1997) including the ability to specifically bind at least one natural human intracellular SH2-Bβ-specific binding target or a SH2-Bβ-specific binding agent such as a SH2-Bβ-specific antibody or a SH2-Bβ-specific binding agent identified in assays such as described below. Accordingly, the specificity of a SH2-BB3 fragment for specific binding agents is confirmed by ensuring non-cross reactivity with other SH2-B related proteins such as APS, Lnk. Furthermore, preferred SH2-Bβ fragments are capable of eliciting an antibody capable of distinguishing SH2-Bβ from other SH2-B proteins and the SH2-Bα isoform. Methods for making immunogenic peptides through the use of conjugates, adjuvants, etc. and methods for eliciting antibodies, e.g. immunizing rabbits, are well known. Exemplary natural intracellular binding targets include nucleic acids which comprise one or more SH2-Bβ binding sites and phosphotyrosine peptide fragments thereof, and protein kinases such as Janus tyrosine kinases JAK2, and fragments of such targets which are capable of SH2-Bβ-specific binding. Other natural SH2-Bβ binding targets and fragments thereof are readily identified by screening cells, membranes and cellular extracts and fractions with the disclosed materials and methods and by other methods known in the art. For example, two-hybrid screening using JAK2 kinases are used to identify intracellular targets which specifically bind such SH2-Bβ fragments. Preferred SH2-Bβ fragments retain the ability to specifically bind at least one JAK kinase binding site.

A wide variety of molecular and biochemical methods are available for generating and expressing SH2-Bβ fragments and JAK2 kinase. For example, the JAK2 and SH2-Bβ or fragments thereof may be obtained by chemical synthesis, expression in bacteria such as *E. coli* and eukaryotes such as yeast or vaccinia or baculovirus-based expression systems, etc., depending on the size, nature and quantity of the SH2-Bβ or fragment. The SH2-Bβ fragments are of length sufficient to provide a novel peptide. As used herein, such peptides are at least 5, usually at least about 6, more usually at least about 8, most usually at least about 10 amino acids. SH2-Bβ fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc. The same applies to the binding JAK2 kinase fragments.

The SH2-Bβ fragments maintain binding affinity of not less than six, preferably not less than four, more preferably not less than two orders of magnitude less than the binding equilibrium constant of a full-length native SH2-Bβ to the binding target under similar conditions. Particular SH2-Bβ fragments or deletion mutants are shown to function in a dominant-negative fashion. Particular SH2-Bβ fragments, for e.g. SH2-Bβn are also shown to prevent tyrosine phosphorylation of JAK2, thereby inhibiting JAK kinase activity. Such fragments provide therapeutic agents, e.g. when delivered by intracellular immunization—transfection of susceptible cells with nucleic acids encoding such mutants. The claimed SH2-Bβ and SH2-Bβ fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample.

The invention provides SH2-Bβ-specific binding agents, methods of identifying and testing such agents, and their use in diagnosis, therapy and pharmaceutical development. For example, SH2-Bβ-specific agents are useful in a variety of diagnostic applications, especially where disease or disease prognosis is associated with immune dysfunction resulting from improper expression of SH2-Bβ or due to the signaling pathways being modified by SH2-Bβ. Novel SH2-Bβ-specific binding agents include SH2-Bβ-specific antibodies; novel nucleic acids with sequence similarity to that of SH2-Bβ; isolated JAK2 Kinase binding domains; other natural intracellular binding agents identified with assays such as one- and two-hybrid screens; non-natural intracellular binding agents identified in screens of chemical libraries, etc.

The invention also provides nucleic acids encoding the subject SH2-Bβ and SH2-Bβ fragments thereof, the said nucleic acids may be part of SH2-Bβ-expression vectors and may be incorporated into recombinant cells for expression and screening, transgenic animals for functional studies, etc. In addition, the invention provides nucleic acids sharing substantial sequence similarity with that of one or more wild-type SH2-Bβ nucleic acids. Substantially identical or homologous nucleic acid sequences hybridize to their respective complements under high stringency conditions, for example, at 55° C. and hybridization buffer, comprising 50% formamide in 0.9M saline/0.09M sodium citrate (SSC) buffer and remain bound when subject to washing at 55° C. with the SSC/formamide buffer. Where the sequences diverge, the differences are preferably silent, i.e., a nucleotide change providing a redundant codon, or conservative, i.e. a nucleotide change providing a conservative amino acid substitution.

The nucleic acids find a wide variety of applications including use as hybridization probes, PCR primers, therapeutic nucleic acids, etc. for use in detecting the presence of SH2-Bβ genes and gene transcripts, for detecting or amplifying nucleic acids with substantial sequence similarity such as SH2-Bβ homologs and structural analogs, and for gene therapy applications (including antisense approaches). Given the subject probes, materials and methods for probing cDNA and genetic libraries and recovering homologs are known in the art. Preferred libraries are derived from human immune cells, especially cDNA libraries from differentiated and activated human lymphoid cells. In one application, the subject nucleic acids find use as hybridization probes for identifying SH2-Bβ cDNA homologs with substantial sequence similarity. These homologs in turn provide additional SH2-B and SH2-B fragments for use in binding assays and therapy as described herein.

Therapeutic SH2-Bβ nucleic acids are used to modulate, usually reduce, cellular expression or intracellular concentration or availability of active SH2-Bβ. These nucleic acids are typically antisense: single-stranded sequences comprising complements of the disclosed SH2-Bβ nucleic acids. Antisense modulation of SH2-Bβ expression may employ SH2-Bβ antisense nucleic acids operably linked to gene regulatory sequences. Cells are transfected with a vector comprising an SH2-Bβ sequence with a promoter sequence oriented such that transcription of the gene yields an antisense transcript capable of binding to endogenous SH2-Bβ encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a SH2-B or hSH2-B fragment may be administered to the target cell, in or temporarily isolated from a host, at a concentration that results in a substantial reduction in hSH2-Bβ expression. For gene therapy involving the transfusion of hSH2-Bβ transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The subject nucleic acids are often recombinant, meaning they comprise a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of SH2-Bβ modulatable cellular function, particularly SH2-Bβ mediated GH and PDGF signal transduction. Generally, these screening methods involve assaying for compounds which interfere with hSH2-Bβ activity such as hSH2-Bβ-JAK kinase binding, etc. The methods are amenable to automated, cost-effective high throughput drug screening and have immediate application in a broad range of domestic and international pharmaceutical and biotechnology drug development programs. Target therapeutic indications are limited only in that the target cellular function (e.g. gene expression) be subject to modulation, usually inhibition, by disruption of the formation of a complex comprising a hSH2-Bβ or hSH2-Bβ fragment and one or more natural hSH2-Bβ intracellular binding targets. Since a wide variety of genes are subject to JAK kinase regulated signaling, target indications may include viral, bacterial and fungal infections, metabolic disease, genetic disease, cell growth and regulatory disfunction, such as neoplasia, inflammation, hypersensitivity, etc. Frequently, the target indication is related to either immune dysfunction or selective immune suppression.

A wide variety of assays for binding agents are provided including labelled in vitro protein-protein and immunoassays for protein binding or complex formation, cell based assays such as two or three hybrid screens, transient transfection and co-immunoprecipitation assays, etc. For example, three-hybrid screens are used to rapidly examine the effect of transfected nucleic acids, which may, for example, encode combinatorial peptide libraries or antisense molecules, on the intracellular binding of hSH2-Bβ or hSH2-Bβ fragments to intracellular hSH2-Bβ targets. Convenient reagents for such assays (e.g. GST fusion partners) are known in the art.

hSH2-Bβ or hSH2-Bβ fragments used in the methods are usually added in an isolated, partially pure or pure form and are typically recombinantly produced. The hSH2-Bβ or fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring). The assay mixtures comprise at least a portion of a natural intracellular hSH2-Bβ binding target such as JAK2 kinase subunit domain. The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like. Where the agent is or is encoded by a transfected nucleic acid, said nucleic acid is typically DNA or RNA. Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs. A variety of other reagents may also be included in the mixture. These include reagents like salts, buffers, neutral proteins, e.g. albumin, detergents, etc. which may be used to facilitate optimal protein-protein binding and/or reduce non-specific or background interactions, etc. Also, reagents that otherwise improve the efficiency of the assay, such as protease inhibitors, nuclease inhibitors, antimicrobial agents, etc. may be used. The resultant mixture is incubated under conditions whereby, but for the presence of the candidate pharmacological agent, the SH2-Bβ specifically binds the cellular binding target, portion or analog. The mixture components can be added in any order that provides for the requisite bindings. Incubations may be performed at any temperature which facilitates optimal binding, typically between 4 and 40° C., more commonly between 15 and 40° C. Incubation periods are likewise selected for optimal binding but also minimized to facilitate rapid, high-throughput screening, and are typically between 0.1 and 10 hours, preferably less than 5 hours, more preferably less than 2 hours. After incubation, the presence or absence of specific binding between the hSH2-Bβ and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost. Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide. Detection may be effected in any convenient way. For cell based assays such as one, two, and three hybrid screens, the transcript resulting from hSH2-Bβ-target binding usually encodes a directly or indirectly detectable product (e.g. galactosidase activity, luciferase activity, etc.). For cell-free binding assays, one of the components usually comprises or is coupled to a label. A wide variety of labels may be employed, essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening.

Candidate agents shown to inhibit hSH2-Bβ-target binding provide valuable reagents to the pharmaceutical industries for animal and human trials. For example, SH2-Bβ fragments capable of blocking binding of said SH2-Bβ peptides, find use in treating disease associated with undesirable cell growth, differentiation, particularly immune cell differentiation, and growth factor/cytokine, particularly interleukin, more particularly GH, PDGF, NGF, EGF responsiveness. Also, the invention finds use in treating diseases associated with cell movement, particularly as changes in motility are important in growth and differentiation. Thus, it could be important in metastasis for cancer, in angiogenesis, in nerve regeneration and in embryogenesis, and maybe relevant in the prevention of apoptosis, treatment of diabetes, cancer, arthritis, immunological diseases, neurological diseases and others. For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 μg/kg of the recipient. For peptide agents, the concentration will generally be in the range of about 100 to 500 μg/ml in the dose administered. Other additives may be included, such as stabilizers, bactericides, etc. These additives will be present in conventional amounts.

DETAILED DESCRIPTION OF SPECIFIC EMBODIMENTS

A. Drug Screening Assays

In preferred embodiments, SH2-Bβ (and in particular, fragments of SH2-Bβ) are useful in drug screening assays designed to identify drugs that interfere with the specific binding of JAK2 kinases with its substrate as well as JAK2 kinase activity, and thereby block the activation of downstream signaling molecules.

In other embodiments, the invention provides an isolated SH2-Bβ polypeptide, or a fragment thereof, having JAK2 kinase-specific binding affinity. The invention provides nucleic acids encoding the SH2-Bβ polypeptide and SH2-Bβ fragments as part of expression vectors for introduction into cells. The invention provides methods of identifying intracellular molecules which interact with SH2-Bβ or SH2-Bβ fragments, as well as exogenous agents (i.e. drugs) which disrupt the binding of SH2-Bβ and/or fragments thereof to such intracellular targets.

The claimed polypeptide SH2-Bβ and SH2-Bβ fragments find particular use in screening assays for agents or lead compounds for agents useful in the diagnosis, prognosis or treatment of disease, particularly disease associated with undesirable cell growth, cell movement, differentiation and/or cytokine/growth factor signal responsiveness. One such assay involves forming mixtures of 1) SH2-Bβ (or fragments thereof) and 2) an intracellular SH2-B]3-binding ligand, in the presence or absence of 3) a prospective drug candidate. The mixtures are made under conditions that permit the binding of the intracellular SH2-Bβ-binding ligand to SH2-Bβ (or fragments thereof) and the mixtures are then analyzed for the presence of such binding. A difference in such binding in the presence of such a drug candidate indicates that the agent is capable of modulating the binding of SH2-Bβ (or fragments thereof) to an intracellular SH2-Bβ-binding ligand. The assays of the present invention provide for facile high-throughput screening of compounds suspected to be able to inhibit such binding (e.g., compound libraries, peptide libraries, and the like) to identify potential drug candidates.

An example of a drug screening assay, that can be employed to test for potential drug candidates that inhibit the specific binding of JAK2 kinases with its substrate SH2-Bβ, is given below. The suspect drug candidates are tested whether they block the binding of JAK2 to the full length SH2-Bβ, or preferably to the C-terminal portion of SH2-B (SH2-Bβc) fused to glutathione-S-transferase (GST). GST-SH2-Bβ or GST-SH2-Bβc is immobilized on glutathione-agarose beads and incubated for 1 hour with the indicated amount or different doses of the drug candidate. In parallel assays, anti-SH2-B or pre-immune serum (PI) are used as controls. Lysates from 3T3-F442A fibroblasts treated for 15 min with or without GH are incubated with the immobilized GST-SH2-Bβc in the presence or absence of the drug candidate (or in parallel assays with anti-SH2-B or PI). Alternatively, JAK2 and kinase inactive K882E JAK2 produced in Sf9 cells by a baculovirus expression system can be used. Bound proteins are eluted with sodium dodecyl sulfate-containing buffer, separated by SDS-PAGE and immunoblotted with αJAK2. GST-SH2-Bβc binds to JAK2 in a GH-dependent fashion. Treatment with anti-SH2-B (αSH2-B) (positive control) inhibits the binding of GST-SH2-Bβc to JAK2 in a dose-dependent fashion. In fact, 30 µl of αSH2-B almost completely abolishes the interaction of GST-SH2-Bβc with JAK2. Likewise, the ability of the drug candidate to inhibit binding of SH2-Bβ or fragments thereof, to JAK2 Kinase in fibroblast cells can be determined by comparison (For details see methodology and in particular Example 7 in the Experimental Section).

B. Signaling Molecules that Bind to SH2-Bβ.

In other embodiments, signaling molecules that bind to SH2-Bβ can be identified. Based on structural and functional features of SH2-Bβ (See experimental Section), SH2-Bβ appears to serve as an adapter molecule that recruits multiple signaling molecules to GHR-JAK2-SH2-Bβ complexes. It is believed that one or more of these proteins links GHR-JAK2-SH2-Bβ complexes to the cytoskeleton; and possibly to additional cellular functions. Signaling proteins are predicted either to bind to pTyr within SH2-Bβ in response to ligand or to bind constitutively to SH2-Bβ (e.g. via proline-rich regions). Identification of SH2-Bβ binding partners also would provide insight into signaling pathways initiated by GH, and also identify the role of SH2-Bβ in cellular actions of GH. The techniques for studying the interaction of the protein(s) of interest with SH2-Bβ and their role in cellular function are as described below and in the experimental section.

1. Clone new signaling proteins that bind SH2-Bβ using the yeast 2-hybrid system: SH2-Bβ contains several proline-rich regions, suggesting that it may bind to multiple proteins that contain SH3 or other proline-interacting domains. Since this interaction does not involve Tyr phosphorylation, it may be possible to identify such SH2-Bβ interacting proteins using the yeast 2-hybrid system, a popular strategy used to date, to study protein-protein interactions under physiological conditions. These SH2-Bβ interacting proteins may play an important role in the actions of SH2-Bβ because a number of ligands appear to recruit SH2-Bβ to receptors without stimulating detectable levels of Tyr phosphorylation of SH2-Bβ.

In one embodiment, bait proteins consisting of SH2-Bβ and the C-terminal portion of SH2-B containing the SH2 domain (SH2-Bβc) fused to epitope tagged yeast Lex A DNA binding domain, activated transcription in the absence of any candidate fusion proteins, rendering them unsuitable as bait. In another embodiment, a bait protein composed of the Lex A DNA binding domain fused to the N-terminal portion of SH2-Bβ (SH2-Bβn) alone, did not autoactivate. Hence, in preferred embodiments, the plasmids coding for bait protein can be transformed into the yeast host strain EGY48 by a standard lithium acetate protocol. Transformants can be isolated by growing on the proper selective medium (minus His) plates. β-galactosidase filter assays can be used to detect activation of the LacZ reporter gene. Expression of SH2-Bβn in yeast (blotted with αSH2-B) and its migration into the nucleus can then be verified. The LexA-SH2-Bβn fusion protein can be used as a bait to screen cDNA libraries (University of Maryland) to identify novel and important signaling molecules. Positive clones can be selected and verified as true 2-hybrid positive clones. Briefly, the prey plasmids would be recovered from the positive clones. The specificity of the interaction between SH2-Bβn and the candidate proteins can be verified by recotransforming EG48 yeast with the target plasmids isolated from the positive clones and a variety of different control bait plasmids (e.g. CD2, insulin receptor), including LexA DNA binding domain without insert or with several irrelevant inserts. The prey plasmids from true positive clones can be isolated and the inserts encoding candidate SH2-Bβn interacting proteins can be subsequently sequenced. The sequence with DNA and protein databases can be then compared using the BLAST server. Clones encoding sequences for JAK2, can thus be obtained, since JAK2 appears to bind to SH2-Bβn. Any such clones can also further help to define the regions of interaction between JAK2 and SH2-Bβn.

This approach may help in the identification of clones that express known proteins not presently recognized as binding to SH2-Bβ and also clones that express previously unidentified proteins. Especially, identification of proteins that have been or are thought to regulate the cytoskeleton, implicated in actions of GH or whose functions are known and likely to be important for GH signaling (e.g. actin binding proteins, guanine nucleotide exchange proteins, transcription factors). This can also help to define the role of that protein in GH signaling. The role for the candidate protein in GH signaling can be established by: 1) verifying that the protein co-immunoprecipitates with SH2-Bβ (ip with αSH2-B and blot with candidate Ab and vice versa), preferably but not necessarily in a GH-dependent manner; 2) examine whether the protein of interest is Tyr phosphorylated in response to GH (ip with candidate Ab and blot with αPY); and 3) examine whether the function (if known) of the protein is altered by GH (ip with candidate Ab and measure function). Alternatively, one can examine whether the protein is phosphorylated on Ser/Thr in response to GH (incubate cells with $^{32}$Pi, add vehicle or GH, ip with candidate Ab, SDS-PAGE, autoradiography), recruits proteins to JAK2 or regulates cellular functions if artifically targeted to the plasma membrane.

Clones that encode unknown proteins can be tested whether they encode a protein homologous to a protein of known function likely to play a role in GH signaling (e.g. Guanine nucleotide exchange protein, adapter protein, Tyr kinase, phospholipase, phosphatase). If the clone encodes an unknown protein, the EST cDNA databases can be searched, to test if additional sequence data are available. Also, candidate protein sequences can be examined for homology to proteins with known function or particular functional motifs (e.g. ATP binding site, zinc finger domain). Preferentially, proteins with homology to known signaling molecules likely to be important for GH function, and clones containing known functional motifs (e.g. zinc finger, SH2, SH3) would be selected. Next, it would be verified, whether the cDNA clone of interest encodes a protein that binds to SH2-Bβ, by subcloning the clone into a pGEX 5X vector to produce a GST fusion protein. The resulting GST fusion protein will be incubated with 3T3-F442A and CHO/GHR lysates from control and GH-treated cells. Bound proteins will be eluted and blotted with αSH2-B. Partial clones will be used to examine tissue distribution by Northern blot analysis using standard procedures as described previously or by RT-PCR. Preferentially, proteins whose mRNA shows a higher level of expression in known GH target tissues or are ubiquitously expressed would be targeted. A full-length cDNA would be obtained by 5' RACE PCR or with labeled cDNA of the original clone as a probe for screening a cDNA library. The cDNA library used would depend upon the tissue distribution of the protein. The full-length cDNA can be sequenced and analyzed by MacVector to provide insight into its function.

Once clones are identified, and verified that they encode proteins that associate in vitro with SH2-Bβ (especially, those that bind SH2-Bβ in a GH-dependent fashion or those homologous to proteins thought to regulate cellular morphology), polyclonal antibodies can be prepared to the candidate proteins. Also, it would be verified that SH2-Bβ and the candidate SH2-Bβ binding protein coprecipitate in vivo. It would be further determined whether the candidate protein exhibits functions predicted from its sequence (e.g. kinase activity, phosphatase activity) and whether that function is altered by GH or by binding to SH2-Bβ. The protein would be transiently expressed as a GFP fusion protein in cells and its distribution and effects on morphology assessed to see if it mimicks the effects of overexpressing SH2-Bβ in the presence and absence of GH and PDGF. From these experiments, one can gain insight into the protein's subcellular localization, the downstream functions the candidate protein might regulate, specific gene expression, and metabolic functions. These experiments would be carried out similarly to those described in the experimental section for SH2-Bβ, identified by a similar approach.

In other embodiments, other B42 acidic activation domain cDNA fusion libraries would be screened. Possible libraries that can be screened include brain, kidney, liver and lung which are either GH responsive tissues or known to express SH2-Bβ. Different bait constructs can be tried, including truncated versions of SH2-Bβn because smaller proteins are often more effective in this assay than larger proteins. The cDNA encoding SH2-Bβn can be cloned into a plasmid encoding the Gal4 DNA binding domain. Possible libraries include: rat brain (ClonTech), murine NIH 3T3 (Warner Lambert), and human B-lymphocyte (ClonTech) libraries. A number of proteins have been cloned that bind to SH3 domains or contain domains that interact with proline-rich regions using the yeast 2-hybrid assay, such as the LexA and Gal4 yeast 2-hybrid systems.

2. Clone new signaling molecules by screening I expression libraries with protein probes: One limitation of the yeast 2-hybrid system is that LexA SH2-Bβn can not be phosphorylated on Tyr and hence, cannot contain the portion of the protein corresponding to SH2-Bβc. Thus, in other embodiments, to identify proteins (e.g. those that contain PTB and SH2 domains) that bind to pTyr within SH2-Bβ, peptide screening of 1 expression libraries can be used. This system has been successfully exploited to examine intracellular protein interactions in mammalian cells, including in the identification of novel SH2 domain containing proteins that bind to pTyr in the EGF receptor. The cDNA encoding rat SH2-Bβ can be subcloned into the pGEX-2TK vector (Pharmacia) to encode an inframe GST fusion protein containing a thrombin cleavage site and a protein kinase A (PKA) phosphorylation site (GST-SH2-Bβ-A). The PKA site would allow the protein to be labeled to higher specific activity. GST-SH2-Bβ-A can be expressed in $E.\ coli$ and affinity purified by adsorption on immobilized glutathione. The immobilized fusion protein can be incubated with purified baculovirus expressed JAK2 in the presence of ~1 mCi [g-$^{32}$P]ATP, followed by several min with 30–50 mM unlabeled ATP to ensure maximal phosphorylation. Since, GST-SH2-Bβ can be phosphorylated by activated JAK2 in vitro, it can be verified by proteolytic digestion and 2-D phosphopeptide mapping, that the sites within SH2-Bβ that can be phosphorylated in vitro by JAK2 are the same as those phosphorylated in vivo and establish conditions that result in maximal phosphorylation. Unlabeled ATP can be removed by washing and [γ-$^{32}$P]ATP added in the presence of protein kinase A catalytic subunit (Sigma). The PKA catalytic subunit can be added after JAK2 to avoid the possibility that phosphorylation of SH2-Bβ by JAK2, may adversely affect by prior phosphorylation of SH2-Bβ on PKA sites. The catalytic subunit can be removed by washing. SH2-Bβ-A incubated only with PKA and not with JAK2 would serve as a good negative control. Also, conditions can be altered as necessary to achieve a high stoichiometry of phosphorylation and a high level of incorporated radioactivity ($1\times10^7$ dpm/mg), essential for this approach to succeed. The immobilized $^{32}$P-fusion protein would be treated with thrombin to release $^{32}$P-SH2-Bβ-A from GST-glutathione-agarose. In preferred embodiments, baculovirus-produced JAK2 appeared to be highly phosphorylated, indicating it is enzymatically active as reported previously. Also, one can Tyr phosphorylate the GST-cytoplasmic domain of GHR expressed in bacteria using JAK2 prepared from GH-treated 3T3-F442A cells, suggesting that the approach of phosphorylating bacterial SH2-Bβ in vitro with JAK2 is reasonable. Also, GST is not phosphorylated by JAK2 in that assay.

One can determine whether proteins immobilized on nitrocellulose filters (used in screening) can be detected with [$^{32}$P]SH2-Bβ. As a positive control, it can be verified, that 10–20 ng of Tyr phosphorylated JAK2 spotted onto nitrocellulose binds detectable amounts of $^{32}$P-SH2-Bβ, using GST fused to the PKA phosphorylation site as a negative control. Since, affinity of SH2-Bβ for K882E JAK2 is quite low, K882E JAK2 would serve as a second negative control. The amount of [$^{32}$P]SH2-Bβ necessary for detection can be accordingly optimized. Stringency of the screen can be improved, by testing different detergents, blocking agents, and concentrations as well as by varying the time and temperature of incubation.

If binding of [$^{32}$P]SH2-Bβ to JAK2, is detected, [$^{32}$P]SH2-Bβ can be used as a probe to screen a variety of expression libraries, including murine fat cell, liver, skeletal muscle or brain library (Clontech). To screen the library, phage would be plated and the plates overlaid with nitrocellulose filters impregnated with IPTG. After incubating overnight, the filters would be removed, washed and blocked. $^{32}$P-SH2-Bβ would be added and the filters incubated overnight. The washed and dried filters would be analyzed by autoradiography. Positive clones would be rescreened. The same plaques would be screened with SH2-Bβ-$^{32}$P-PKA which had not been incubated with JAK2 to identify proteins that bind to regions of SH2-Bβ that do not contain pTyr. If any proteins bind to phosphorylated Tyr within SH2-Bβ, then the cDNA encoding their pTyr binding domain (presumably SH2 or PTB domain) would be subcloned into 1EX1ox and used as a positive control for each library screen. Phages which are positive after a second round of screening would then be analyzed. They would be subcloned into M13 and then sequenced. The sequence would be compared with all DNA and protein data bases available using the BLAST server.

Both approaches (1) and (2) would help in identifying signaling molecules that bind to SH2-Bβ.

C. Identify Compounds that Bind to SH2-Bβ and Inhibit JAK2 Tyrosine Kinase Activity.

In preferred embodiments, particular SH2-Bβ fragments or deletion mutants can be identified that inhibit JAK2 kinase activity. These have been observed to function in a dominant-negative fashion in inhibiting JAK2 tyrosine kinase activity. Particular SH2-Bβ fragments, for e.g. SH2-Bβn have been found to prevent tyrosine phosphorylation of JAK2, thereby inhibiting JAK kinase activity. Such fragments provide therapeutic agents, e.g. when delivered by intracellular immunization—transfection of susceptible cells with nucleic acids encoding such mutants. (For more details, see Example 6 in the Experimental Section).

EXPERIMENTAL

The following examples serve to illustrate certain preferred embodiments and aspects of the present invention and are not to be construed as limiting the scope thereof. In the experimental disclosure which follows, the following methodology apply:

METHODOLOGY

Cells and reagents: *Saccharomyces cerevisiae* EGY48 MATa, trp1, ura3-52, , his3, leu) and all yeast expression plasmids were obtained from ClonTech. The stock of PC12 cells and NIH 3T3 cells were obtained from ATCC. Recombinant human GH and porcine insulin were from Eli Lilly and Co., Indianapolis, Ind. Recombinant human PDGF-BB was from Life Technologies. Recombinant human PDGF-AA, murine EGF, and munne NGF were from Collaborative Biomedical Products. Recombinant protein A-agarose, sold under the trademark IMMOBILIZED PROTEIN A (An affinity matrix of PROTEIN A and agarose) was from Repligen. Recombinant murine IFNγ and glutathione-agarose beads were from Sigma Co., St. Louis, Mo. Expand™ high fidelity PCR system, alkaline phosphatase, aprotinin, leupeptin, and TRITON X-100 [octylphenolpoly (ethyleneglycolether)$_x$] were from Boehringer Mannheim. Protein phosphatase 2A (PP2A) was from Upstate Biotechnology Inc. Enhanced chemiluminescence detection system was from Amersham Corp. The nucleic acid and amino acid sequences for Human platelet-derived growth factor receptor (GENBANK ACCESSION No. J03278), Murine growth hormone receptor (GENBANK ACCESSION No. U15011) and Human nerve growth factor receptor (GENBANK ACCESSION No. M14764) are available.

Antibodies: Antibodies to SH2-Bβ (αSH2-B) were raised by immunizing 3 rabbits with GST-SH2-Bβc. Briefly, GST-SH2-Bβc fusion proteins were eluted from the glutathione-agarose beads with elution buffer (10 mM reduced glutathione, 50 mM Tris-HCl, pH 8.0). The purity was estimated to be >95% as determined by Coomassie blue staining of SDS-PAGE gels. Antisera to GST-SH2-Bβc were produced at Pocono Rabbit Farm & Laboratory Inc. and used at a dilution of 1:100 for immunoprecipitation and 1:10,000 for immunoblotting. Anti-JAK2 antiserum (αJAK2) was raised in rabbits against a synthetic peptide corresponding to amino acids 758–776 and was used at a dilution of 1:500 for immunoprecipitation and 1:15,000 for immunoblotting. Monoclonal anti-phosphotyrosine antibody 4G10 (γPY) was purchased from Upstate Biotechnology Inc and was used at a dilution of 1:7,500 for immunoblotting. Monoclonal antibody to influenza hemagglutinin (HA)-tag (αHA, 12CA5) was purchased from Boehringer Mannheim and was used at a dilution of 1:100 for immunoprecipitation. Monoclonal antibody against Myc-tag ((αMyc, 9E10) was from Santa Cruz Biotechnology, Inc. and used at a dilution of 1:1000 for immunoblotting.

Plasmid construction: cDNAs encoding both wild-type murine JAK2 and mutant murine JAK2 in which the critical lysine in the ATP-binding domain is mutated to glutamate (K882E) were previously cloned into mammalian expression vector pRK5, (See Schematic B, below). BamHI and EcoRI sites were added to 5' - and 3'-end of the JAK2 cDNAs via polymerase-chain reaction (PCR), respectively. Full-length JAK2 cDNAs (both wild-type and K882E mutant) were first cloned into pBluescript-SK(-) (Stratagene), and then subcloned in-frame into the LexA bait plasmid (pEG202) [obtained from ClonTech] at BamHI-SalI sites. An amino-terminal truncated JAK2 (ΔJAK2) bait hybrid plasmid was constructed by subdloning the XhoI-SalI fragment of wild-type or mutant JAK2 cDNA into pEG202. The cytoplasmic domain of CD2 was generated by reverse transcription-PCR and cloned into pEG202 at EcoRI-BamHI sites. Construction of the bait plasmid containing a portion of Drosophila bicoid protein or the cytoplasmic domain of the insulin receptor, and construction of the prey plasmid harboring the acidic transcriptional activation domain of B42 fused to human Shc, human insulin receptor substrate-1, (IRS-1) or the PTB domain of IRS-1, have been described (Carparo et al., *J. Biol. Chem*.270:1563,1995; O'Neill et al., *Mol. Cell. Biol.* 14:6433, 1994; Zervos et al., *Cell* 72:223, 1994). The cDNA encoding the carboxyl-terminal portion of SH2-Bβ(SH2-Bβc) was isolated from the prey plasmid obtained from yeast-two hybrid screening of a rat fat cDNA library (see below) and subcloned in-frame into the GST vector pGEX-5X (Pharmacia Biotech. Inc) using EcoRI-XhoI sites and into the pcDNA3 expression vector (InVitrogen) with an HA-tag at the amino-terminus of SH2-Bβc. The cDNA fragment encoding the entire SH2 domain of SH2-Bβ was produced by PCR using customized primers and cloned in-frame into pGEX-5X. All PCR products and all junctions were verified by DNA sequencing.

Rat adipose cDNA library: RNA was prepared from epididymal fat pads of Sprague-Dawley rats (10 month old) using TRIZOL reagent (Life Technologies), according to the manufacturer's protocol. Poly (A)+RNA was prepared using oligo (dT) cellulose. Oligo (dT)-XhoI linker-primed cDNA was synthesized using a kit (Stratagene), according to the manufacturer's protocol, except that Klenow fragment and mung bean nuclease were utilized to blunt the cDNA prior to ligation with the EcoRI linker. The cDNA was ligated into the EcoRI/XhoI sites of the pJG4-5 activation domain plasmid and electroporated into XL1-Blue MRF' (Stratagene). Approximately $1 \times 10^6$ independent isolates were obtained. Plasmid DNA was purified using Mega kit (QIAGEN).

Two-hybrid library screening and cloning full-length SH2-Bβ: Screening was carried out essentially as described. Yeast (EGY48) were grown at 30° C. in YPD medium containing 1% yeast extract, 2% polypeptone, and 2% dextrose. Yeast were sequentially transformed with the LexAop-lacZ reporter plasmid, pEG202-DJAK2 bait plasmid and cDNA library prey plasmids by the lithium acetate method. Triple transformants were grown for 4 hours in liquid yeast drop-out medium lacking Trp, Ura, His, and subsequently plated on the same drop-out medium with the addition of 15% agar. Yeast were grown for 4 days at 30° C., then colonies were collected and replated on yeast drop-out medium lacking Trp, Ura, His and Leu to select for Leu prototrophy. The carbon source was also changed from dextrose to galactose to induce the expression of the activation domain hybrids. After 5 days of growth, colonies were subjected to filter lift color assay to test for β-galactosidase activity. Positive clones were selected and prey plasmids containing library cDNA inserts were isolated and transformed into bacteria for amplification. The insertion cDNAs were subjected to DNA sequence analysis. Total RNA was prepared from kidney of Sprague-Dawley rats using TRIZOL reagent (Life Technologies). Oligo (dT) primed cDNA was synthesized using a kit (Stratagene), and used subsequently as source DNA to obtain full-length SH2-Bβ by PCR using 5'-primer (SEQ ID NO: 5):

(5'-GTGGATCCATGAATGGTGCCCCTTCCCCAGAG-GATG-3') flanking the start codon of SH2-Bα and 3'-primer (SEQ ID NO: 6):

(5'-CGGAATTCTCAGACAAATGAGTACTGGTTATTA-3') flanking the stop codon of SH2-Bα. To facilitate the following cloning process, BamHI and EcoRI sites had been integrated into 5'- and 3'-primers, respectively. The PCR product was cloned into pGEX-KG (Guan and Dixon, *Anal. Biochem.* 192, 262–267, 1991) (See Schematic C, below) to produce GST fusion protein.

pGEX-KG was constructed as follows. A synthetic oligonucleotide linker was inserted into the EcoRl site of pGEX-2T to create pGEX-KG. The sequence of the linker is shown in Schematic C. The filled thick arrow, represents the coding sequence for glutathione S-transferase (GST). The one-letter symbols of amino acid residues which are in frame with GST are shown above the nucleotide sequence while the unique restriction sites in the polycloning site are indicated under the nucleotide sequence. Unique restriction sites are also indicated. The location of genes for ampicillin resistance (Amp$^r$) and the Lac repressor (LacI$^q$) are denoted by thin arrows (→).

The PCR product was also cloned into mammalian expression vector pRK5 with a Myc-tag at the amino-terminus. However, it is not intended that the compositions of the present invention be limited by the nature of the expression vector. A variety of mammalian expression vectors having a CMV promoter, are contemplated. The entire PCR-produced SH2-Bβ cDNA was sequenced using a set of customized primers by the DNA Sequencing Core in the Univeristy of Michigan.

Cell culture, lysis and transfection: Mouse 3T3-F442A preadipocytes were grown in DMEM (supplemented with 1 mM L-glutamine, 100 U/ml penicillin, 100 mg/ml streptomycin, 0.25 mg/ml amphotericin, and 10% calf serum). PC12 cells were grown in DMEM, supplemented with 1 mM L-glutamine, 100 U/ml penicillin, 100 mg/ml streptomycin, 0.25 mg/ml amphotericin, and 10% heat-inactivated horse serum and 5 fetal bovine serum. The confluent cells were deprived of serum overnight. The deprived cells were treated for various times with GH, insulin, PDGF-AA, PDGF-BB, NGF, EGF, or IFNγ at 37° C. at the indicated concentrations and times, then rinsed three times with ice-cold PBSV (10 mM sodium phosphate, pH 7.4, 150 mM NaCl, 1 mM Na$_3$VO$_4$). Cells were solubilized in lysis buffer (50 mM Tris, pH 7.5, 0.1% TRITON X-100, 150 mM NaCl, 2 mM EGTA, 1 mM Na$_3$VO$_4$, 1 mM phenylmethylsulfonyl fluoride, 10 mg/ml aprotinin, 10 mg/ml leupeptin), and centrifuged at 14,000×g for 10 min at 4° C. The supernatant was utilized for immunoprecipitation, immunoblotting, or in vitro binding assays.

To lyse yeast cells, exponentially growing cultures (O.D.$_{600}$~1.0) were washed once with ice-cold H$_2$O, suspended in 50 mM Tris, pH 7.5, 150 mM NaCl, 2 mM EGTA, 1 mM Na$_3$VO$_4$, 1 mM phenylmethylsulfonyl fluoride, 10 mg/ml aprotinin, 10 mg/ml leupeptin, 500 mg/ml acid-washed glass beads, and vortexed at 4° C. for 5 min. The mixtures were centrifuged at 14,000×g for 10 min at 4° C. and the supernatant utilized for immunoblotting or immunoprecipitation.

COS cells were transiently transfected by calcium phosphate precipitation (Frederick M. Ausubel, *Current protocols in molecular biology*, 1996: 9.1.4–11) and assayed 48 hours after transfection. For each 100 mm culture dish, 5 mg of each construct was used and the total amount of DNA was adjusted to 10 mg by adding empty pcDNA3 vector.

In vitro interaction assay using GST fusion proteins: GST fusion proteins were purified from bacteria by affinity chromatography with glutathione-agarose beads. 3T3-F442A cells were treated with or without GH, and whole cell lysates were prepared as described above. The immobilized fusion proteins were incubated with the cell lysates at 4° C. for 3 hours, followed by extensive washing with lysis buffer. The proteins bound to the immobilized GST fusion proteins were solubilized by boiling for 5 min in a mixture (80:20) of lysis buffer and sodium dodecyl sulfate (SDS)-polyacrylamide gel electrophoresis (PAGE) sample buffer (250 mM Tris-HCl, pH 6.8, 10% SDS, 10% β-mercaptoethanol, 40% glycerol, 0.01% bromophenol blue), separated by SDS-PAGE, transferred onto nitrocellulose, and subsequently immunoblotted with antibody to JAK2 or phosphotyrosine.

Immunoprecipitation and Immunoblotting: Cell lysates were incubated with the indicated antibody on ice for 2 hours. The immune complexes were collected on protein A-agarose (25 ml) during one hour incubation at 4° C. The beads were washed 3 times with washing buffer (50 mM Tris, pH 7.5, 0.1% TRITON X-100, 150 mM NaCl, 2 mM EGTA) and boiled for 5 min in a mixture (80:20) of lysis buffer and SDS-PAGE sample buffer. The solubilized proteins were separated by SDS-PAGE (5–12% gradient gel unless noted otherwise) followed by immunoblotting with the indicated antibody using the enhanced chemiluminescence detection system. Some membranes were then incubated at 55° C. for 30–60 min in stripping buffer (100 mM b-mercaptoethanol, 2% SDS, 62.5 mM Tris-HCl, pH 6.7). The membranes were then immunoblotted with the desired antibody. In some cases, the blots were reprobed immediately without stripping with a second antibody.

Far-Western Blot: COS cells were transfected with 5 mg pRK5 containing cDNA encoding either wild-type or kinase-inactive murine JAK2. JAK2 was immunoprecipitated with αJAK2, separated by SDS-PAGE and transferred onto nitrocellulose. The membrane was incubated with GST-SH2-Bβc (1.5 mg/ml) at 4° C. overnight. After extensive washing with lysis buffer, the membrane was then immunoblotted with αSH2-B.

Dephosphoiylation: 3T3-F442A preadipocytes were treated with 500 ng/ml GH for 15 min, and the cell lysates were immunoprecipitated with αSH2-B (1:100 dilution). The immunoprecipitates were incubated for 60 min at 37° C. in 100 ml dephosphorylation buffer (50 mM Tris-HCl, 0.1 mM EDTA, pH 8.5, 1 mM phenylmethylsulfonyl fluoride, 10 mg/ml aprotinin, 10 mg/ml leupeptin, 40 U alkaline phosphatase) with or without 5 mM Na$_3$VO$_4$. The reaction was terminated and proteins were eluted by boiling in a mixture (80:20) of lysis buffer and SDS-PAGE sample buffer. As controls, the immunoprecipitates were treated identically except no alkaline phosphatase was added. Similarly, αSH2-B immunoprecipitates were treated with 0.5 U PP2A at 37° C. for 40 min, and the resultant dephosphorylated proteins were resolved by SDS-PAGE and immunoblotted with αSH2-B.

Figure 14:
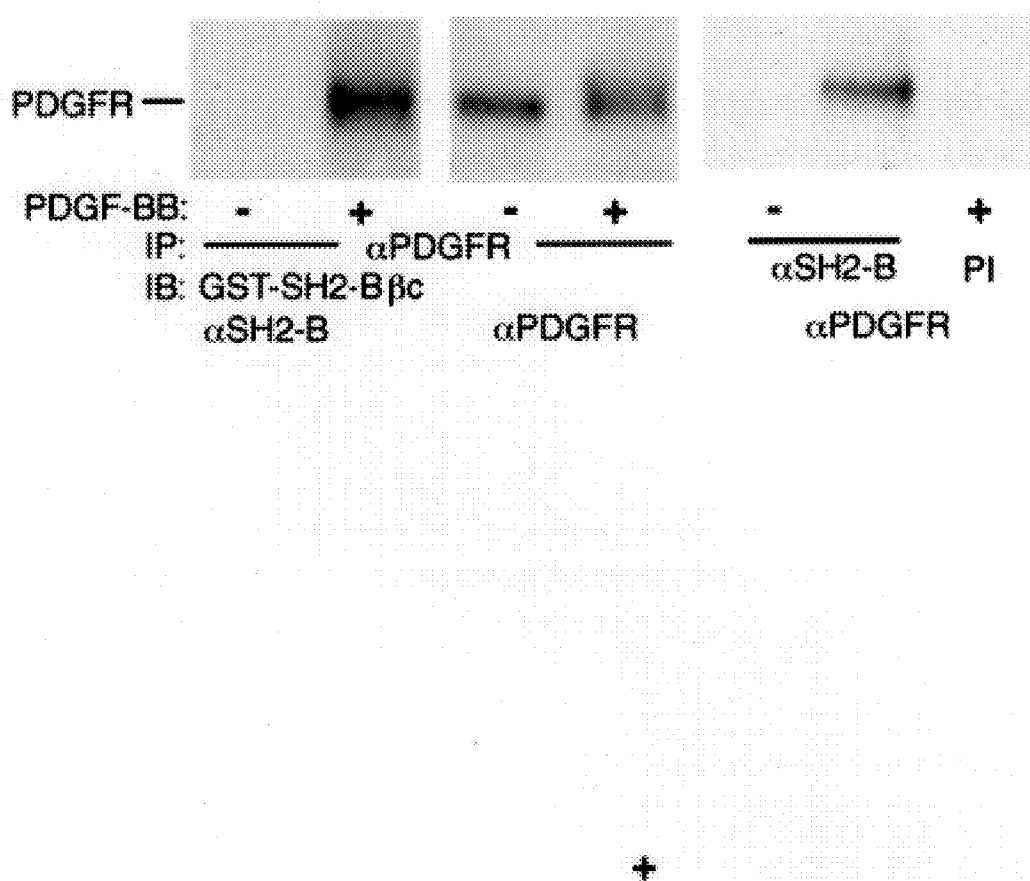
FIG. 14 is a photograph of a representative immunoblot showing PDGF stimulates association of SH2-Bβ with PDGF receptor both in vitro and in vivo in 3T3-F442A cells. Lysates were immunoprecipitated with αPDGFR, αSH2-B or pre-immune serum (PI) and blotted with either αPDGFR or GST-SH2-Bβ followed by αSH2-B.

GST fusion protein pull-down assay, immunoprecipitation, immunoblotting and Far Western blotting assays for PDGF experiments: 3T3-F442A fibroblasts were treated for 10 min with 25 ng/ml PDGF-BB, vehicle or other ligands as indicated in FIG. 14. For GST fusion protein pull-down assays, whole cell lysates were precipitated with GST fusion proteins immobilized on glutathione-agarose beads and subsequently immunoblotted with αPDGFR or αPY as described previously. For immunoprecipitation, cell lysates were incubated with the indicated antibody on ice for 2 hours. The immune complexes were collected on protein A-agarose (50 μl) during one hour incubation at 4° C. In some experiments, αSH2-B immunoprecipitates were dephosphorylated by alkaline phosphatase or PP2A as described previously. The immunoprecipitates were immunoblotted with the indicated antibody as described previously. Some membranes were stripped by incubation at 55° C. for 30–60 min in stripping buffer (100 mM β-mercaptoethanol, 2% SDS, 62.5 mM Tris-HCl, pH 6.7) and reprobed with a different antibody. For Far Western blotting, PDGFR was immunoprecipitated with αPDGFR from solubilized 3T3-F442A fibroblasts, separated by SDS-PAGE and transferred onto nitrocellulose. The nitrocellulose was incubated with GST-SH2-Bβc (1.5 μg/ml) at 4° C. overnight. After extensive washing with TBS-Tween, the membrane was immunoblotted with αSH2-B. The blot was stripped and reprobed with αPDGF and αPY sequentially.

EXAMPLE 1

Figure 1B:
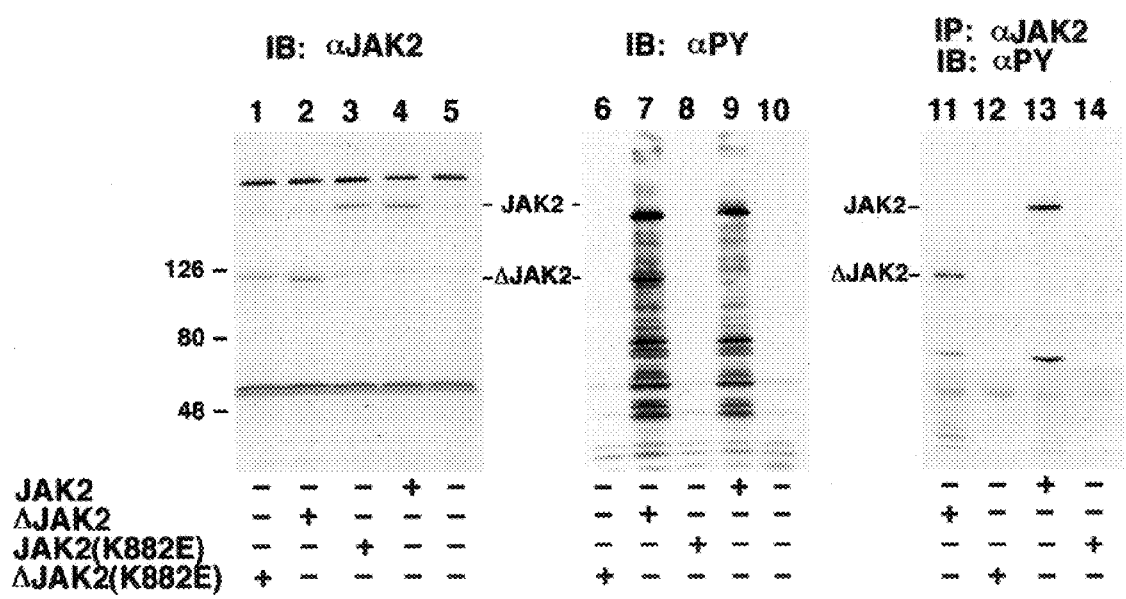
FIG. 1(B) is a photograph of a representative gel showing proteins in whole cell lysates of the yeast transformants (transformed with the indicated JAK2 bait hybrids) immunoblotted (IB) with αJAK2 (lanes 1–5) or αPY (lanes 6–10). In parallel experiments, proteins in yeast cell lysates were immunoprecipitated (IP) with αJAK2 and immunoblotted with αPY (lanes 11–14).

In this example, the experimental data obtained shows that SH2-Bβ binds activated JAK2. Murine JAK2 has 49 Tyr residues. These residues, if phosphorylated, could serve as docking sites for SH2 or PTB-domain containing signaling molecules. Therefore, experiments were designed to identify proteins that are recruited to JAK2-GHR complexes by binding to pTyr within JAK2. The C-terminus of JAK2 was used as bait in a yeast 2-hybrid system to screen for JAK2 interacting proteins (See FIG. 1A). When expressed in yeast, the lexA-ΔJAK2 bait fusion protein is an active Tyr kinase, as illustrated by its Tyr phosphorylation and the Tyr phosphorylation of multiple yeast proteins (See FIG. 1B). Using a rat adipocyte cDNA library, a splice variant of the SH2-domain containing protein SH2-B, designated SH2-Bβ, was identified as a JAK2 interacting protein. The carboxyl-terminus of SH2-Bβ (SH2-Bβc), which contains the SH2 domain (See FIG. 2C), specifically interacted with the kinase-active, Tyr phosphorylated ΔJAK2 and full-length JAK2 (See FIG. 1C), but not with unphosphorylated kinase-inactive truncated or full-length K882E JAK2 in the yeast 2-hybrid system. To examine whether JAK2 and SH2-Bβ interact in mammalian cells, antibodies (Abs) to SH2-Bβc fused to glutathione-S-transferase (GST) were prepared. Abs prepared from 3 rabbits were found to immunoprecipitate (ip) and western blot SH2-Bβ. These Abs theoretically would recognize both SH2-Bβ and SH2-Bα, since the antigen contains the shared SH2 domain of the 2 isoforms. The Abs are therefore designated αSH2-B. However, they have little affinity for the SH2 domain, and are therefore relatively specific for SH2-Bβ. When expressed in COS cells with JAK2, SH2-Bβ co-immunoprecipitated wild-type, Tyr phosphorylated JAK2 to a significantly greater extent than kinase-inactive, unphosphorylated JAK2 (See FIG. 4). SH2-Bβc also bound to wild-type but not kinase-inactive JAK2 in a Far western blot (See FIG. 5). The results show that SH2-Bβ binds specifically to Tyr phosphorylated, activated JAK2.

EXAMPLE 2

Figure 6:
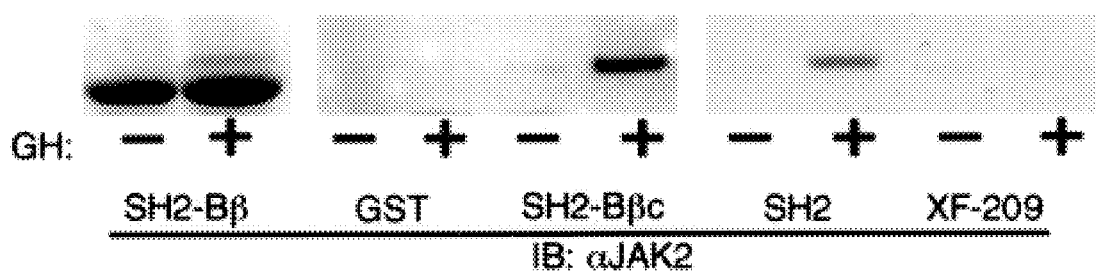
FIG. 6 is a photograph of a representative immunoblot showing GH promotes binding of JAK2 to GST fusion proteins containing SH2-Bβ or the SH2 domain of SH2-Bβ in 3T3-F442A fibroblasts. Cell lysates were incubated with the indicated GST-fusion proteins and the bound proteins were blotted with αJAK2.
Figure 7:
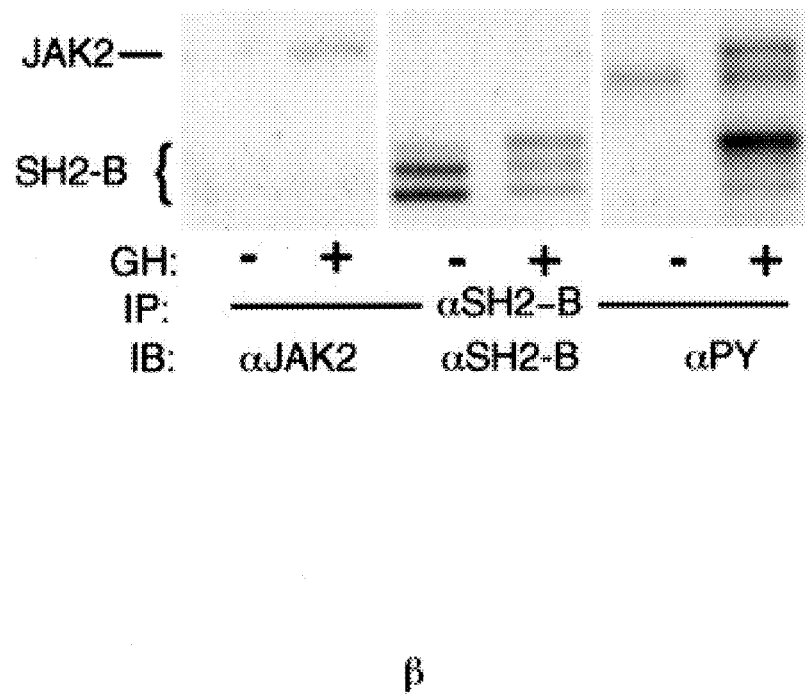
FIG. 7 is a photograph of a representative immunoblot showing GH stimulates association of endogenous SH2-Bβ with JAK2 and tyrosyl phosphorylation of SH2-Bβ in 3T3-F442A fibroblasts. Proteins in cell lysates were immunoprecipitated with αSH2-B and blotted with the indicated antibody.
Figure 8:
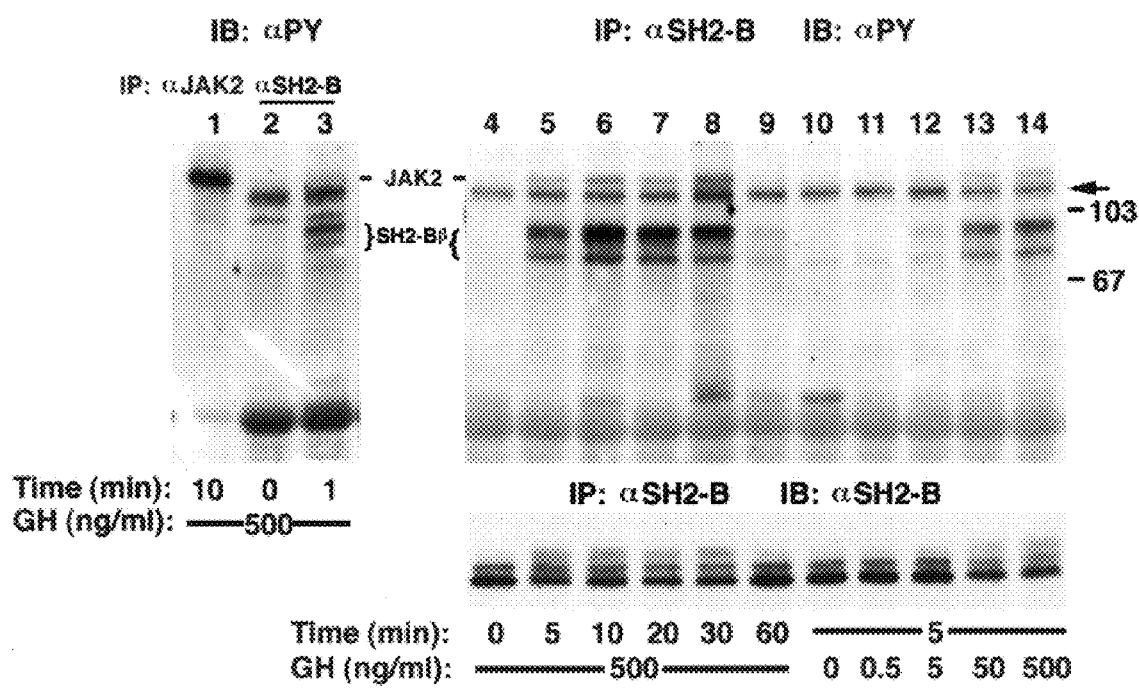
FIG. 8 is a photograph of a representative immunoblot showing the time-course and dose-response of GH-stimulated tyrosyl phosphorylation of SH2-Bβ in 3T3-F442A cells. Whole cell lysates were immunoprecipitated with αSH2-B (lanes 2–14), separated by SDS-PAGE (7% gel) and immunoblotted with αPY (lanes 1–14 upper panel). Blots corresponding to lanes 4–14 were reprobed without stripping with αSH2-B (lanes 4–14, lower panel). To determine the location of JAK2, cell lysates were immunoprecipitated with αJAK2 and immunoblotted with αPY (lane 1).
Figure 9:
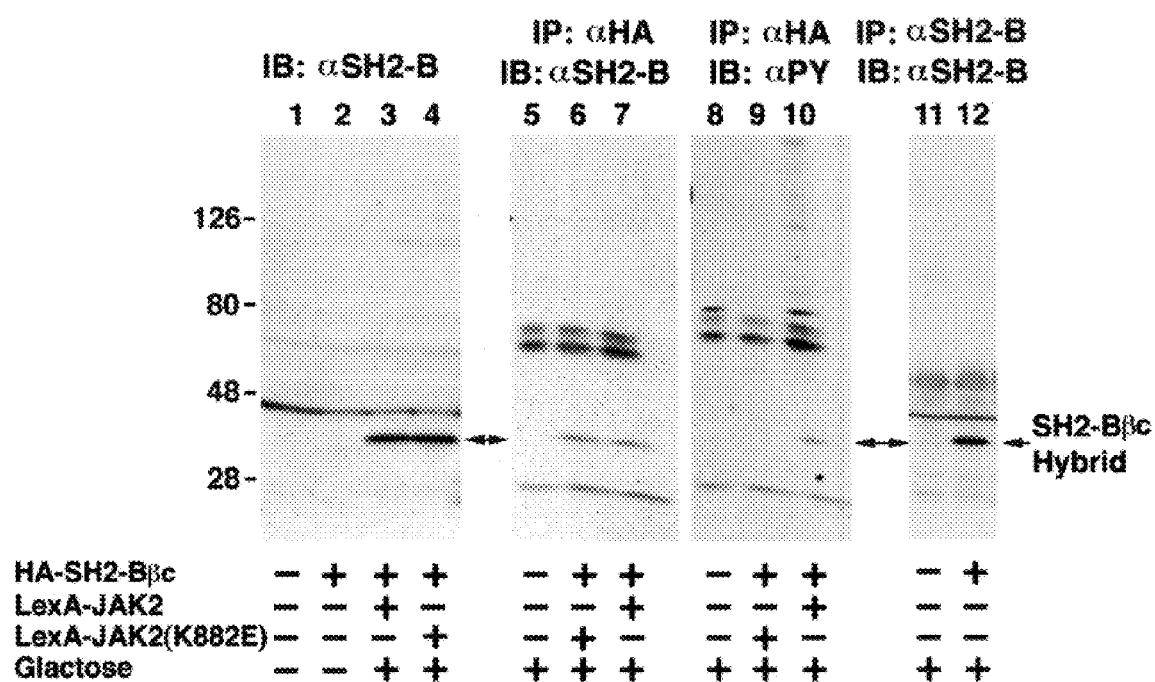
FIG. 9 is a photograph of a representative immunoblot showing immunoprecipitation of SH2-Bβ by αSH2-B. Yeast were transformed with plasmids encoding the indicated fusion proteins. Expression of the HA-tagged SH2-Bβc-activation domain hybrid was not induced (lanes 1–2) or induced with galactose (lanes 3–12). Whole cell lysates from the yeast transformants were separated by SDS-PAGE and immunoblotted with αSH2-B (lanes 1–4). In parallel experiments, yeast lysates were immunoprecipitated with αHA (lanes 5–7) or αSH2-B (lanes 11–12) and immunoblotted with αSH2-B (lanes 5–7, 11–12). The blot corresponding to lanes 5–7 was reprobed with αPY (lanes 8–10).
Figure 10A:
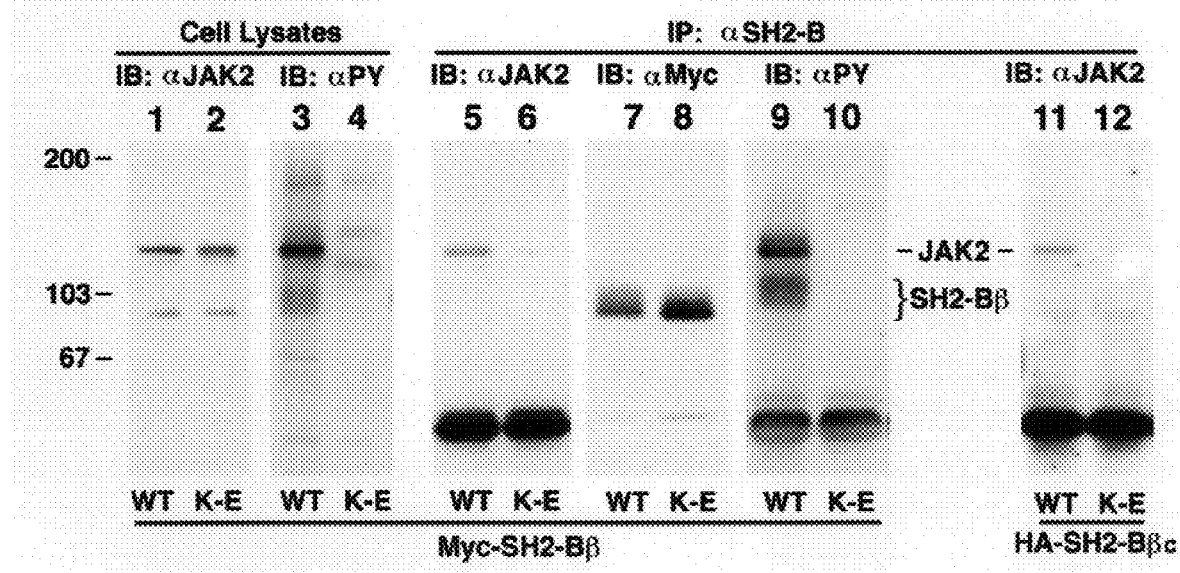
FIG. 10(A) is a photograph of an immunoblot representing SH2-Bβ (lanes 1–10) or SH2-Bβc (lanes 11 and 12) co-expressed in COS cells with either wild-type (WT, lanes 1, 3, 5, 7, 9 and 11) or kinase-inactive (K-E, lanes 2, 4, 6, 8, 10 and 12) JAK2. Whole cell lysates (lanes 1–4) or αSH2-B immunoprecipitates (lanes 5–12) were separated by SDS-PAGE and immunoblotted with αJAK2 (lanes 1–2, 5–6 and 11–12). The blots corresponding to lanes 1, 2, 5 and 6 were directly reprobed with αPY and αMyc, respectively without stripping. The blot corresponding to lanes 7–8 was stripped and reprobed with αPY (lanes 9–10).
Figure 10B:
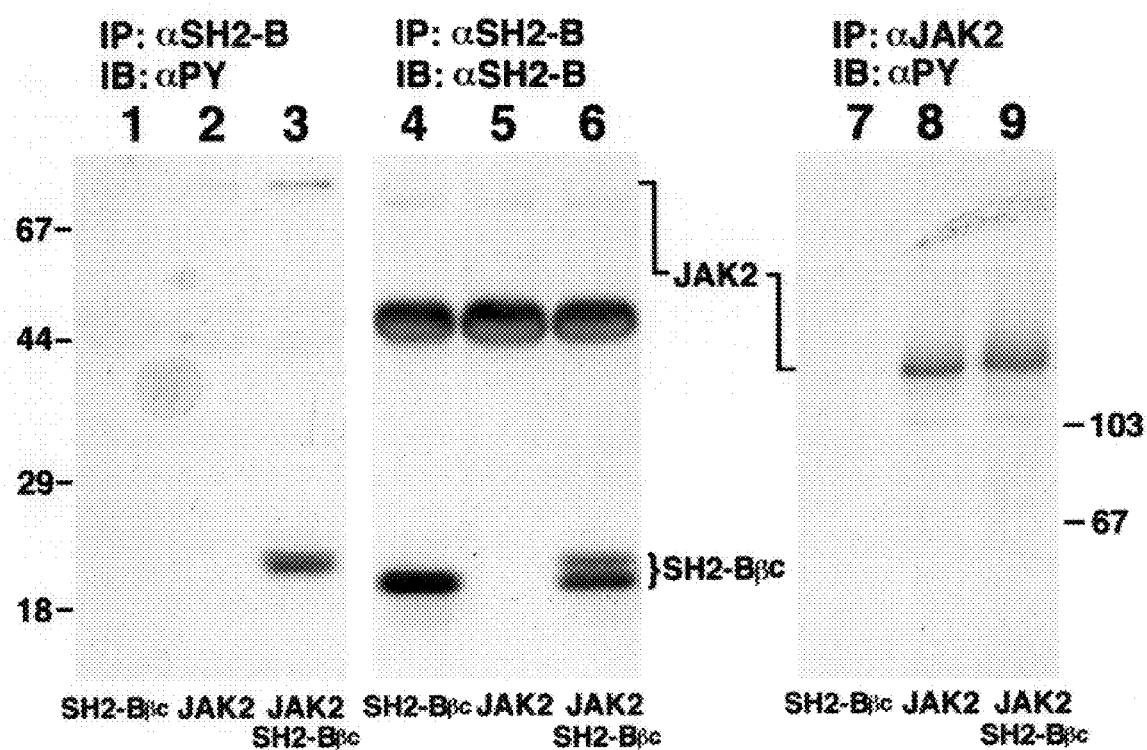
FIG. 10(B) is a photograph of an immunoblot representing COS cells transiently transfected with pcDNA3 encoding HA-tagged SH2-Bβc (lanes 1, 3, 4, 6, 7 and 9) and/or prk5 encoding murine JAK2 (lanes 2, 3, 5, 6, 8 and 9). Whole cell lysates were immunoprecipitated with either αSH2-B (1:100 dilution, lanes 1–3) or αJAK2 (lanes 7–9), separated by SDS-PAGE (15% gel) and immunoblotted by αPY (lanes 1–3, 7–9). The blot corresponding to lanes 1–3, was reprobed with αSH2-B (lanes 4–6). The migration of molecular weight standards (x10$^{-3}$), JAK2 and SH2-Bβc, as indicated.
Figure 11:
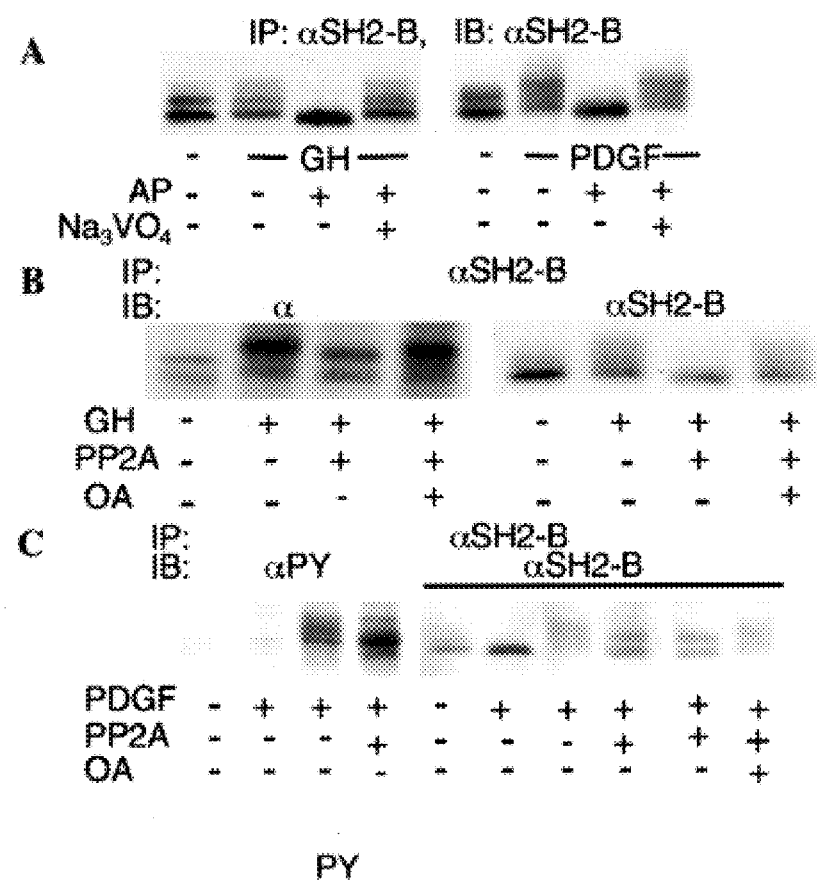
FIG. 11 is a photograph of a representative immunoblot showing SH2-Bβ is phosphorylated on Ser/Thr as well as Tyr in 3T3-F442A cells stimulated with hGH or PDGF-BB. αSH2-B immunoprecipitates were dephosphorylated by alkaline phosphatase (AP) in the presence or absence of Na3VO4 (AP inhibitor) (Panel A) or PP2A in the presence or absence of okadaic acid (OA, PP2A inhibitor) (Panels B and C), and were blotted with αSH2-B or αPY as indicated.

In this example, GH stimulates the binding of SH2-Bβ to JAK2 and Tyr phosphorylation of SH2-Bβ. In 3T3-F442A cells, GH stimulated the interaction of SH2-Bβ with pTyr of JAK2 both in vitro as assessed by binding of JAK2 in cell lysates to GST-SH2-Bβc or GST-SH2-Bβ fusion proteins (See FIG. 6), and in vivo as assessed by co-immunoprecipitation of JAK2 with SH2-Bβ (See FIG. 7). GH promoted a transient and dose-dependent Tyr phosphorylation of SH2-Bβ in 3T3-F442A cells (FIG. 8), further suggesting the involvement of SH2-Bβ in GH signaling. Consistent with SH2-Bβ being a substrate of JAK2, SH2-Bβc is Tyr phosphorylated when co-expressed with wild-type, but not kinase-inactive JAK2 in both yeast (FIG. 9) and COS cells (See FIG. 10). Full-length SH2-Bβ is also Tyr phosphorylated when co-expressed with JAK2 in COS cells (See FIG. 4). Dephosphorylation of SH2-Bβ from GH-treated cells using the Ser/Thr protein phosphatase 2A (PP2A) results in two bands of Tyr phosphorylated SH2-Bβ (See FIG. 11), suggesting that SH2-Bβ is phosphorylated at 2 or more Tyr. The data indicates that GH-induced activation and pTyr of JAK2 recruits SH2-Bβ into a GHR-JAK2 complex, resulting in Tyr phosphorylation of SH2-Bβ and the creation of pTyr binding sites for some as yet unidentified signaling molecules.

EXAMPLE 3

Figure 3B:
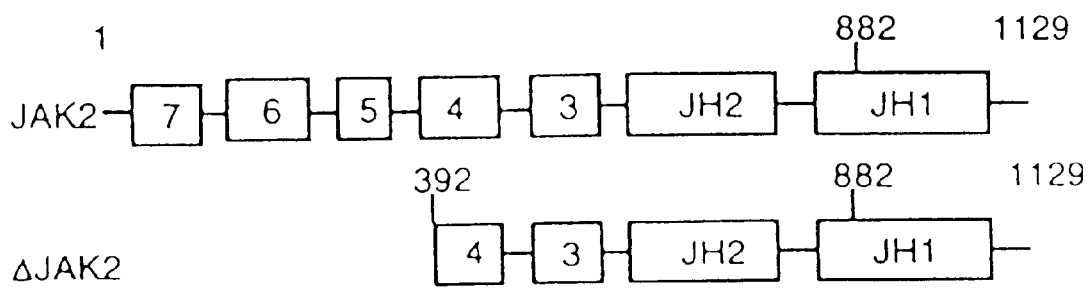
FIG. 3B is a representation of murine JAK2 and its mutant.

This example shows SH2-Bβ and JAK2 have at least 2 sites of interaction. To gain insight into the recruitment of SH2-Bβ to JAK2, studies were initiated to determine the regions of JAK2 and SH2-Bβ required for JAK2-SH2-Bβ complex formation. In initial studies, by using a yeast 2-hybrid screen and the C-terminal portion of JAK2, a clone encoding SH2-Bβc was identified (See FIG. 2C), indicating that at least one site of interaction between JAK2 and SH2-Bβ lies within both C-termini. SH2-Bβc consists primarily of the SH2 domain and binds only to Tyr phosphorylated JAK2 (See FIG. 4), suggesting that the SH2 domain of SH2-Bβ binds to pTyr in the C-terminal portion of JAK2. This region in JAK2 contains the kinase domain, kinase like domain, 2 known pTyr and 25 additional potential pTyr sites (See FIG. 3B). Binding of SH2-Bβc to activated JAK2 was substantiated by co-immunoprecipitation assays using over-expressed proteins in COS cells (See FIG. 4), Far western blots (See FIG. 5) and binding assays using GST-SH2-Bβc (See FIG. 6). In support of the interaction being mediated by the SH2 domain of SH2-Bβ, the SH2 domain of SH2-Bβ alone also bound activated JAK2, as assessed by JAK2 binding to the SH2 domain fused to GST (See FIG. 6).

Figure 4:
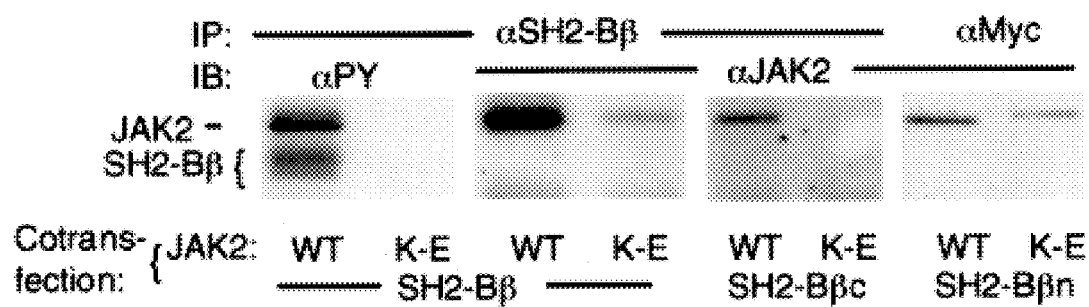
FIG. 4 is a photograph of a representative immunoblot showing SH2-Bβ has at least two binding sites for JAK2; site 1 at the N-terminal end and site 2 at C-terminus (SH2 domain). Lysates from COS cells transiently cotransfected with JAK2 (WT, wild type) or K882E JAK2 (K-E, kinase inactive) and Myc-tagged SH2-Bβ or its truncated mutants, were immunoprecipitated and blotted with the indicated antibody.
Figure 5:
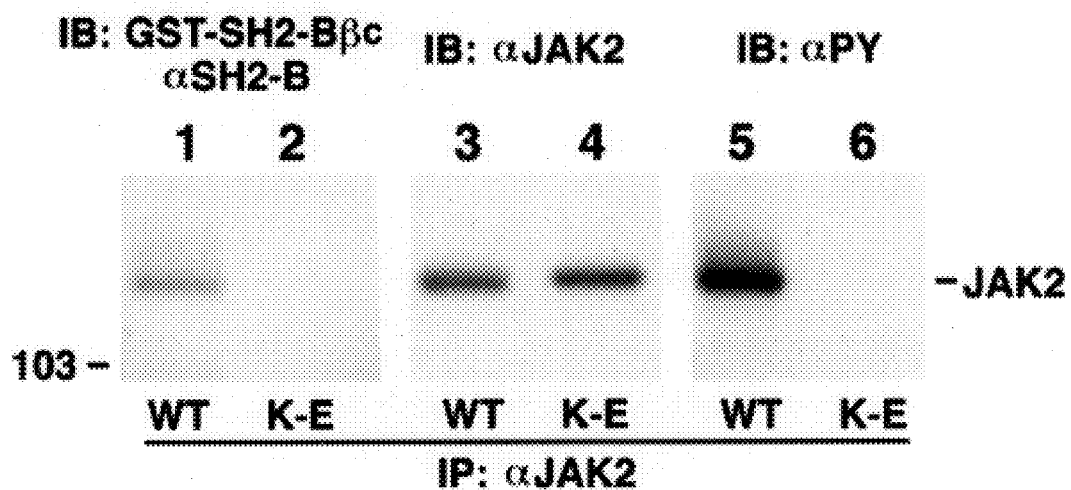
FIG. 5 is a photograph of a representative immunoblot showing SH2-Bβ interacts directly with tyrosyl phosphorylated JAK2. COS cells were transiently transfected with prk5 encoding JAK2 wild-type (lanes 1, 3 and 5) or kinase-inactive (lanes 2, 4 and 6) murine JAK2. JAK2 was immunoprecipitated with αJAK2, separated by SDS-PAGE and transferred onto nitrocellulose and then incubated with GST-SH2-Bβ. Subsequently, the membrane was immunoblotted with αSH2-B (lanes 1–2). The same blot was reprobed with αJAK2 (lanes 3–4) and αPY (lanes 5–6).

Full-length SH2-Bβ also showed a marked preference for Tyr phosphorylated, kinase-active compared to unphosphorylated, inactive K882E JAK2 (See FIG. 4). However, some SH2-Bβ co-precipitated with kinase-inactive JAK2 (See FIG. 4), in contrast to the finding with SH2-Bβc and the SH2 domain of SH2-Bβ (See FIGS. 4, 6, data not shown). In the same assay, low levels of N-terminal portion of SH2-Bβ (SH2-Bβn, See FIG. 2C) co-precipitated to similar extents with kinase-active and -inactive JAK2 (See FIG. 4). Furthermore, a small amount of endogenous SH2-Bβ in 3T3-F442A cells bound to JAK2 in the absence of GH (See FIG. 7). In this example, the experimental findings suggest that SH2-Bβ and JAK2 have two sites of interaction: a site in the N-terminus of SH2-Bβ (site 1) that binds with low affinity to inactive JAK2 and the SH2-Bβ SH2 domain (site 2) that binds with high affinity to active JAK2. Once bound to JAK2 via its high affinity site, SH2-Bβ becomes a JAK2 substrate, resulting in creation of pTyr binding sites for downstream signaling proteins.

EXAMPLE 4

This example shows that SH2-Bβ is multiply phosphorylated on Ser and/or Thr residues. When SH2-Bβ from 3T3-F442A cells was immunoprecipitated using antibodies to SH2-B, and then subjected to immunoblotting with antibodies to SH2-B, the best resolved gels revealed 3 bands in control cells and 3–4 in GH-treated cells (See FIGS. 7, 8). All bands from GH-treated cells contained pTyr proteins as judged by reprobing the blots with Ab to pTyr (αPY) (See FIG. 7). In contrast, although there are also multiple SH2-Bβ bands in the control cells, SH2-Bβ is not Tyr phosphorylated (See FIGS. 7,11). This suggested that either SH2-Bβ exists as multiple isoforms or is phosphorylated on Ser/Thr. To differentiate between these possibilities, SH2-Bβ was dephosphorylated using a non-specific phosphatase (alkaline phosphatase) and a Ser/Thr specific phosphatase (PP2A). Both phosphatases caused the multiple bands present in the control cells to condense into one band, migrating either with or just below the fastest migrating band. The change in band pattern was blocked by phosphatase inhibitors (vanadate for alkaline phosphatase and okadaic acid for PP2A) (See FIGS. 11A,11B). In GH-treated cells, alkaline phosphatase also reduced the multiple bands to one (See FIG. 11A), whereas PP2A reduced the bands to two. This suggested that in control cells, SH2-Bβ is phosphorylated on multiple Ser/Thr residues and that GH stimulates the phosphorylation of SH2-Bβ on 2 or more Tyr residues. Sequence analysis revealed potential phosphorylation sites for protein kinase A (PKA), protein kinase G (PKG), casein kinase II, ERK1 and 2, and protein kinase C. The experimental finding in this example, raises the possibility that regulation of the phosphorylation of Ser/Thr residues could form a basis for cross-talk among other pathways initiated by GH (like MAP kinase, PKC) or by other ligands (e.g. those that activate PKA). Thus, this example suggests that phosphorylation of Ser/Thr residues may play an important role in regulating SH2-Bβ function.

EXAMPLE 5

Figure 12:
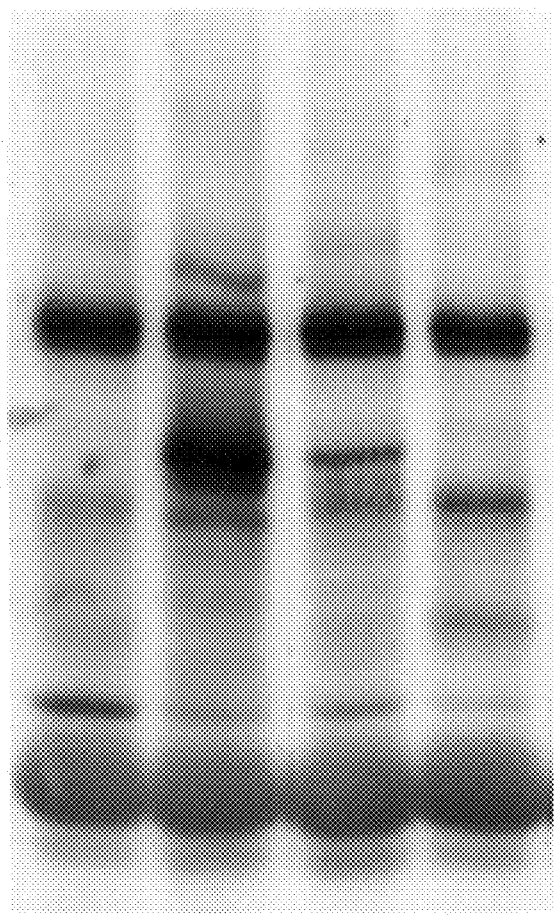
FIG. 12 is a photograph of a representative immunoblot showing ligand-dependent tyrosyl phosphorylation of SH2-Bβ in response to GH (lane 2), IFNγ (lane 3) but not insulin (Ins, lane 4). Whole cell lysates were immunoprecipitated with αSH2-B (upper panel) or αJAK2 (lower panel) and immunoblotted with αPY. The migration of molecular weight standards (x10$^{-3}$), JAK2 and SH2-Bβ is as indicated.
Figure 12:
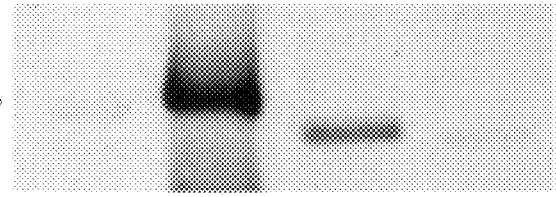

This example shows that multiple cytokines and growth factors regulate SH2-Bβ. JAK2 associates with multiple cytokine receptors, in addition to GH receptor (Argetsinger, L. S. and Carter-Su, *Physiol. Rev.* :76(4): 1089–1107, 1996). Therefore, it was investigated whether LIF and IFN-γ, two cytokines that activate JAK2 in 3T3-F442A cells, also utilize SH2-Bβ as a signaling molecule. Both LIF and IFN-γ (See FIG. 12) stimulated the pTyr of SH2-Bβ. The level of LIF and IFNγ induced pTyr of SH2-Bβ was significantly less as compared to the response seen to GH, as predicted from the lower levels of JAK2 autophosphorylation (See FIG. 12). However, while the amount of Tyr phosphorylation of SH2-Bβ in response to LIF was barely detectable, LIF induced a decrease in SH2-Bβ mobility to an extent similar to GH (FIG. 13 and data not shown), suggesting that LIF increases Ser/Thr phosphorylation of SH2-Bβ. In addition, αSH2-B precipitated Tyr phosphorylated proteins that co-migrated with LIF receptor subunits LIFRβ and gp130 (See FIG. 13). The experimental data in this example, thus provides evidence that SH2-Bβ serves as a signaling molecule for multiple cytokine receptors that activate JAK2, and also that SH2-Bβ may transmit a signal, via its Tyr and/or via its Ser/Thr phosphorylation. In addition, the data indicates that for some receptors, SH2-Bβ may be recruited to JAK2-receptor complexes by binding to receptor subunits in addition to JAK2 binding.

Because cytokine receptors and receptor tyrosine kinases (RTKs) utilize some of the same signaling molecules, it was further determined whether SH2-Bβ is a signaling molecule for ligands that activate RTKs. Data obtained indicates that SH2-Bβ serves as a signaling molecule for PDGF, EGF, NGF and insulin. Moreover, by 3 different assays, it was shown that SH2-Bβ binds to the PDGF receptor (PDGFR) in a PDGF dependent fashion: 1) PDGF-dependent co-precipitation of endogenous PDGFR with endogenous SH2-Bβ (See FIG. 14); 2) binding in a Far Western blot of GST-SH2-Bβc to PDGFR only from PDGF treated 3T3-F442A cells (See FIG. 14); and 3) binding to GST-SH2-Bβ of PDGFR only from PDGF-treated 3T3-F442A cells (data not shown). Binding appeared to be mediated at least in part via the SH2 domain of SH2-Bβ, based on PDGFR binding to GST-SH2 domain of SH2-Bβ (data not shown). Interestingly, PDGF stimulated both the Tyr and Ser/Thr phosphorylation of SH2-Bβ in contrast to GH which stimulated the pTyr of SH2-Bβ and LIF which stimulated primarily the Ser/Thr phosphorylation of SH2-Bβ. As seen with GH, when SH2-Bβ from PDGF-treated cells was treated with PP2A, the slower migrating, broad diffuse band condenses to 2 more well defined bands migrating below and in the midst of the broad diffuse band (See FIG. 11C). This suggested that PDGF stimulates the phosphorylation of SH2-Bβ on more than one Tyr residue. Consistent with at least some of the phosphorylation being on Ser/Thr in addition to Tyr, PDGF caused a more substantial decrease in mobility than GH, but a lower degree of Tyr phosphorylation (as judged by blotting with αPY) (data not shown). In this example, the data obtained indicated that PDGF stimulated the association of SH2-Bβ with PDGFR as well as the Tyr and Ser/Thr phosphorylation of SH2-Bβ.

Figure 13:
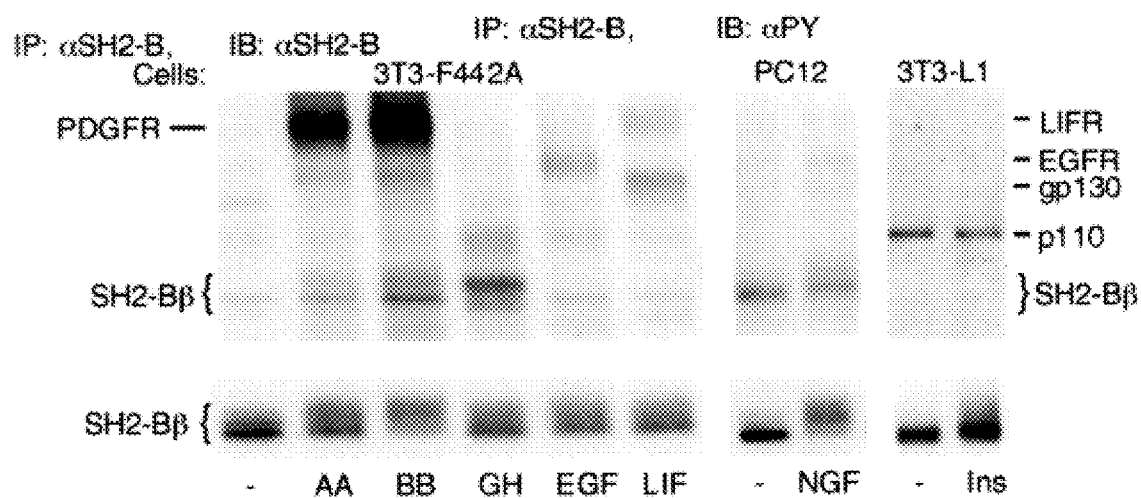
FIG. 13 is a photograph of a representative immunoblot showing SH2-Bβ is involved in the signaling of multiple ligands. 3T3-F442A cells were stimulated with PDGF-AA, PDGF-BB, hGH, EGF, or LIF. PC12 and 3T3-LI adipocytes were stimulated with NGF and Insulin (Ins) respectively. Proteins in the lysates were immunoprecipitated with αSH2-B and blotted with αPY (upper panel) or αSH2-B (lower panel).

Similar to PDGF and LIF, NGF, EGF and insulin also promoted the Ser/Thr phosphorylation of SH2-Bβ (See FIG. 13). The greatest phosphorylation was observed for NGF in PC12 cells. In contrast to PDGF, GH and IFNγ, other ligands such as NGF, EGF, insulin did not appear to stimulate the Tyr phosphorylation of SH2-Bβ. The evidence obtained by using the yeast 2-hybrid system, as well as the binding of insulin receptor from 3T3-F442A cells to SH2-Bβc suggested that SH2-Bβ forms a complex with the insulin receptor, although the affinity appears to be significantly reduced when compared to that for the JAK2 or PDGFR. Thus, the experimental results in this example indicated that SH2-Bβ is recruited to Tyr kinase signaling pathways in response to multiple ligands that activate receptor tyrosine kinases. Information regarding how SH2-Bβ functions as gained by studying the cellular actions of GH also provides insight into the functions of other growth factors, cytokines and hormones which use the same signaling pathway.

Figure 15:
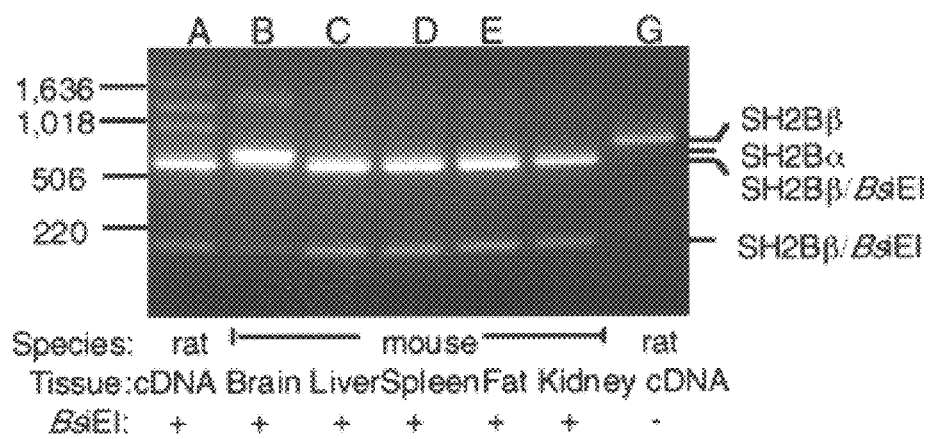
FIG. 15 is a photograph of a representative gel electrophoresis of RT-PCR amplification products, showing that SH2Bβ is present in all tissues tested and the dominant isoform in most tissues. Lanes B–F; Total RNA from mouse tissue was reverse transcribed using Superscript II enzyme (Gibco BRL). Lanes A, G: SH2Bβ cDNA from rat kidney. PCR using 0.3 μM of oligonucleotide probes [complemented base pairs 1692 (5' tctcccctagttctgcctccattg 3') to 2429 (5' cgcccccgacgcctcttct 3')], flanking the unique 100 bp insert in SH2Bβ were used to amplify the DNA. Gel purified DNA was digested with BsiEI which cleaves sequences found only in the insert. The migration of PCR products of SH2Bβ (737 bp), SH2Bα (637 bp), and the BsiEI digest of SH2Bβ (588/149 bp) are noted.

Next, the tissue distribution of SH2-Bα and β was examined by PCR, using primers that surrounded the 100 bp insert. Based on the larger size of the PCR product, its digestion by a restriction enzyme that cuts only within the insert, and co-migration with the PCR product using rat kidney SH2-Bβ cDNA as template, SH2-Bβ was found to be expressed in every tissue that was tested (fat, spleen, liver, kidney and brain) and was more predominant than SH2-Bα in all tissues with exception of the brain (See FIG. 15). In 3T3-F442A cells, SH2-Bβ was also the predominant isoform based upon its apparent Mr when dephosphorylated and the co-migration of the dephosphorylated form that was expressed in COS cells. Similarly, EST database searches revealed EST encoding the C-terminal portion of SH2-Bβ that were from kidney, embryo, brain, liver/spleen and fibroblast. No ESTs were detected that encoded the C-terminal portion of SH2-Bα (i.e.which lacked the 100 bp insert). This example indicates that SH2-Bβ is expressed in many tissues, including multiple GH-responsive tissues. Its apparent wider distribution makes it likely to be a more general regulator of cellular function than SH2-Bα. Nonetheless, although this example demonstrates the role of SH2-Bβ, it should be recognized that many of the results will also be relevant to SH2-Bα, because the shared SH2 domain of SH2-Bβ appears to play a major role in its interactions with receptors with intrinsic or associated tyrosine kinase activity.

EXAMPLE 6

Figure 16:
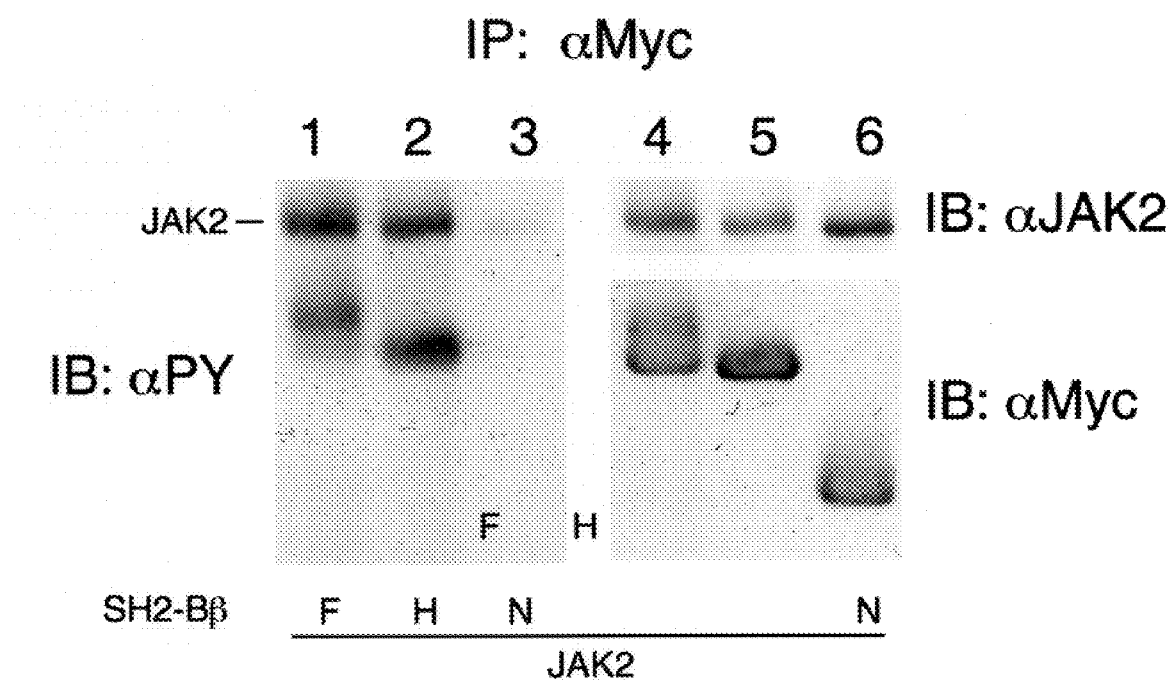
FIG. 16 is a photograph of a representative immunoblot showing C-terminally truncated SH2-Bβ associates with JAK2 and inhibits JAK2 tyrosyl phosphorylation. Myc-tagged SH2-Bβ or truncated SH2-Bβ were coexpressed with JAK2 in COS cells and αMyc were immunoprecipitated, blotted with αPY (lanes 1–3). The same blot was reprobed with αJAK2 (lanes 4–6, upper panel) or αMyc (lanes 4–6, lower panel). [F: full length; H: truncated with SH-2 domain (amino acids 1–631); N: truncated without SH2 domain (amino acids 1–555)].
Figure 17A:
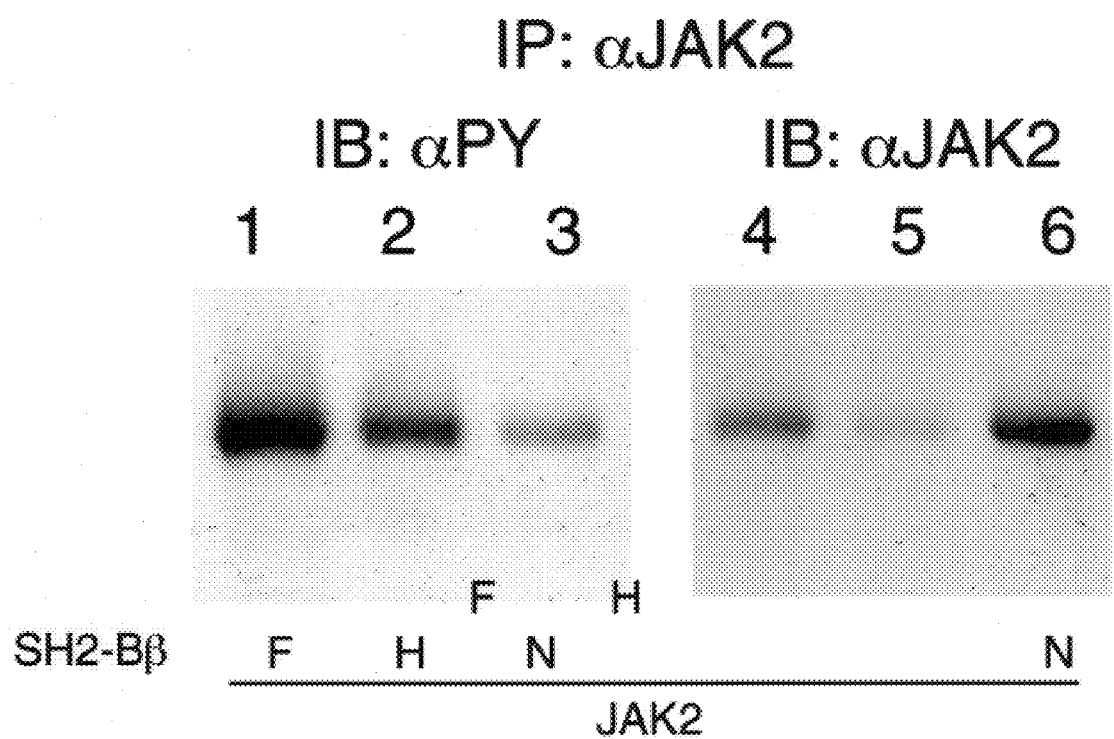
FIG. 17A is a photograph of a representative immunoblot showing C-terminally truncated SH2-Bβ inhibits JAK2 tyrosyl phosphorylation of JAK2 in COS cells. Myc-tagged SH2-Bβ or truncated SH2-Bβs were coexpressed with JAK2 in COS cells, JAK2 immunoprecipitated with αJAK, and immunoblotted with αPY (lanes 1–3), or αJAK2 (lanes 4–6). [F: full length; H: truncated with SH-2 domain (amino acids 1–631); N: truncated without SH2 domain (amino acids 1–555).
Figure 17B:
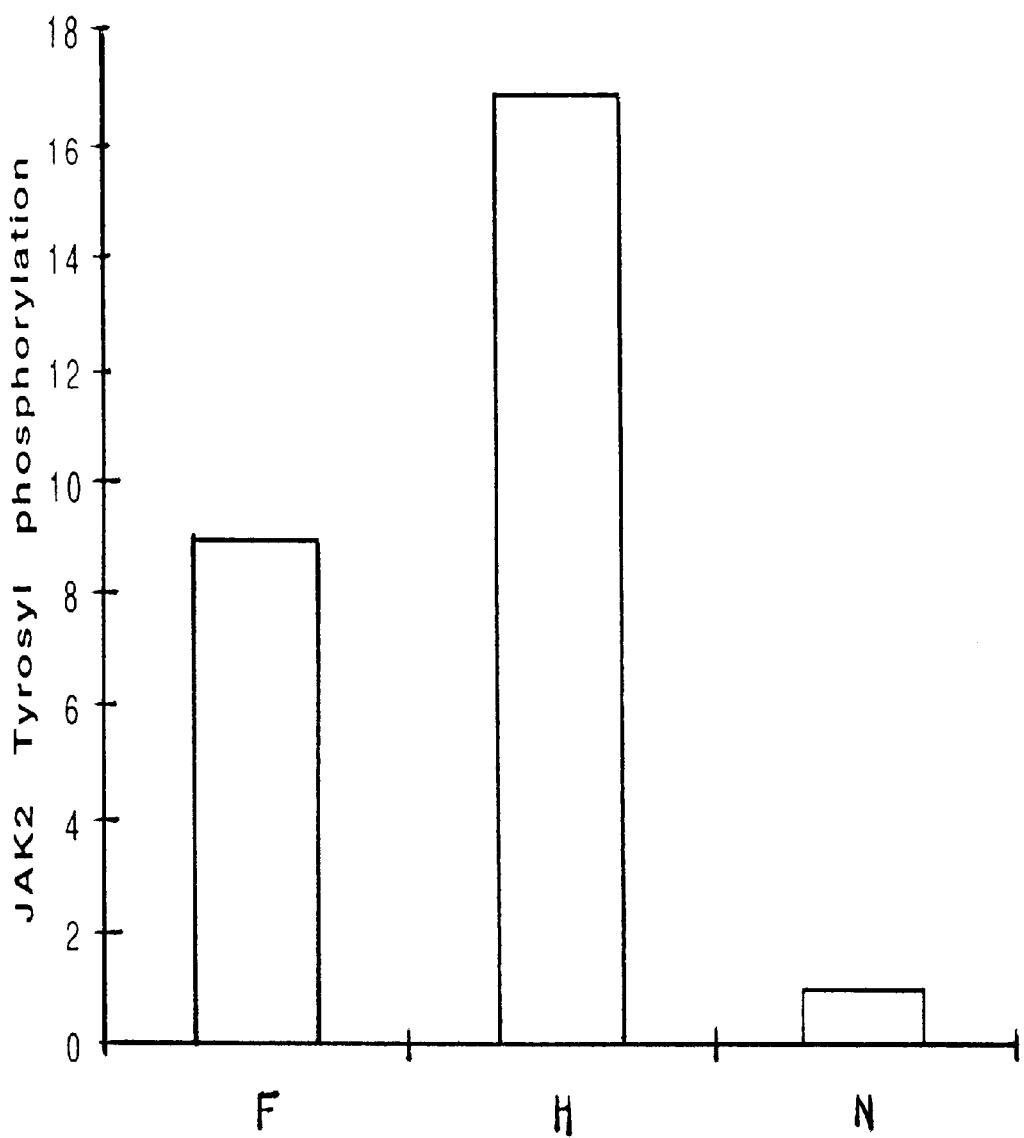
FIG. 17B is a densitometric representation of the blots [FIG. 17A] showing the relative amounts of phosphotyrosines in JAK2, normalized to the amount of JAK2 precipitated from each cell line.

This example shows C-terminally truncated SH2-Bβ inhibits tyrosyl phosphorylation of JAK2. To test for the presence of other JAK2 binding site(s) besides the SH2 domain in SH2-Bβ, and also whether binding of truncated versions of SH2-Bβ affected the enzymatic activity and tyrosyl phosphorylation of JAK2; experiments were designed to test the ability of truncated forms of SH2-Bβ to bind to JAK2 and alter JAK2 activity when they were co-expressed with JAK2 in COS cells. Recombinant PCR was used to truncate N-terminal Myc-tagged SH2-Bβ at amino acid 555 (SH2-Bβn, lacks the SH2 domain) or 631 (SH2-Bβh, truncated just past the SH2 domain). Truncated and wild-type SH2-Bβ were coexpressed with JAK2 in COS cells. SH2-Bβ or truncated SH2-Bβ was then immunoprecipitated with antibody to cMyc and immunoblotted with anti-JAK2 (FIG. 16, lanes 4–5, upper panel). Both full-length and truncated SH2-Bβ co-precipitated with JAK2, indicating that they formed a complex with JAK2. Surprisingly, when the immunoprecipitates were immunoblotted with phosphotyrosyl binding antibody (anti-PY), tyrosyl phosphorylation of JAK2 that was associated with SH2-Bβn was much lower than that associated with SH2-Bβ or SH2-Bβh (See FIG. 16, lanes 1–3). Because tyrosyl phosphorylation is generally believed to reflect JAK2 kinase activity, these data indicated that SH2-Bβn binds and inhibits JAK2 kinase activity. As expected, SH2-Bβ and SH2-Bβh were tyrosine phosphorylated (FIG. 16, lanes 1 and 2), but SH2-Bβn was not (FIG. 16, lane 3). The lack of phosphorylated tyrosines within SH2-Bβn was consistent with the tyrosine kinase activity of JAK2 bound to SH2-Bβn being inhibited. To provide additional evidence of inhibition of JAK2 kinase activity by SH2-Bβn, JAK2 was coexpressed with SH2-Bβ or with truncated SH2-Bβ in COS cells and immunoprecipitated with anti-JAK2. Immunoblotting with anti-PY revealed that tyrosyl phosphorylation of JAK2 was decreased by co-expression of SH2-Bβn, but not by co-expression of SH2-Bβ or SH2-Bβh (FIG. 17A, lanes 1–3). When normalized to the amount of JAK2 immunoprecipitated by the anti-JAK2 for each plate of cells, SH2-Bβn inhibited tyrosine phosphorylation of JAK2 by almost 90% (FIG. 17B), as compared with SH2-Bβ. This example clearly shows that the N-terminus of SH2-Bβ (expressed as a truncated protein, SH2-Bβn), inhibits JAK2 tyrosine kinase activity. Hence, one can use this vital information, to identify potential sites that can be targeted to inhibit JAK2 kinase activity.

EXAMPLE 7

Figure 18:
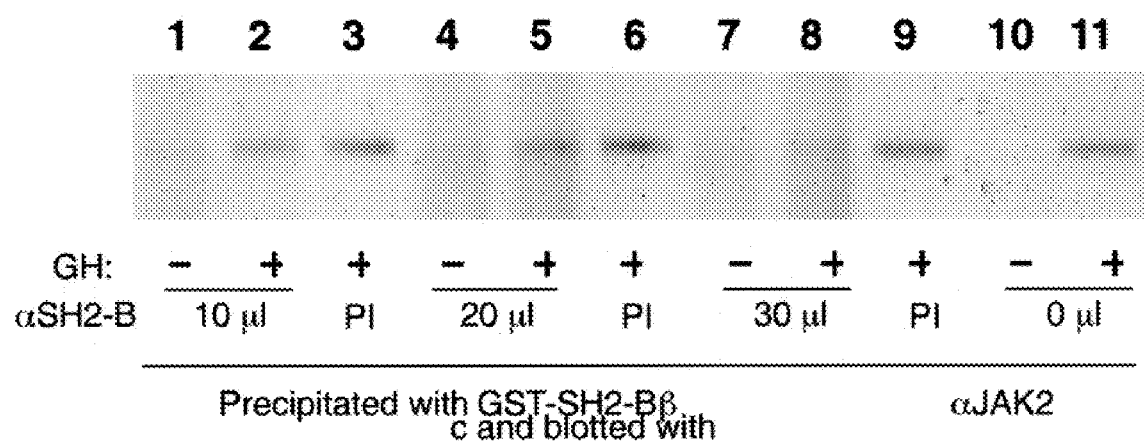
FIG. 18 is a photograph of a representative immunoblot showing αSH2-B interferes with the association of GST-SH2-Bβc with JAK2 in GH stimulated 3T3-F442A cells. Cell lysates were incubated with GST-SH2-Bβc fusion protein immobilized on agarose beads pre-treated with the indicated amount of αSH2-B (lanes 1–2, 4–5, 7–8 and 10–11) or pre-immune serum (PI, lanes 3, 6 and 9). Proteins bound to GST-SH2-Bβc were separated by SDS-PAGE and immunoblotted with αJAK2.

This example shows anti-SH2-B interferes with GST-SH2-Bβc binding to JAK2. To test whether the binding of GST-SH2-Bβ to JAK2 could be used as a drug screening assay, it was examined whether anti-SH2-B could block binding of JAK2 to the C-terminal portion of SH2-B(SH2-Bβc) fused to glutathione-S-transferase (GST). GST-SH2-Bβc was immobilized on glutathione-agarose beads and incubated for 1 hour with the indicated amount of anti-SH2-B or pre-immune serum (PI). Lysates from 3T3-F442A fibroblasts treated for 15 min with or without GH were incubated with the immobilized GST-SH2-Bβc in the presence of anti-SH2-B or PI. Bound proteins were eluted with sodium dodecyl sulfate-containing buffer, separated by SDS-PAGE and immunoblotted with αJAK2. The results (See FIG. 18, lanes 10 and 11), indicated that GST-SH2-Bβc binds to JAK2 in a GH-dependent fashion. Treatment with anti-SH2-B inhibited the binding of GST-SH2-Bβc to JAK2 in a dose-dependent fashion (See FIG. 18, lanes 1–9). 30 μl of αSH2-B almost completely abolished the interaction of GST-SH2-Bβc with JAK2 (FIG. 18, lane 8). The data obtained in this example suggested that similar methods can be used to screen for compounds/drug candidates that inhibit the interaction of SH2-B with JAK2.

EXAMPLE 8

Figure 19:
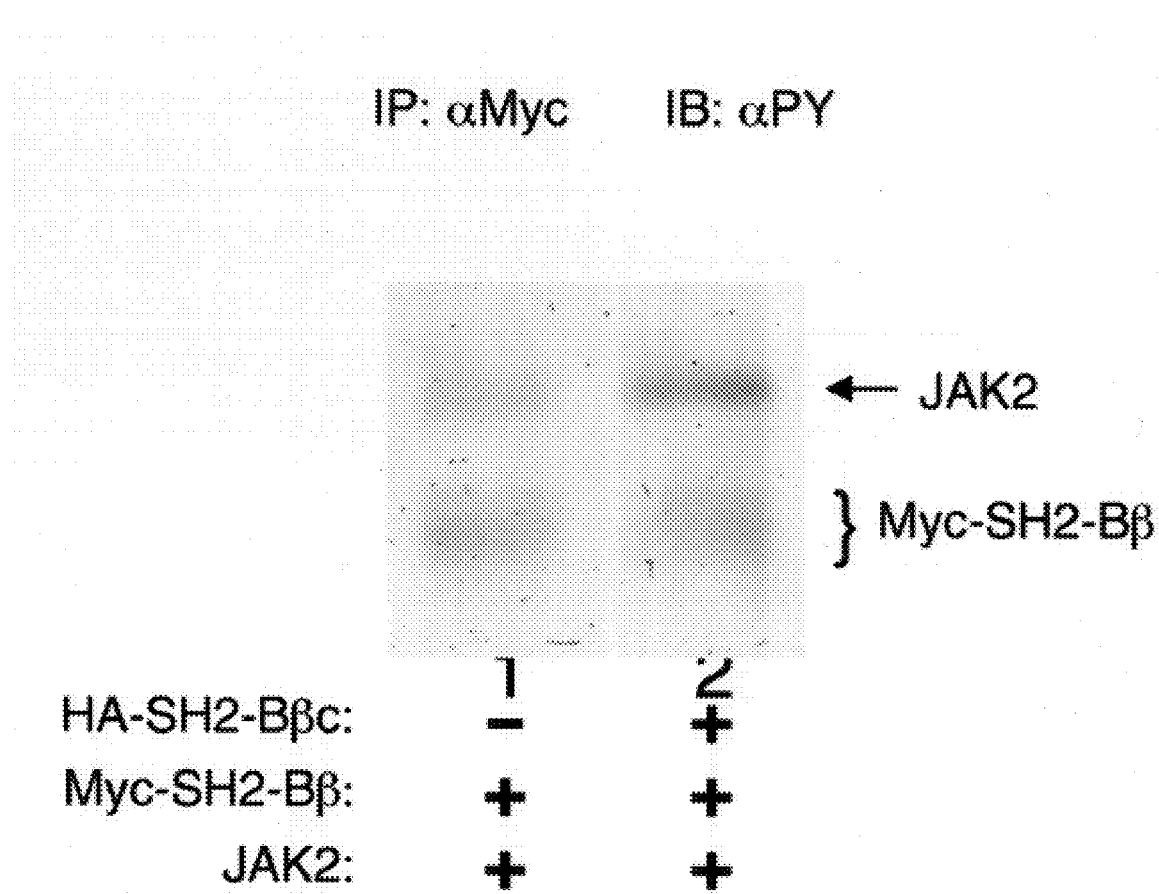
FIG. 19 is a photograph of a representative immunoblot showing SH2-Bβc enhances tyrosyl phosphorylation of JAK2 in COS cells. Plasmids encoding Myc-tagged full-length SH2-Bβ and JAK2 were coexpressed in COS cells. with (lane 1) or without HA-tagged truncated SH2-Bβc (lane 2). Protein lysates were immunoprecipitated with αMyc and immunoblotted with αPY.

This example shows that SH2-Bβ enhances tyrosyl phosphorylation of JAK2. Since SH2-Bβ significantly inhibits JAK2 kinase activity, while full-length SH2-Bβ slightly increases the kinase activity of JAK2 when overexpressed in COS cells (See example 7), it appeared likely that the C-terminus of SH2-Bβ, was responsible for the enhanced JAK2 kinase activity. To test this possibility, COS cells were cotransfected with plasmids encoding JAK2 with empty plasmids (See FIG. 19, lane 1) or the same plasmids encoding HA-tagged SH2-Bβc (lane 2). Proteins in cell lysates were immunoprecipitated with anti-Myc and immunoblotted with anti-phosphotyrosine. As expected, JAK2 co-immunoprecipitated with Myc-SH2-Bβ, and both JAK2 and Myc-SH2-Bβ were tyrosyl phosphorylated. However, coexpression of the C-terminus of SH2-Bβ containing the entire SH2 domain (SH2-Bβc) increased the tyrosyl phosphorylation of JAK2 (lane 2) approximately 3-fold. This indicates that the SH2-Bβc fragment was responsible for the enhanced JAK2 kinase activity.

EXAMPLE 9

This example shows that overexpression of SH2-Bβ causes changes in cellular morphology. To gain insight into the cellular functions of SH2-Bβ, confocal microscopy was used to examine its distribution in cells in the absence or presence of ligand. The effect of overexpressing WT and mutant SH2-Bβ on cellular morphology was also examined. To carry out these studies, cells were transiently transfected with Green Fluorescent protein (GFP)-tagged SH2-Bβ. This approach also had several advantages over immunolocalization: 1) it enabled the visualization of SH2-Bβ in living cells; 2) it allowed the study of single cells prior to and during ligand stimulation for periods of minutes to several hours; 3) it allowed the visualization of only those cells that expressed the required construct. This was especially advantageous for looking at effects of overexpression of WT and dominant negative proteins since one can examine those cells which express the most protein. When expressed in COS cells, GFP-SH2-Bβ was Tyr phosphorylated by overexpressed, constitutively activated JAK2, indicating that GFP-tagged and untagged SH2-Bβ are regulated similarly.

Figure 20:
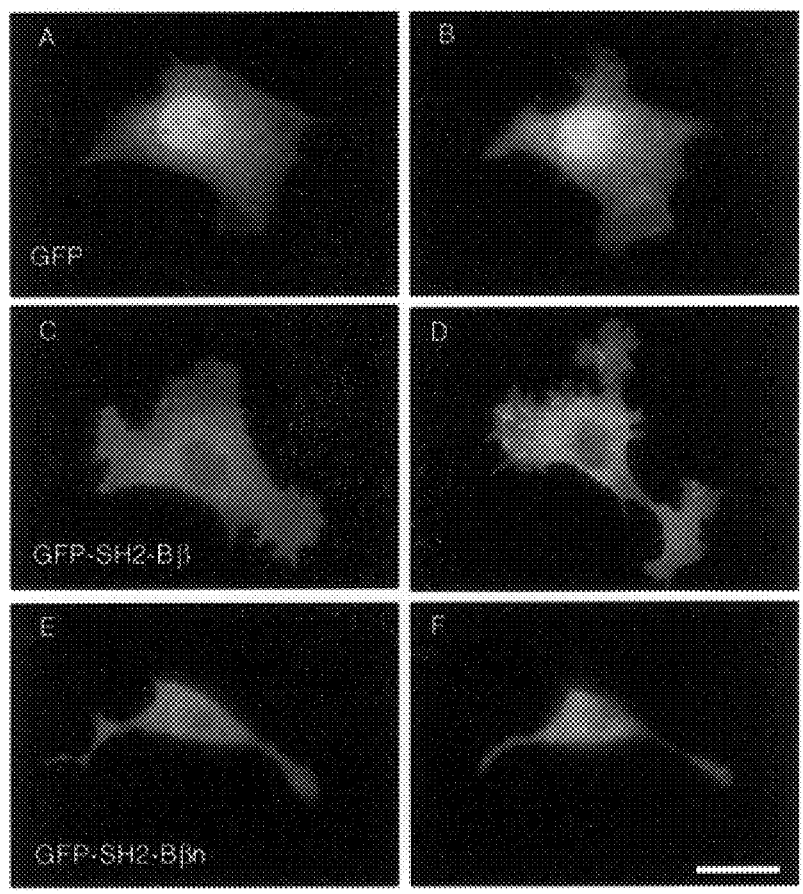
FIGS. 20A–F are confocal microscopy photographs, showing SH2-Bβ enhances whereas SH2-Bβn inhibits PDGF-induced membrane ruffling and lamellipodia formation. NIH-3T3 cells were transfected with 1 μg pGFP(A, B), pGFP-SH2-Bβ (C, D), pGFP-SH2-Bβn (E,F) by liposome-mediated transfer (Lipofectin). Forty-eight hours after transfection and 16 hours after serum deprivation, confocal images of the same cell in physiological saline were captured prior to (A,C,E) and 10 min after (B,D,F) addition of 12.5 ng/ml hPDFG-BB. Scale bar represents 20 μm.
Figure 21:
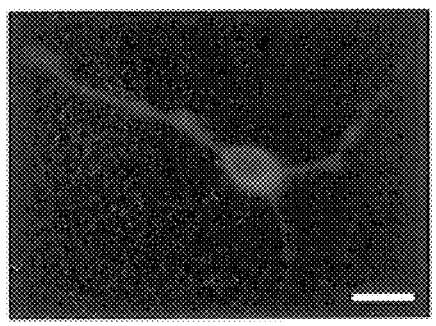
FIG. 21 is a confocal microscopy photograph showing overexpression of SH2-Bβ can lead to development of a neuron-like morphology. NIH-3T3 cells were transfected with 1 μg pGFP-SH2-Bβ by liposome-mediated transfer (Lipofectin). 48 hours post-transfection, and 16 hours after serum deprivation, live cells in physiological saline were imaged by confocal microscopy. Approximately, 12% of cells transfected with pGFP-SH2-Bβ, but not the pGFP, have a condensed cell body and long (50–100 µm), thin processes. Scale bar represents 20 µm.
Figure 22:
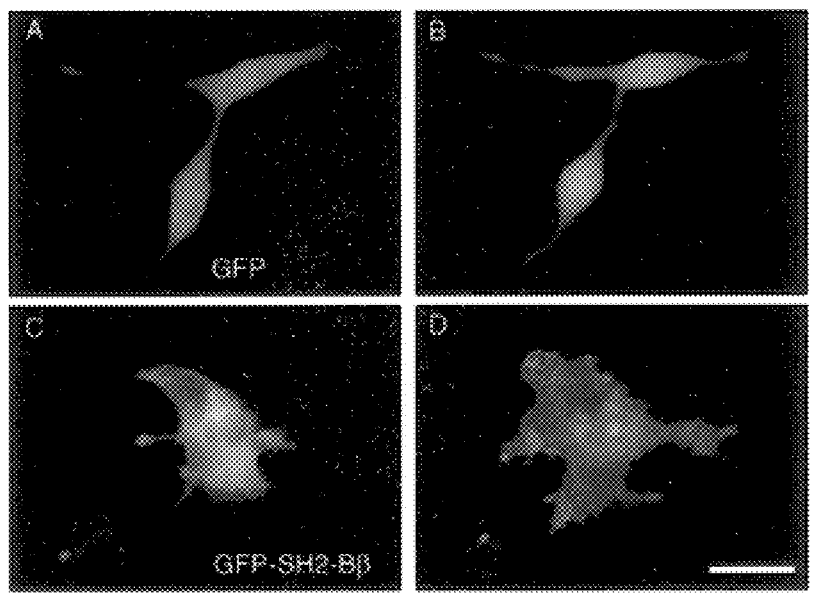
FIGS. 22A–D are confocal microscopy photographs, showing SH2-Bβ promotes cell-spreading, membrane ruffling and lamellipodia formation in response to GH. 2C4 cells stably expressing hGHR were transfected with 1 µg pGFP (A, B), pGFP-SH2-Bβ (C, D), by $CaPO_4$ precipitation and imaged by confocal microscopy prior to (A,C,E) and 15 min after (B,D) addition of 500 ng/ml hGH. Scale bar represents 20 µm.

Next, GFP-SH2-Bβ was expressed in 2C4-GHR cells which expressed low levels of endogenous SH2-Bβ. GFP-SH2-Bβ localized predominantly in the cytoplasm. Overexpression of SH2-Bβ caused substantial cell spreading and flattening (compare FIGS. 22A and C). GH induced pronounced membrane ruffling and lamellipodia formation (FIGS. 22C, D) in ~20% of the cells and GFP-SH2-Bβ appeared to be concentrated at regions of membrane extension. No such response to GH was seen in cells expressing GFP alone (FIGS. 22A, B). These results suggested that SH2-Bβ may link GH and JAK2 activation to cytoskeletal rearrangements. Because PDGF also utilized SH2-Bβ as a signaling molecule, and PDGF induced morphological changes are known, the effect of overexpressing GFP-SH2-Bβ in NIH-3T3 cells was investigated in the presence and absence of PDGF. NIH-3T3 cells expressed endogenous SH2-Bβ which was Tyr phosphorylated in response to PDGF. Overexpression of GFP-SH2-Bβ, but not GFP alone, caused a significant percentage of the cells to send out short processes. The processes often had thin, finger-like extensions resembling filopodia emerging from their sides and leading edge. GFP-SH2-Bβ localized to the cytoplasm in the absence of PDGF. In cells expressing GFP alone, PDGF stimulation for 5–10 min resulted in modest membrane ruffling and lamellipodia formation, as expected (FIGS. 20A, B). In GFP-SH2-Bβ expressing cells, the morphological changes were dramatically enhanced and GFP-SH2-Bβ appeared concentrated in the membrane ruffles (FIGS. 20C, D). About 12% of the cells changed morphology drastically, from a fibroblast to a neuron-like cell, with a condensed cell body from which emanated thin, long processes that resembled neurites (FIG. 21). About 30% of cells (transfected with either GFP or GFP-SH2-Bβ assumed this shape when stimulated with PDGF for >60 min, suggesting that overexpression of SH2-Bβ enhanced this PDGF stimulated pathway. When GFP-tagged C-terminal truncated SH2-Bβ lacking the SH2-domain (SH2-Bβn, a potential dominant negative)(See FIG. 2C) was overexpressed in NIH-3T3 or 2C4-GHR cells, many cells died. The few remaining cells that expressed the protein showed an aberrant shape that was not altered by PDGF (FIGS. 20E, F). In this example, the results provide evidence that SH2-Bβ may be involved in changes in cellular morphology and may also be vital for cell survival. They also provide evidence of the utility of using GFP-tagged SH2-Bβ to study the subcellular localization of various mutated SH2-Bβs and the morphological consequences of overexpressing of WT and mutant forms of SH2-Bβ.

EXAMPLE 10

Figure 23:
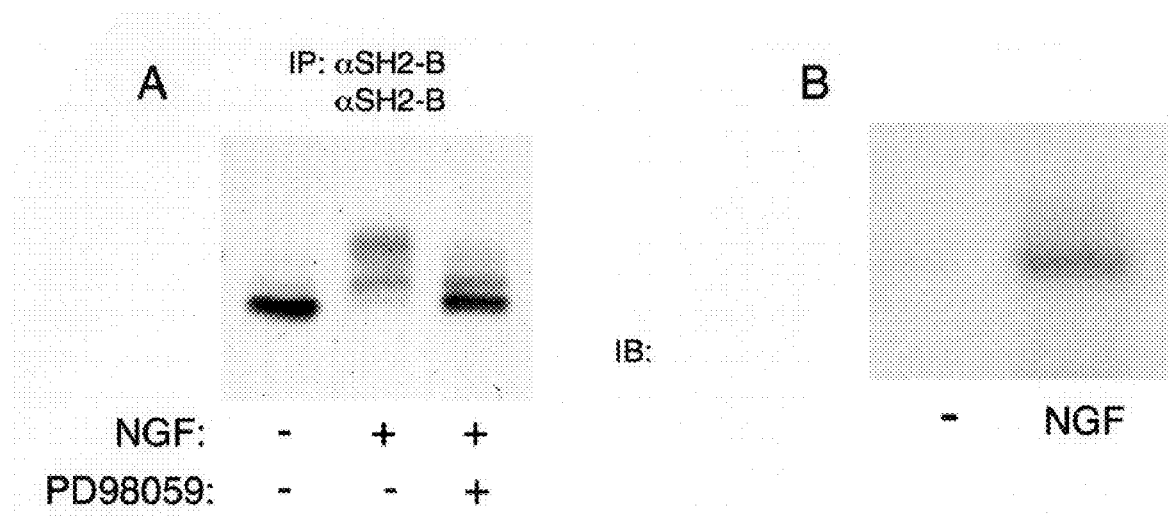
FIG. 23A is a photograph of a representative immunoblot showing NGF—activated MEK or a kinase downstream of MEK may be involved in Ser and/or Thr phosphorylation of SH2-B. PC12 cells were treated in the presence or absence of the MEK inhibitor (PD98059) with NGF. Proteins in cell lysates were immunoprecipitated with αSH-2B and immunoblotted with αSH-2B. NGF causes a dramatic decrease in SH2-B migration, presumably due to Ser/Thr phosphorylation (ligand induced shifts are due to phosphorylation) [Compare lanes 1 and 2]. MEK inhibitor significantly inhibits NGF-induced mobility shift of SH-2B (See lane 3).
FIG. 23B is a photograph of a representative autoradiogram showing SH2-Bβ is phoshorylated by activated ERK ½ in vitro. Proteins from NOF-stimulated PC12 lysates were immunoprecipitated with αERK2 and the immunoprecipitates collected on protein-A agarose beads. These were incubated with GST-SH2-Bβ. The latter was purified with glutathione-agarose beads and SH2-Bβ was cleaved off GST beads by thrombin. SH2-Bβ was resolved by SDS-PAGE followed by autoradiography. SH2-Bβ is phoshorylated by activated ERK ½ in vitro (See lane 2).
Figure 24:
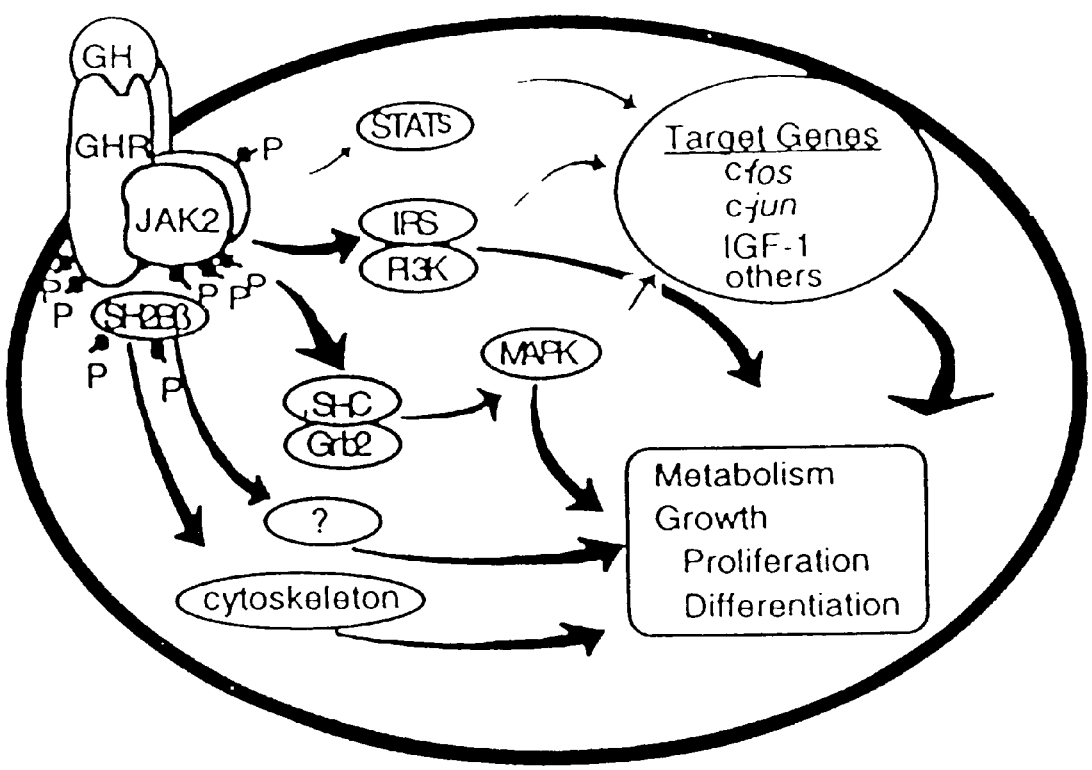
FIG. 24 sets out a number of signaling molecules activated by recruitment tp JAK2-GHR complexes.
Figure 25:
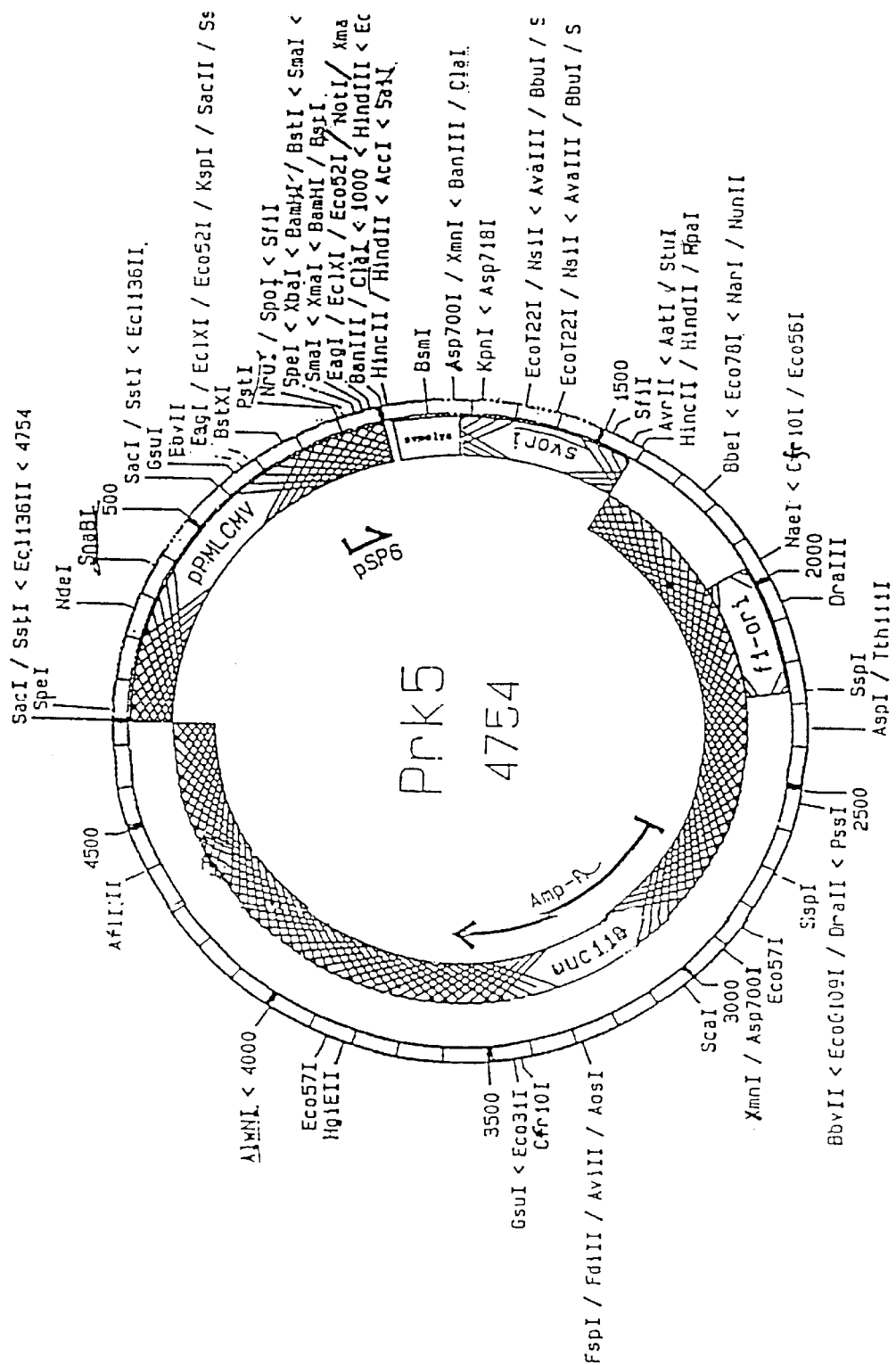
FIG. 25. projects cDNAs encoding both wild-type murine JAK2 and mutant murine JAK2.
Figure 26:
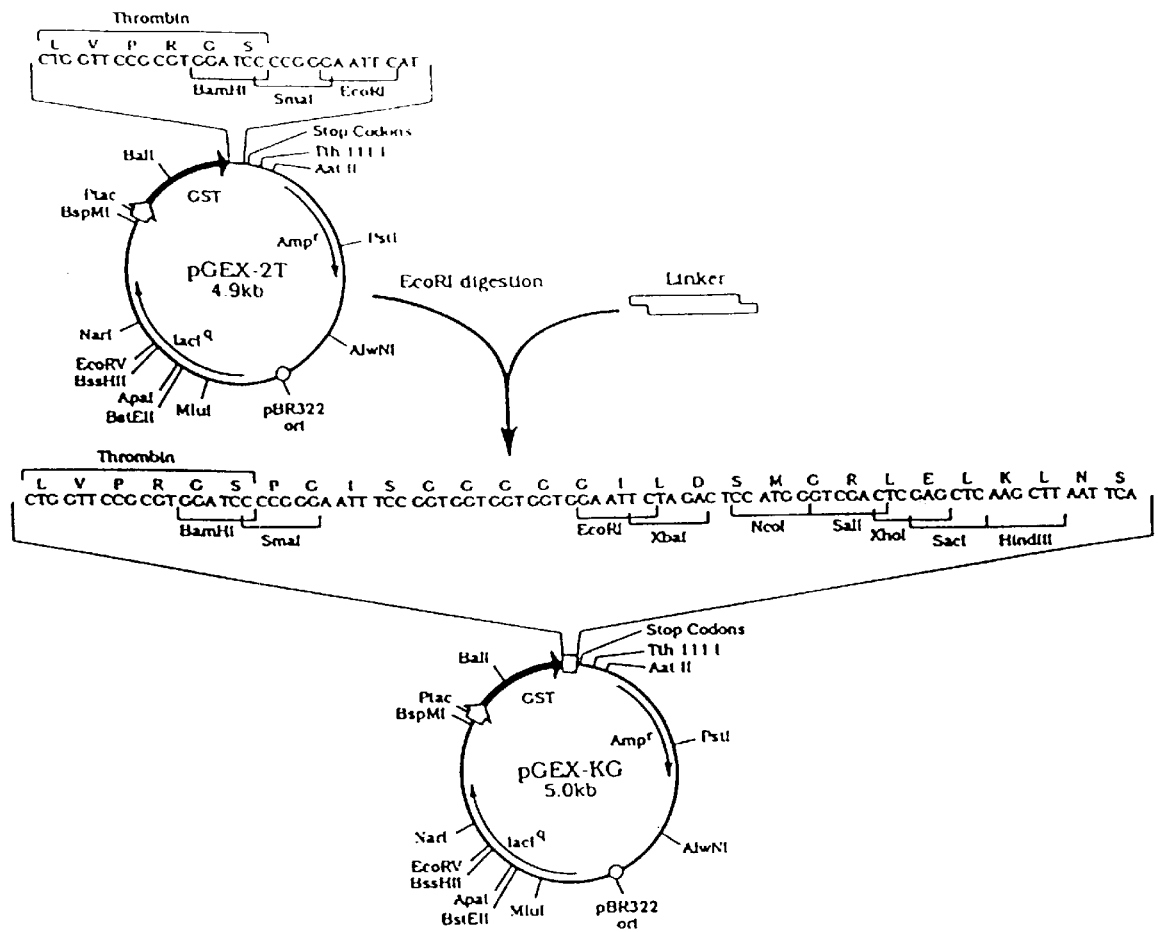
FIG. 26 projects the PCR products cloned into pGEX-KG, thereby, producing a GST fusiion protien.

This example shows that SH2-Bβ is a substrate of ERK½ involved in NGF signaling. PC12 cells were deprived of serum overnight and treated with the MEK inhibitor (100 μM PD98059) or DMSO (solvent of PD98059) for 30 min followed by stimulation with 75 ng/ml NGF for 5 min (See FIG. 23A). Proteins in cell lysates were immunoprecipitated with αSH2-B and immunoblotted with αSH2-B. NGF causes a dramatic decrease in SH2-B migration (See lane 2) presumably due to Ser/Thr phosphorylation because ligand-induced shifts in SH2-Bβ are due to phosphorylation (FIG. 11) and NGF is unable to stimulate tyrosyl phosphorylation of SH2-B (FIG. 13). The MEK inhibitor significantly inhibits NGF-induced mobility shift of SH2-B (See lane 3). These data suggest that NGF promotes Ser and/or Thr phosphorylation of SH2-2 and that NGF-activated MEK or a kinase downstream of MEK (e.g. ERKs 1 and 2) is involved in phosphorylation of SH2-Bβ.

Next, PC12 cells were deprived of serum overnight and stimulated with 75 ng/ml NGF for 10 min. Proteins in cell lysates were immunoprecipitated with αERK2 (Santa Cruz) and the precipitates were collected on protein-A agarose beads. αERK2 immunoprecipitates were incubated with 10 μg GST-SH2-Bβ at room temperature for 30 in kinase reaction buffer (50 mM HEPES, PH 7.4; 10 mM MgGl$_2$; 0.5 mM DTT; 5 mM Na$_3$VO$_4$; 30 μM ATP; 15 μCi ($^{32}$P) γ-ATP). GST-SH2-Bβ was purified using glutathione-agarose beads (The reaction mixture was spun down and the supernatants were precipitated with glutathione-agarose beads. The precipitates were washed extensively with lysis buffer) and SH2-Bβ was cleaved off GST beads by thrombin. SH2-Bβ was resolved by 7.5% SDS-PAGE followed by autoradiography. The results showed that SH2-Bβ is phosphorylated by activated ERK ½ in vitro (See FIG. 23B, lane 2).

From the above, it should be clear that the present invention provides methods and compositions useful for identifying signaling pathway agonists and antagonists. The methods and compositions are, in this manner, useful for identifying compounds that may be used in vitro and in vivo in the context of hormone and cytokine responses.

We claim:

1. An isolated nucleic acid sequence encoding a fragment of a protein, wherein said fragment is selected from the group consisting of residues 1–631 and residues 527–670 of the amino acid sequence set forth in SEQ ID NO:2.

2. An isolated nucleic acid sequence encoding full-length SH2-Bβ as set forth in SEQ ID NO:2.

3. An isolated nucleic acid sequence comprising SEQ ID NO:1.

4. A vector comprising the nucleic acid sequence of claim 2.

5. A host cell transfected with the vector of claim 4.

* * * * *

UNITED STATES PATENT AND TRADEMARK OFFICE
CERTIFICATE OF CORRECTION

PATENT NO.    : 6,312,941 B1
DATED         : November 6, 2001
INVENTOR(S)   : Carter-Su et al.

It is certified that error appears in the above-identified patent and that said Letters Patent is hereby corrected as shown below:

<u>Title page,</u>
Item [75], Inventors, "David S. Karow, Northville" should be deleted.

Signed and Sealed this

Fourth Day of February, 2003

JAMES E. ROGAN
*Director of the United States Patent and Trademark Office*